(12) United States Patent
Kennedy et al.

(10) Patent No.: US 11,946,106 B2
(45) Date of Patent: Apr. 2, 2024

(54) METHODS AND SYSTEMS TO IMPROVE THE SIGNAL TO NOISE RATIO OF DNA METHYLATION PARTITIONING ASSAYS

(71) Applicant: GUARDANT HEALTH, INC., Palo Alto, CA (US)

(72) Inventors: Andrew Kennedy, San Diego, CA (US); William J. Greenleaf, Menlo Park, CA (US)

(73) Assignee: Guardant Health, Inc., Palo Alto, CA (US)

( * ) Notice: Subject to any disclaimer, the term of this patent is extended or adjusted under 35 U.S.C. 154(b) by 0 days.

(21) Appl. No.: 18/087,724

(22) Filed: Dec. 22, 2022

(65) Prior Publication Data

US 2023/0130140 A1    Apr. 27, 2023

Related U.S. Application Data

(63) Continuation of application No. 17/489,677, filed on Sep. 29, 2021.

(60) Provisional application No. 63/105,183, filed on Oct. 23, 2020, provisional application No. 63/086,000, filed on Sep. 30, 2020.

(51) Int. Cl.
| | |
|---|---|
| *C12Q 1/6886* | (2018.01) |
| *C12N 9/22* | (2006.01) |
| *C12N 15/10* | (2006.01) |
| *C12Q 1/6809* | (2018.01) |
| *C12Q 1/683* | (2018.01) |

(52) U.S. Cl.
CPC ............ *C12Q 1/6886* (2013.01); *C12N 9/22* (2013.01); *C12N 15/1065* (2013.01); *C12Q 1/6809* (2013.01); *C12Q 1/683* (2013.01); *C12N 2800/80* (2013.01); *C12Q 2600/112* (2013.01); *C12Q 2600/154* (2013.01); *C12Q 2600/156* (2013.01); *C12Q 2600/166* (2013.01)

(58) Field of Classification Search
None
See application file for complete search history.

(56) References Cited

U.S. PATENT DOCUMENTS

| | | |
|---|---|---|
| 5,912,148 A | 6/1999 | Eggerding |
| 6,130,073 A | 10/2000 | Eggerding |
| 6,210,891 B1 | 4/2001 | Nyren et al. |
| 6,258,568 B1 | 7/2001 | Nyren |
| 6,582,908 B2 | 6/2003 | Fodor et al. |
| 6,833,246 B2 | 12/2004 | Balasubramanian |
| 6,969,488 B2 | 11/2005 | Bridgham et al. |
| 7,115,400 B1 | 10/2006 | Adessi et al. |
| 7,169,560 B2 | 1/2007 | Lapidus et al. |
| 7,170,050 B2 | 1/2007 | Turner et al. |
| 7,282,337 B1 | 10/2007 | Harris |
| 7,302,146 B2 | 11/2007 | Turner et al. |
| 7,313,308 B2 | 12/2007 | Turner et al. |
| 7,329,492 B2 | 2/2008 | Hardin et al. |
| 7,476,503 B2 | 1/2009 | Turner et al. |
| 7,482,120 B2 | 1/2009 | Buzby |
| 7,501,245 B2 | 3/2009 | Quake et al. |
| 7,537,898 B2 | 5/2009 | Bost et al. |
| 8,486,630 B2 | 7/2013 | Pan et al. |
| 9,598,731 B2 | 3/2017 | Talasaz |
| 9,738,894 B2 | 8/2017 | Elmen et al. |
| 9,850,523 B1 | 12/2017 | Chudova et al. |
| 9,902,992 B2 | 2/2018 | Talasaz et al. |
| 2001/0053519 A1 | 12/2001 | Fodor et al. |
| 2003/0152490 A1 | 8/2003 | Trulson et al. |
| 2011/0160078 A1 | 6/2011 | Fodor et al. |
| 2011/0237444 A1 | 9/2011 | Clancy et al. |
| 2013/0157266 A1 | 6/2013 | Hanna et al. |
| 2015/0299812 A1 | 10/2015 | Talasaz |
| 2015/0368708 A1 | 12/2015 | Talasaz |

(Continued)

FOREIGN PATENT DOCUMENTS

| | | |
|---|---|---|
| WO | 2017190215 A1 | 11/2017 |
| WO | 2018009723 A1 | 1/2018 |

(Continued)

OTHER PUBLICATIONS

Astier, Y. et al. "Toward Single Molecule DNA Sequencing: Direct Identification of Ribonucleoside and Deoxyribonucleoside 5'-Monophosphates by Using an Engineered Protein Nanopore Equipped with a Molecular Adapter" J Am Chem Soc (2006) 128(5):1705-1710.

Belinsky, S.A. "Unmasking the lung cancer epigenome" Annu. Rev. Physiol. (2015) 77:453-474.

Bock, C. et al. "Quantitative comparison of genome-wide DNA methylation mapping technologies" Nature Biotech (2010) 28:1106-1114.

Booth, M.J. et al. "Quantitative sequencing of 5-methylcytosine and 5-hydroxymethylcytosine at single-base resolution" Science (2012) 336(6083):934-937.

(Continued)

*Primary Examiner* — Katherine D Salmon
(74) *Attorney, Agent, or Firm* — Indhu Kanakaraj

(57) ABSTRACT

In an aspect, the present disclosure provides a method for determining a methylation status comprises: providing a biological sample of nucleic acid molecules; partitioning at least a subset of the nucleic acid molecules in the biological sample based on the methylation status of the nucleic acid molecules into a plurality of partitioned sets; digesting at least a subset of the one or more partitioned sets in the plurality of partitioned sets with at least one methylation sensitive restriction enzyme; enriching at least a subset of the nucleic acid molecules in the plurality of partitioned sets for genomic regions of interest, wherein the at least a subset of the nucleic acid molecules comprises digested nucleic acid molecules in the one or more partitioned sets; and determining methylation status at one or more genetic loci of the nucleic acid molecules in at least one of the partitioned sets.

29 Claims, 13 Drawing Sheets

(56) References Cited

U.S. PATENT DOCUMENTS

| | | |
|---|---|---|
| 2016/0040229 A1 | 2/2016 | Talasaz et al. |
| 2016/0046986 A1 | 2/2016 | Eltoukhy et al. |
| 2017/0211143 A1 | 7/2017 | Shendure et al. |
| 2018/0305738 A1* | 10/2018 | Kennedy .............. C12Q 1/6855 |
| 2019/0361010 A1* | 11/2019 | Belhocine .............. C12N 15/85 |

FOREIGN PATENT DOCUMENTS

| | | |
|---|---|---|
| WO | 2018119452 A2 | 6/2018 |
| WO | 2020160414 A1 | 8/2020 |

OTHER PUBLICATIONS

Cock, Pja, et al. "The Sanger FASTQ file format for sequences with quality scores, and the Solexa/Illumina FASTQ variants" NAR (2009) 38(6):1767-1771.

Cuddapah, S. et al. "Global analysis of the insulator binding protein CTCF in chromatin barrier regions reveals demarcation of active and repressive domains" Genome Res (2009) 19:24-32.

Danecek, P. et al. "The variant call format and VCFtools" Bioinformatics (2011) 27(15):2156-2158.

Ehrlich, M. "DNA hypomethylation in cancer cells" Epigenomics 1:239-259.

Freier, S.M. et al. "The ups and downs of nucleic acid duplex stability: structure-stability studies on chemically-modified DNA:RNA duplexes" Nucl Acids Res (1997) 25:4429-4443.

Furonaka, O. et al. "Aberrant methylation and loss of expression of O6-methylguanine-DNA methyltransferase in pulmonary squamous cell carcinoma and adenocarcinoma" Pathol Int (2005) 55:303-309.

Gale, D. et al. "Development of a highly sensitive liquid biopsy platform to detect clinically—relevant cancer mutations at low allele fractions in cell-free DNA" PLoS One (2018) 13:e0194630.

Gomes, A. et al. "Promoter hypermethylation of DNA repair genes MLH1 and MSH2 in adenocarcinomas and squamous cell carcinomas of the lung" Rev. Port. Pneumol. (2014) 20:20-30.

Greer, E.L. et al. "DNA Methylation on N6-Adenine in C. elegans" Cell (2015) 161(4):868-878.

Guo, M. et al. "Hypermethylation of the GATA genes in lung cancer" Clin Cancer Res (2004) 10(23):7917-7924.

Guo, Y.A. et al. "Mutation hotspots at CTCF binding sites coupled to chromosomal instability in gastrointestinal cancers" Nature Commun (2018) 9:1520.

Han, D. et al. "A highly sensitive and robust method for genome-wide 5hmC profiling of rare cell populations" Mol Cell. (2016) 63(4):711-719.

Heller, G. et al. "Expression and methylation pattern of TSLC1 cascade genes in lung carcinomas" Oncogene (2006) 25:959-968.

Hon, G.C. et al. "Global DNA hypomethylation coupled to repressive chromatin domain formation and gene silencing in breast cancer" Genome Res (2012) 22:246-258.

Hopkins-Donaldson, S. et al. "Silencing of death receptor and caspase-8 expression in small cell lung carcinoma cell lines and tumors by DNA methylation" Cell Death Differ. (2003) 10:356-64.

Hulbert, A. et al. "Early Detection of Lung Cancer Using DNA Promoter Hypermethylation in Plasma and Sputum" Clin. Cancer Res. (2017) 23:1998-2005.

International search report and written opinion dated Jan. 20, 2022 for PCT/US2021/071649.

International search report and written opinion dated Jan. 21, 2022 for PCT/US2021/071648.

Iurlaro, M. et al. "A screen for hydroxymethylcytosine and formylcytosine binding proteins suggests functions in transcription and chromatin regulation" Genome Biology (2013) 14:R119.

Kang, S. et al. "CancerLocator: non-invasive cancer diagnosis and tissue-of-origin prediction using methylation profiles of cell-free DNA" Genome Biology (2017) 18(1):53 XP055682390.

Katainen, R. et al. "CTCF/cohesin-binding sites are frequently mutated in cancer" Nature Genetics (2015) 47:818-821.

Kikuchi, S. et al. "Promoter Methylation of DAL-1/4.1B Predicts Poor Prognosis in Non Small Cell Lung Cancer" Clin Canc Res (2005) 11:2954-2961.

Kim, D-H. et al. "p16INK4a and Histology-specific Methylation of CpG Islands by Exposure to Tobacco Smoke in Non-Small Cell Lung Cancer" Canc Res (2001) 61:3419-3424.

Kim, D-H. et al. "Promoter methylation of DAP-kinase: association with advanced stage in non-small cell lung cancer" Oncogene. (2001) 20:1765-1770.

Kinde, et al. Detection and quantification of rare mutations with massively parallel sequencing. Proc Natl Acad Sci U S A. Jun. 7, 2011;108(23):9530-5. doi: 10.1073/pnas.1105422108. Epub May 17, 2011.

Kinde, et al. Supplemental Information, Detection and quantification of rare mutations with massively parallel sequencing. Proc Natl Acad Sci U S A. Jun. 7, 2011;108(23):1-10.

Kou, R. et al. "Benefits and Challenges with Applying Unique Molecular Identifiers in Next Generation Sequencing to Detect Low Frequency Mutations" PLoS One (2016) 11: e0146638, https://doi.org/10.1371/journal.pone.0146638.

Kumar, S. et al. "Epigenetics of Modified DNA Bases: 5-Methylcytosine and Beyond" Frontiers Genet (2018) 9:640.

Lam, K. et al. "DNA methylation based biomarkers in colorectal cancer: A systematic review" Biochim Biophys Acta (2016 ) 1866(1):106-20.

Levy, S.E. et al. "Advancements in Next-Generation Sequencing" Ann Rev Genomics & Hum Genetics (2016) 17:95-115.

Li, et al., The Sequence Alignment/Map format and SAMtools, Bioinformatics, 2009, 25(16):2078-9.

Licchesi, J. et al. "Epigenetic alteration of Wnt pathway antagonists in progressive glandular neoplasia of the lung" Carcinogenesis (2008) 29:895-904.

Lissa, D. et al. "Methylation analyses in liquid biopsy" Transl Lung Cancer Res (2016) 5(5):492-504.

Liu, L. et al. "Comparison of Next-Generation Sequencing Systems" J Biomed & Biotech (2012) Article ID251364:1-11.

Liu, Y. et al. "Bisulfite-free direct detection of 5-methylcytosine and 5-hydroxymethylcytosine at base resolution" Nature Biotech (2019) 37(4):424-429.

Maclean, D. et al. "Application of 'next-generation' sequencing technologies to microbial genetics" Nature Rev Microbiol (2009) 7:287-296.

Martin, D. et al. "Genome-wide CTCF distribution in vertebrates defines equivalent sites that aid the identification of disease-associated genes" Nature Structural Mol Bio (2011) 18:708-714.

Moss, J. et al. "Comprehensive human cell-type methylation atlas reveals origins of circulating cell-free DNA in health and disease" Nat Comm (2018) 9:5068.

Ning, Z. et al. "SSAHA: A Fast Search Method for Large DNA Databases" Genome Res (2001) 11:1725-1729.

Ooki, A. et al. "A Panel of Novel Detection and Prognostic Methylated DNA Markers in Primary Non-Small Cell Lung Cancer and Serum DNA" (2017) Clin. Cancer Res. 23:7141-7152.

Palmisano, W. et al. "Aberrant Promoter Methylation of the Transcription Factor Genes PAX5 alpha and beta in Human Cancers" Cancer Res (2003) 63:4620-4625.

Pearson, W.R. et al. "Improved tools for biological sequence comparison" PNAS (1988) 85:2444-2448.

Rhee, H.S. et al. "Comprehensive genome-wide protein-DNA interactions detected at single-nucleotide resolution" Cell (2011) 147:1408-1419.

Schneider, K.U. et al. "Correlation of SHOX2 Gene Amplification and DNA Methylation in Lung Cancer Tumors" BMC Cancer (2011) 11:102.

Schutsky, E.K. et al., "Nondestructive, base-resolution sequencing of 5-hydroxymethylcytosine using a DNA deaminase" Nature Biotech (2018); 36:1083-1090.

Severin, P.M.D. et al. "Cytosine methylation alters DNA mechanical properties" Nucl Acids Res (2011) 39:8740-8751.

Shi, Y-X et al. "Genome-wide DNA methylation profiling reveals novel epigenetic signatures in squamous cell lung cancer" BMC Genomics (2017) 18:901.

(56) References Cited

OTHER PUBLICATIONS

Skvortsova, T.E. et al. "Cell-free and cell-bound circulating DNA in breast tumours: DNA quantification and analysis of tumour-related gene methylation" Br J Cancer (2006) 94(10):1492-1495.

Snyder, M.W. et al. "Cell-free DNA Comprises an In Vivo Nucleosome Footprint that Informs Its Tissues-of-Origin" Cell (2016) 164:57-68 & Supplemental Information.

Song, C-X. et al. "Selective chemical labeling reveals the genome-wide distribution of 5-hydroxymethylcytosine" Nature Biotech (2011) 29:68-72.

Sun, Q et al. "N6-methyladenine functions as a potential epigenetic mark in eukaryotes" Bioessays (2015) 37:1155-1162.

Toyooka, K.O. et al. "Loss of Expression and Aberrant Methylation of the CDH13 (H-Cadherin) Gene in Breast and Lung Carcinomas" Cancer Res. (2001) 61:4556-4560.

Vaisvila, R. et al. "EM-seq: Detection of DNA Methylation at Single Base Resolution from Picograms of DNA" bioRxiv (2019) DOI:10.1101/2019.12.20.884692.

Voelkerding, K.V. et al. "Next-generation sequencing: from basic research to diagnostics" Clin Chem (2009) 55:641-658.

Yamashita, R. et al. "DBTSS: DataBase of Human Transcription Start Sites, progress report 2006" Nucleic Acids Res. (2006) 34(Database issue):D86-D89.

Yu, M. et al. "Base-Resolution Analysis of 5-Hydroxymethylcytosine in the Mammalian Genome" Cell (2012) 149(6):1368-1380.

\* cited by examiner

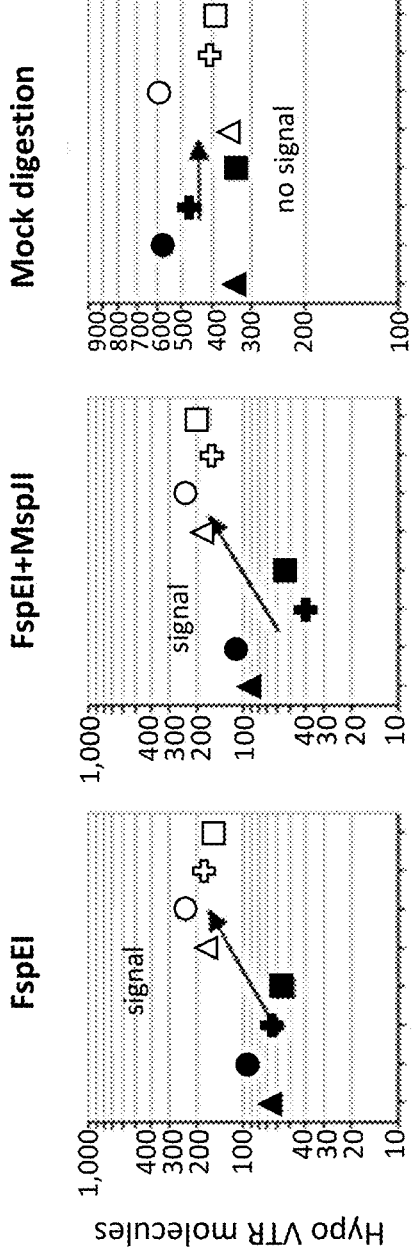
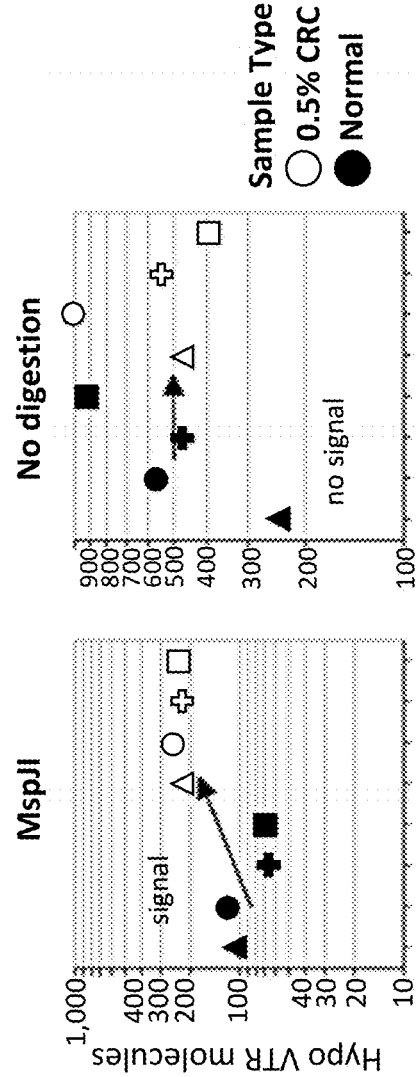
Fig. 10A Fig. 10B Fig. 10C Fig. 10D Fig. 10E

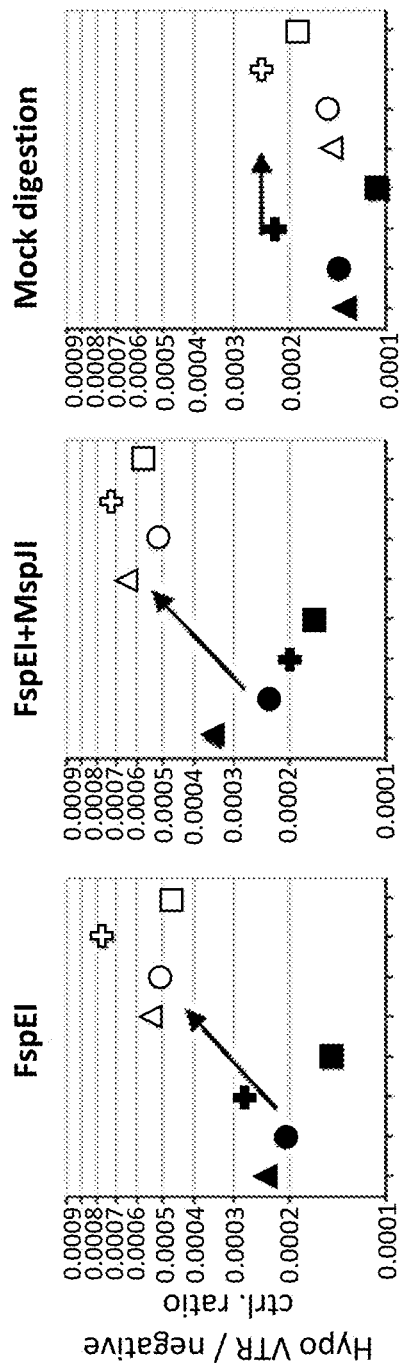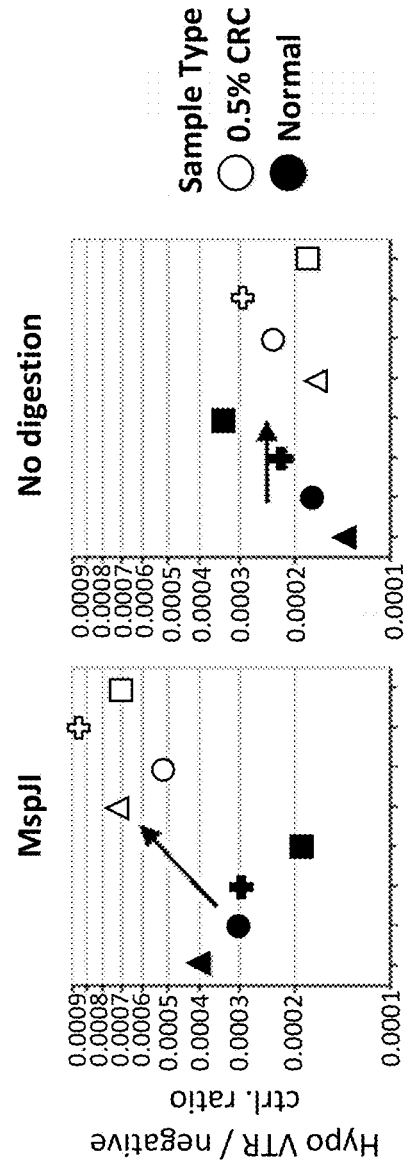

METHODS AND SYSTEMS TO IMPROVE THE SIGNAL TO NOISE RATIO OF DNA METHYLATION PARTITIONING ASSAYS

CROSS-REFERENCE TO RELATED APPLICATIONS

This application is a continuation of U.S. patent application Ser. No. 17/489,677, filed Sep. 29, 2021, which claims the benefit of priority of U.S. Provisional Patent Application No. 63/086,000, filed Sep. 30, 2020, and U.S. Provisional Patent Application No. 63/105,183, filed Oct. 23, 2020, each of which is incorporated by reference herein in its entirety for all purposes.

FIELD OF THE INVENTION

The present disclosure provides compositions and methods related to analyzing nucleic acids, such as DNA, such as cell-free DNA. In some embodiments, the cell-free DNA is from a subject having or suspected of having cancer and/or the cell-free DNA includes DNA from cancer cells. In some embodiments, the DNA is partitioned into a plurality of partitioned sets based on the methylation status of the nucleic acid molecules, and at least a subset of at least one partitioned set is digested with at least one methylation sensitive restriction enzyme.

BACKGROUND

Current methods of cancer diagnostic assays of cell-free nucleic acids (e.g., cell-free DNA or cell-free RNA) may focus on the detection of tumor-related somatic variants, including single nucleotide variants (SNVs), copy number variations (CNVs), fusions, and indels (i.e., insertions or deletions), which are all mainstream targets for liquid biopsy. There is growing evidence that non-sequence modifications like methylation status and fragmentomic signal in cell-free DNA can provide information on the source of cell-free DNA and disease level. The non-sequence modifications of the cell-free DNA, when combined with somatic mutation calling, can yield a more comprehensive assessment of tumor status than that available from either approach alone.

However, it has been challenging to develop accurate and sensitive methods for analyzing liquid biopsy material that provide detailed information regarding nucleobase modifications given the low concentration and heterogeneity of cell-free DNA. Isolating and processing the fractions of cell-free DNA useful for further analysis in liquid biopsy procedures is an important part of these methods. Accordingly, there is a need for improved methods and compositions for analyzing cell-free DNA, e.g., in liquid biopsies.

SUMMARY

The present disclosure aims to meet the need for improved analysis of cell-free DNA and/or provide other benefits. The present disclosure provides methods, compositions, and systems for analyzing nucleic acids. Accordingly, the following exemplary embodiments are provided. Embodiment 1 is a method for analyzing nucleic acid molecules in a biological sample, comprising:
  a) partitioning at least a subset of the nucleic acid molecules in the biological sample, based on the methylation status of the nucleic acid molecules into a plurality of partitioned sets, wherein the biological sample comprises methylated nucleic acid molecules and unmethylated nucleic acid molecules;
  b) digesting at least a subset of the one or more partitioned sets in the plurality of partitioned sets with at least one methylation sensitive restriction enzyme; and
  c) determining methylation status at one or more genetic loci of the nucleic acid molecules in at least one of the partitioned sets.

Embodiment 2 is a method for determining methylation status of nucleic acid molecules, comprising:
  a) providing a biological sample of nucleic acid molecules, wherein the nucleic acid molecules comprises methylated nucleic acid molecules and unmethylated nucleic acid molecules;
  b) partitioning at least a subset of the nucleic acid molecules in the biological sample based on the methylation status of the nucleic acid molecules into a plurality of partitioned sets;
  c) digesting at least a subset of the one or more partitioned sets in the plurality of partitioned sets with at least one methylation sensitive restriction enzyme;
  d) enriching at least a subset of the nucleic acid molecules in the plurality of partitioned sets for genomic regions of interest, wherein the at least a subset of the nucleic acid molecules comprises digested nucleic acid molecules in the one or more partitioned sets; and
  e) determining methylation status at one or more genetic loci of the nucleic acid molecules in at least one of the partitioned sets.

Embodiment 3 is a method of analyzing nucleic acid molecules in a biological sample, comprising:
  a) partitioning at least a subset of the nucleic acid molecules in the biological sample, based on the methylation status of the nucleic acid molecules into a plurality of partitioned sets, wherein the biological sample comprises methylated nucleic acid molecules and unmethylated nucleic acid molecules and the plurality of partitioned sets comprises a first partitioned set and a second partitioned set, wherein methylated nucleic acid molecules are overrepresented in the first partitioned set relative to the second partitioned set;
  b) digesting at least a subset of the first partitioned set in the plurality of partitioned sets with at least one methylation sensitive restriction enzyme; and
  c) capturing a first target region set comprising epigenetic target regions from at least a portion of a first partitioned set, and capturing a second target region set comprising epigenetic target regions from at least a portion of the second partitioned set.

Embodiment 4 is the method of embodiment 3, wherein capturing the first target region set comprises contacting the DNA of the first partitioned set with a first set of target-specific probes, and capturing the second target region set comprises contacting the DNA of the second partitioned set with a second set of target-specific probes.

Embodiment 5 is the method of embodiment 3 or 4, further comprising determining methylation status at one or more genetic loci of the nucleic acid molecules in at least one of the partitioned sets or target region sets.

Embodiment 6 is the method of any one of the above embodiments, wherein the genomic regions of interest, the first target region set, and/or the second target region set comprise sequence-variable target regions.

Embodiment 7 is the method of any one of the above embodiments, further comprising, prior to the digesting step, attaching one or more adapters to at least one end of at least a portion of the nucleic acid molecules in the plurality of partitioned sets.

Embodiment 8 is a method for determining methylation status of nucleic acid molecules, comprising:
  a) providing a biological sample of nucleic acid molecules, wherein the nucleic acid molecules comprises methylated nucleic acid molecules and unmethylated nucleic acid molecules;
  b) partitioning at least a subset of the nucleic acid molecules in the biological sample based on the methylation status of the nucleic acid molecules into a plurality of partitioned sets;
  c) attaching one or more adapters to at least one end of the nucleic acid molecules in the plurality of partitioned sets;
  d) digesting at least a subset of the one or more partitioned sets in the plurality of partitioned sets with at least one methylation sensitive restriction enzyme;
  e) enriching at least a subset of the nucleic acid molecules in the plurality of partitioned sets for genomic regions of interest; wherein the at least a subset of the nucleic acid molecules comprises digested nucleic acid molecules in the one or more partitioned sets; and
  f) determining methylation status at one or more genetic loci of the nucleic acid molecules in at least one of the partitioned sets.

Embodiment 9 is the method of embodiment 7 or 8, wherein adapters are attached to both ends of at least a portion of the nucleic acid molecules in the plurality of partitioned sets.

Embodiment 10 is the method of embodiment 1, further comprising, prior to c), enriching at least a subset of the nucleic acid molecules in the plurality of partitioned sets for genomic regions of interest, wherein the at least a subset of the nucleic acid molecules comprises digested nucleic acid molecules in the one or more partitioned sets.

Embodiment 11 is the method of any one of the preceding embodiments, further comprising detecting presence or absence of cancer in the biological sample.

Embodiment 12 is the method of any one of the above embodiments, further comprising determining a level of cancer in the biological sample.

Embodiment 13 is the method of any one of the above embodiments, wherein determining the methylation status comprises sequencing at least a subset of the digested nucleic acid molecules.

Embodiment 14 is the method of any one of embodiments 7-13, wherein the one or more adapters comprises at least one tag.

Embodiment 15 is the method of any one of the above embodiments, wherein the methylation sensitive restriction enzyme selectively digests nucleic acid molecules that are unmethylated at the recognition site of the methylation sensitive restriction enzyme.

Embodiment 16 is the method of any one of the above embodiments, wherein at least a portion of nucleic acid molecules are amplified and/or sequenced after the digesting step, and nucleic acid molecules that were digested by the methylation sensitive restriction enzyme are not amplified and/or are not sequenced.

Embodiment 17 is the method of any one of the above embodiments comprising digesting at least a subset of the one or more partitioned sets in the plurality of partitioned sets with at least two methylation sensitive restriction enzymes.

Embodiment 18 is the method of embodiment 17, wherein the at least two methylation sensitive restriction enzymes consist of two methylation sensitive restriction enzymes.

Embodiment 19 is the method of embodiment 17 or 18, wherein the methylation sensitive restriction enzymes comprise or consist of BstUI and HpaII.

Embodiment 20 is the method of embodiment 17 or 18, wherein the methylation sensitive restriction enzymes comprise or consist of HhaI and AccII.

Embodiment 21 is the method of embodiment 17 or 18, wherein the at least two methylation sensitive restriction enzymes comprise or consist of three methylation sensitive restriction enzymes.

Embodiment 22 is the method of embodiment 17 or 21, wherein the methylation sensitive restriction enzymes comprise or consist of BstUI, HpaII and Hin6I.

Embodiment 23 is the method of any one of the above embodiments, wherein the methylation sensitive restriction enzyme is selected from the group consisting of AatII, AccII, AciI, Aor13HI, Aor15HI, BspT104I, BssHII, BstUI, Cfr10I, ClaI, CpoI, Eco52I, HaeII, HapII, HhaI, Hin6I, HpaII, HpyCH4IV, MluI, MspI, NaeI, NotI, NruI, NsbI, PmaCI, Psp1406I, PvuI, SacII, SalI, SmaI, and SnaBI.

Embodiment 24 is the method of any one of embodiments 7-23, wherein the one or more adapters are resistant to digestion by the methylation sensitive restriction enzymes.

Embodiment 25 is the method of embodiment 24, wherein the one or more resistant adapters comprise one or more methylated nucleotides, optionally wherein the methylated nucleotides comprise 5-methylcytosine and/or 5-hydroxymethylcytosine.

Embodiment 26 is the method of embodiment 24, wherein the one or more resistant adapters comprise one or more nucleotide analogs resistant to methylation sensitive restriction enzymes.

Embodiment 27 is the method of embodiment 24, wherein the one or more resistant adapter comprises a nucleotide sequence not recognized by methylation sensitive restriction enzymes.

Embodiment 28 is the method of any one of embodiments 14-27, wherein the tag comprises a molecular barcode.

Embodiment 29 is the method of embodiment 28, wherein the molecular barcodes attached to nucleic acid molecules in a first partitioned set of the plurality of partitioned sets are different from the molecular barcodes attached to nucleic acid molecules in a second partitioned set of the plurality of partitioned sets.

Embodiment 30 is the method of embodiments 1-29, wherein a first partitioned set of the plurality of partitioned sets is differentially tagged from a second partitioned set of the plurality of partitioned sets.

Embodiment 31 is the method of embodiment 30, wherein a first partition tag is attached to nucleic acid molecules in the first partitioned set and a second partition tag is attached to nucleic acid molecules in the second partitioned set.

Embodiment 32 is the method of any one of the above embodiments, wherein the methylated nucleic acid molecules comprise 5-methylcytosine and/or 5-hydroxymethylcytosine.

Embodiment 33 is the method of any one of embodiments 13-32, wherein the sequencing is performed by a next generation sequencer.

Embodiment 34 is the method of any one of the preceding embodiments, wherein the biological sample is selected from the group consisting of a DNA sample, an RNA sample, a polynucleotide sample, a cell-free DNA sample, and a cell-free RNA sample.

Embodiment 35 is the method of any one of the preceding embodiments, wherein the biological sample is a cell-free DNA sample.

Embodiment 36 is the method of embodiment 35, wherein the cell-free DNA is between 1 ng and 500 ng.

Embodiment 37 is the method of any one of the preceding embodiments, wherein the partitioning comprises partitioning the nucleic acid molecules based on a differential binding affinity of the nucleic acid molecules to a binding agent that preferentially binds to nucleic acid molecules comprising methylated nucleotides.

Embodiment 38 is the method of embodiment 37, wherein the binding agent is a methyl binding domain (MBD) protein.

Embodiment 39 is the method of embodiment 37, wherein the binding agent is an antibody that is specific to one or more methylated nucleotide bases.

Embodiment 40 is the method of any one of embodiments 2-39, wherein the genomic regions of interest or epigenetic target regions comprise differentially methylated regions for cancer detection.

Embodiment 41 is the method of any one of embodiments 13-40, further comprising, prior to the sequencing, amplifying at least a portion of the nucleic acid molecules.

Embodiment 42 is the method of embodiment 41, wherein primers used in the amplification comprise at least one sample index.

Embodiment 43 is the method of any one of the above embodiments, wherein the one or more genetic loci comprises a plurality of genetic loci.

Embodiment 44 is the method of embodiment 43, wherein the plurality of genetic loci comprises one or more genomic regions.

In any of the foregoing embodiments, epigenetic target regions may be captured from one or more, or each, of the partitioned sets. Any of the methods may further comprise quantifying captured epigenetic target regions, e.g., by sequencing or quantitative PCR. In some embodiments, the methods comprise capturing a first target region set comprising epigenetic target regions from at least a portion of a first partitioned set, and capturing a second target region set comprising epigenetic target regions from at least a portion of the second partitioned set. The first and second target region sets may be the same or different.

The epigenetic target regions may comprise a hypermethylation variable target region set, e.g., comprising regions having a higher degree of methylation in at least one type of tissue than the degree of methylation in cell-free DNA from a healthy subject. Any of the methods may further comprise determining a presence, absence, or likelihood of cancer based at least in part on sequences or quantities of regions in the hypermethylation variable target region set. Any of the methods may further comprise quantifying tumor DNA in the sample based at least in part on sequences or quantities of regions in the hypermethylation variable target region set.

The epigenetic target regions may comprise a hypomethylation variable target region set, e.g., comprising regions having a lower degree of methylation in at least one type of tissue than the degree of methylation in cell-free DNA from a healthy subject. Any of the methods may further comprise determining a presence, absence, or likelihood of cancer based at least in part on sequences or quantities of regions in the hypomethylation variable target region set. Any of the methods may further comprise quantifying tumor DNA in the sample based at least in part on sequences or quantities of regions in the hypomethylation variable target region set.

In any of the foregoing embodiments, sequence-variable target regions may be captured from one or more, or each, of the partitioned sets. Any of the methods may further comprise quantifying captured epigenetic target regions, e.g., by sequencing or quantitative PCR. DNA molecules corresponding to the sequence-variable target region set may be sequenced to a greater depth of sequencing than DNA molecules corresponding to the epigenetic target region set.

In any of the foregoing embodiments, capturing target region sets may comprise contacting DNA to be captured with a set of target-specific probes, whereby complexes of target-specific probes and DNA are formed. Capturing may further comprise separating the complexes from DNA not bound to target-specific probes, thereby providing captured DNA.

In any of the foregoing embodiments, DNA may amplified before a sequencing step, or DNA may be amplified before a capturing step.

In any of the foregoing embodiments, the DNA may comprise DNA obtained from a bodily fluid, optionally wherein the bodily fluid is plasma, urine, lymph, or spinal fluid. For example, the DNA may comprise cell-free DNA (cfDNA) obtained from a test subject.

In any of the foregoing embodiments, the methylation-sensitive restriction enzyme may cleave an unmethylated CpG sequence. In any of the foregoing embodiments, the methylation-sensitive restriction enzyme may be one or more of AatII, AccII, AciI, Aor13HI, Aor15HI, BspT104I, BssHII, BstUI, Cfr10I, ClaI, CpoI, Eco52I, HaeII, HapII, HhaI, Hin6I, HpaII, HpyCH4IV, MluI, NaeI, NotI, NruI, NsbI, PmaCI, Psp1406I, PvuI, SacII, SalI, SmaI, and SnaBI.

In any of the foregoing embodiments, the method may further comprise determining a likelihood that the subject has cancer. For example, wherein the sequencing may generates a plurality of sequencing reads; and the method may further comprise mapping the plurality of sequence reads to one or more reference sequences to generate mapped sequence reads, and processing the mapped sequence reads corresponding to the sequence-variable target region set and to the epigenetic target region set to determine the likelihood that the subject has cancer.

In any of the foregoing embodiments, the test subject may have been previously diagnosed with a cancer and received one or more previous cancer treatments, optionally wherein the cfDNA is obtained at one or more preselected time points following the one or more previous cancer treatments, and sequencing the captured set of cfDNA molecules, whereby a set of sequence information is produced. Such a method may further comprise detecting a presence or absence of DNA originating or derived from a tumor cell at a preselected timepoint using the set of sequence information. Such a method may further comprise determining a cancer recurrence score that is indicative of the presence or absence of the DNA originating or derived from the tumor cell for the test subject, optionally further comprising determining a cancer recurrence status based on the cancer recurrence score, wherein the cancer recurrence status of the test subject is determined to be at risk for cancer recurrence when a cancer recurrence score is determined to be at or above a predetermined threshold or the cancer recurrence status of the test subject is determined to be at lower risk for cancer recurrence when the cancer recurrence score is below the predetermined threshold. Such a method may further comprise comparing the cancer recurrence score of the test subject with a predetermined cancer recurrence threshold, wherein the test subject is classified as a candidate for a subsequent cancer treatment when the cancer recurrence score is above the cancer recurrence threshold or not a candidate for a subsequent cancer treatment when the cancer recurrence score is below the cancer recurrence threshold.

In another aspect, the present disclosure provides a system comprising a controller comprising or capable of accessing, computer readable media comprising non-transitory computer-executable instructions which, when executed by at least one electronic processor perform a method comprising: (a) partitioning at least a subset of the nucleic acid molecules in the biological sample, based on the methylation status of the nucleic acid molecules into a plurality of partitioned sets, wherein the biological sample comprises methylated nucleic acid molecules and unmethylated nucleic acid molecules; (b) digesting at least a subset of the one or more partitioned sets in the plurality of partitioned sets with at least one methylation sensitive restriction enzyme; and (c) determining methylation status at one or more genetic loci of the nucleic acid molecules in at least one of the partitioned sets. In some embodiment, the method further comprises further comprises, prior to (c), enriching at least a subset of the nucleic acid molecules in the plurality of partitioned sets for genomic regions of interest, wherein the at least a subset of the nucleic acid molecules comprises digested nucleic acid molecules in the one or more partitioned sets. In some embodiments, the method further comprises, prior to (b), attaching one or more adapters to at least one end of the nucleic acid molecules in the plurality of partitioned sets. In some embodiments, the method further comprises, prior to determining the methylation status, enriching at least one portion of the nucleic acid molecules in the plurality of partitioned sets; wherein the at least one portion of the nucleic acid molecules comprises digested nucleic acid molecules in the one or more partitioned sets.

In another aspect, the present disclosure provides a system comprising a controller comprising or capable of accessing, computer readable media comprising non-transitory computer-executable instructions which, when executed by at least one electronic processor perform a method comprising: a) providing a biological sample of nucleic acid molecules, wherein the nucleic acid molecules comprises methylated nucleic acid molecules and unmethylated nucleic acid molecules; (b) partitioning at least a subset of the nucleic acid molecules in the biological sample based on the methylation status of the nucleic acid molecules into a plurality of partitioned sets; (c) digesting at least a subset of the one or more partitioned sets in the plurality of partitioned sets with at least one methylation sensitive restriction enzyme; (d) enriching at least a subset of the nucleic acid molecules in the plurality of partitioned sets for genomic regions of interest, wherein the at least a subset of the nucleic acid molecules comprises digested nucleic acid molecules in the one or more partitioned sets; and (e) determining methylation status at one or more genetic loci of the nucleic acid molecules in at least one of the partitioned sets. In some embodiments, the method further comprises, prior to (b), attaching one or more adapters to at least one end of the nucleic acid molecules in the plurality of partitioned sets.

In another aspect, the present disclosure provides a system comprising a controller comprising or capable of accessing, computer readable media comprising non-transitory computer-executable instructions which, when executed by at least one electronic processor perform a method comprising: a) providing a biological sample of nucleic acid molecules, wherein the nucleic acid molecules comprises methylated nucleic acid molecules and unmethylated nucleic acid molecules; (b) partitioning at least a subset of the nucleic acid molecules in the biological sample based on the methylation status of the nucleic acid molecules into a plurality of partitioned sets; (c) attaching one or more adapters to at least one end of the nucleic acid molecules in the plurality of partitioned sets; (d) digesting at least a subset of the one or more partitioned sets in the plurality of partitioned sets with at least one methylation sensitive restriction enzyme; (e) enriching at least a subset of the nucleic acid molecules in the plurality of partitioned sets for genomic regions of interest; wherein the at least a subset of the nucleic acid molecules comprises digested nucleic acid molecules in the one or more partitioned sets; and (f) determining methylation status at one or more genetic loci of the nucleic acid molecules in at least one of the partitioned sets.

In another aspect, the present disclosure provides a method for determining methylation status of nucleic acid molecules, comprising: (a) providing a biological sample of nucleic acid molecules, wherein the nucleic acid molecules comprises methylated nucleic acid molecules and unmethylated nucleic acid molecules; (b) partitioning at least a subset of the nucleic acid molecules in the biological sample based on the methylation status of the nucleic acid molecules into a plurality of partitioned sets; (c) attaching one or more adapters to at least one end of the nucleic acid molecules in the plurality of partitioned sets; (d) digesting at least a subset of the one or more partitioned sets in the plurality of partitioned sets with at least one methylation sensitive restriction enzyme; (e) enriching at least a subset of the nucleic acid molecules in the plurality of partitioned sets for genomic regions of interest; wherein the at least a subset of the nucleic acid molecules comprises digested nucleic acid molecules in the one or more partitioned sets; and (f) determining methylation status at one or more genetic loci of the nucleic acid molecules in at least one of the partitioned sets.

In another aspect, the present disclosure provides a method for determining methylation status of nucleic acid molecules, comprising: (a) providing a biological sample of nucleic acid molecules, wherein the nucleic acid molecules comprises methylated nucleic acid molecules and unmethylated nucleic acid molecules; (b) partitioning at least a subset of the nucleic acid molecules in the biological sample based on the methylation status of the nucleic acid molecules into a plurality of partitioned sets; (c) digesting at least a subset of the one or more partitioned sets in the plurality of partitioned sets with at least one methylation sensitive restriction enzyme; (d) enriching at least a subset of the nucleic acid molecules in the plurality of partitioned sets for genomic regions of interest, wherein the at least a subset of the nucleic acid molecules comprises digested nucleic acid molecules in the one or more partitioned sets; and (e) determining methylation status at one or more genetic loci of the nucleic acid molecules in at least one of the partitioned sets. In some embodiments, the method further comprises, prior to (b), attaching one or more adapters to at least one end of the nucleic acid molecules in the plurality of partitioned sets.

In some embodiments, the method further comprises detecting presence or absence of cancer in the biological sample. In some embodiments, the method further comprises determining a level of cancer in the biological sample, for example, by determining a level of DNA from cancer cells in the biological sample. In some embodiments, determining the methylation status comprises sequencing at least a subset of the digested nucleic acid molecules. In some embodiments, the sequencing is performed by a next generation sequencer. In some embodiments, the one or more adapters comprises at least one tag. In some embodiments, the adapter is resistant to digestion by the methylation sensitive restriction enzymes. In some embodiments, the adapter comprises one or more methylated nucleotides (e.g., nucleotides comprising a methylated base). In some embodiments, the adapter comprises one or more nucleotide analogs resistant to methylation sensitive restriction enzymes (e.g., nucleotide analogs with a linkage modification, such as phosphorothioate). In some embodiments, the adapter comprises a nucleotide sequence not recognized by methylation sensitive restriction enzymes. In some embodiments, the adapter does not comprise any sequence recognized by methylation sensitive restriction enzymes used in the method. In some embodiments, the tag comprises molecular barcode. In some embodiments, the molecular barcodes attached to nucleic acid molecules in a first partitioned set is different from the molecular barcodes attached to nucleic acid molecules in a second partitioned set. In some embodiments, a first partitioned set is differentially tagged with respect to a second partitioned set. In some embodiments, a first partition tag is attached to nucleic acid molecules in a first partitioned set and a second partition tag is attached to nucleic acid molecules in a second partitioned set.

In some embodiments, the method comprises digesting at least a subset of the one or more partitioned sets in the plurality of partitioned sets with at least two methylation sensitive restriction enzymes (MSREs). As used herein, reference to two (or more) MSREs means that two (or more) different MSREs with different properties (e.g., different recognition sequences) are used. In some embodiments, the at least two methylation sensitive restriction enzymes consist of two methylation sensitive restriction enzymes. In some embodiments, the two methylation sensitive restriction enzymes comprise BstUI and HpaII. In some embodiments, the two methylation sensitive restriction enzymes comprise HhaI and AccII. In some embodiments, the at least two methylation sensitive restriction enzymes comprise three methylation sensitive restriction enzymes. In some embodiments, the three methylation sensitive restriction enzymes comprise BstUI, HpaII and Hin6I. In some embodiments, the methylation sensitive restriction enzyme is selected from the group consisting of AatII, AccII, AciI, Aor13HI, Aor15HI, BspT104I, BssHII, BstUI, Cfr10I, ClaI, CpoI, Eco52I, HaeII, HapII, HhaI, Hin6I, HpaII, HpyCH4IV, MluI, MspI, NaeI, NotI, NruI, NsbI, PmaCI, Psp1406I, PvuI, SacII, SalI, SmaI, and SnaBI. In some embodiments, at least one MSRE selectively digests unmethylated nucleic acid molecules. In some embodiments, at least one MSRE selectively digests methylated nucleic acid molecules.

In some embodiments, the methylated nucleotides comprise 5-methylcytosine and/or 5-hydroxymethylcytosine. In some embodiments, the biological sample is selected from the group consisting of a DNA sample, an RNA sample, a polynucleotide sample, a cell-free DNA sample, and a cell-free RNA sample. In some embodiments, the biological sample is a cell-free DNA sample. In some embodiments, the cell-free DNA is between 1 ng and 500 ng.

In some embodiments, the partitioning comprises partitioning the nucleic acid molecules based on a differential binding affinity of the nucleic acid molecules to a binding agent that preferentially binds to nucleic acid molecules comprising methylated nucleotides (e.g., nucleotides comprising a methylated base). In some embodiments, the binding agent is a methyl binding domain (MBD) protein. In some embodiments, the binding agent is an antibody that is specific to one or more methylated nucleotide bases. In some embodiments, the genomic regions of interest comprise differentially methylated regions for cancer detection.

In some embodiments, the method comprises further comprises, prior to the sequencing, amplifying at least a portion of the nucleic acid molecules (e.g., after the digesting step, or after the enriching or capturing step). In some embodiments, the primers used in the amplification comprise at least one sample index. In some embodiments, nucleic acid molecules digested by a MSRE are not amplified. In some such embodiments, essentially all nucleic acid molecules in a sample are amplified except the nucleic acid molecules digested by a MSRE.

In some embodiments, the one or more genetic loci comprises plurality of genetic loci. In some embodiments, the plurality of genetic loci comprises one or more genomic regions.

In some embodiments, the method comprises digesting at least a subset of the one or more partitioned sets in the plurality of partitioned sets with at least two methylation sensitive restriction enzymes. In some embodiments, the at least two methylation sensitive restriction enzymes consist of two methylation sensitive restriction enzymes. In some embodiments, the two methylation sensitive restriction enzymes comprise BstUI and HpaII. In some embodiments, the two methylation sensitive restriction enzymes comprise HhaI and AccII. In some embodiments, the at least two methylation sensitive restriction enzymes comprise three methylation sensitive restriction enzymes. In some embodiments, the three methylation sensitive restriction enzymes comprise BstUI, HpaII and Hin6I. In some embodiments, the methylation sensitive restriction enzyme is selected from the group consisting of AatII, AccII, AciI, Aor13HI, Aor15HI, BspT104I, BssHII, BstUI, Cfr10I, ClaI, CpoI, Eco52I, HaeII, HapII, HhaI, Hin6I, HpaII, HpyCH4IV, MluI, MspI, NaeI, NotI, NruI, NsbI, PmaCI, Psp1406I, PvuI, SacII, SalI, SmaI, and SnaBI. In some embodiments, at least one MSRE selectively digests unmethylated nucleic acid molecules. In some embodiments, at least one MSRE selectively digests methylated nucleic acid molecules.

In some embodiments of each and every aspect of the invention, the results of the systems and/or methods disclosed herein are used as an input to generate a report. The report may be in a paper or electronic format. For example, information on the presence or absence of cancer, as determined by the methods or systems disclosed herein, can be displayed in such a report. Alternatively or additionally, the report may comprise information relating to the epigenetic rates of the epigenetic features, for example whether they are above or below the adjusted epigenetic rate threshold. The methods or systems disclosed herein may further comprise a step of communicating the report to a third party, such as the subject from whom the sample derived or a health care practitioner.

The various steps of the methods disclosed herein, or the steps carried out by the systems disclosed herein, may be carried out at the same time or different times, and/or in the same geographical location or different geographical locations, e.g. countries. The various steps of the methods disclosed herein can be performed by the same person or different people.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The accompanying drawings, which are incorporated in and constitute a part of this specification, illustrate certain embodiments, and together with the written description, serve to explain certain principles of the methods, computer readable media, and systems disclosed herein. The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

FIG. 1 shows one type of MSRE, which selectively digests recognition sites comprising unmethylated nucleotides and generally does not digest recognition sites comprising methylated nucleotides.

FIGS. 8A and 8C correspond to a first donor and FIGS. 8B and 8D correspond to a second donor. Data points are distributed along the horizontal axis for readability.

FIGS. 10A-J show hypomethylation variable target region ("Hypo VTR") molecule counts (10A-E) or Hypo VTR/ negative control molecule ratios (10F-J) for the indicated conditions as described in Example 5. Data points are distributed along the horizontal axis for readability. Triangles, circles, plus signs, and squares indicate that the source of the normal cfDNA was the first, second, third, or fourth of four healthy donors, respectively.

DEFINITIONS

Figure 1:
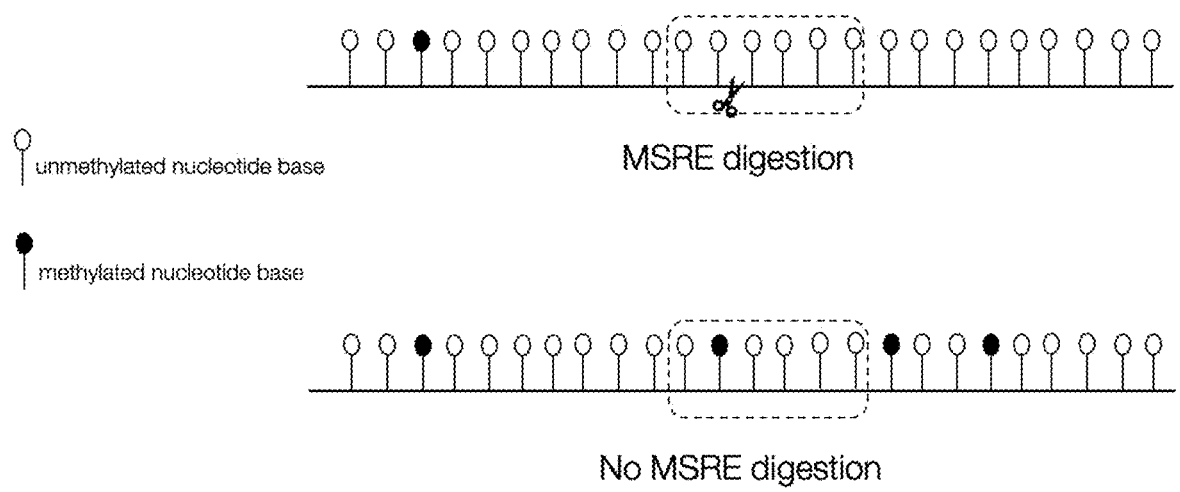
FIG. 1 is a schematic diagram of a methylation sensitive restriction enzyme (MSRE) digesting/cleaving the DNA as the restriction enzyme (RE) recognition site contains unmethylated nucleotides (top) and a schematic diagram of a methylation sensitive restriction enzyme (MSRE) not cleaving the DNA as the restriction enzyme (RE) recognition site contains a methylated nucleotide (bottom). Thus.

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent upon reading this disclosure and so forth.

It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this disclosure pertains. In describing and claiming the methods, computer readable media, and systems, the following terminology, and grammatical variants thereof, will be used in accordance with the definitions set forth below.

About: As used herein, "about" or "approximately" as applied to one or more values or elements of interest, refers to a value or element that is similar to a stated reference value or element. In certain embodiments, the term "about" or "approximately" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Adapter: As used herein, "adapter" refers to a short nucleic acid (e.g., less than about 500 nucleotides, less than about 100 nucleotides, or less than about 50 nucleotides in length) that is typically at least partially double-stranded and is attached to either one end or both ends (i.e., two adapters are attached to both ends of the nucleic acid—one adapter at end of the nucleic acid) of a given sample nucleic acid molecule. Adapters can include nucleic acid primer binding sites to permit amplification of a nucleic acid molecule flanked by adapters at both ends, and/or a sequencing primer binding site, including primer binding sites for sequencing applications, such as various next-generation sequencing (NGS) applications. Adapters can also include binding sites for capture probes, such as an oligonucleotide attached to a flow cell support or the like. Adapters can also include a nucleic acid tag as described herein. Nucleic acid tags are typically positioned relative to amplification primer and sequencing primer binding sites, such that a nucleic acid tag is included in amplicons and sequence reads of a given nucleic acid molecule. Adapters of the same or different sequences can be linked to the respective ends of a nucleic acid molecule. In some embodiments, the adapters of the same sequence is linked to the respective ends of the nucleic acid molecule except that the nucleic acid tag differs. In some embodiments, the adapter is a Y-shaped adapter in which one end is blunt ended or tailed as described herein, for joining to a nucleic acid molecule, which is also blunt ended or tailed with one or more complementary nucleotides and the other end of the Y-shaped adapter comprises a non-complementary sequence which does not hybridize to form a double-strand. In still other example embodiments, an adapter is a bell-shaped adapter that includes a blunt or tailed end for joining to a nucleic acid molecule to be analyzed. Other examples of adapters include T-tailed and C-tailed adapters.

Amplify: As used herein, "amplify" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. Amplification includes but is not limited to polymerase chain reaction (PCR).

Barcode: As used herein, "barcode" in the context of nucleic acids refers to a nucleic acid molecule comprising a sequence that can serve as a identifier. For example, the barcode can serve as an identifier of the molecule (i.e., molecular barcode), an identifier of the sample (i.e., sample barcode) or an identifier of the partition (i.e., partition barcode). The individual "barcode" sequences are typically added to each DNA fragment during next-generation sequencing (NGS) library preparation so that each read can be identified and sorted before the final data analysis.

Cancer Type: As used herein, "cancer type" refers to a type or subtype of cancer defined, e.g., by histopathology. Cancer type can be defined by any conventional criterion, such as on the basis of occurrence in a given tissue (e.g., blood cancers, central nervous system (CNS), brain cancers, lung cancers (small cell and non-small cell), skin cancers, nose cancers, throat cancers, liver cancers, bone cancers, lymphomas, pancreatic cancers, bowel cancers, rectal cancers, thyroid cancers, bladder cancers, kidney cancers, mouth cancers, stomach cancers, breast cancers, prostate cancers, ovarian cancers, lung cancers, intestinal cancers, soft tissue cancers, neuroendocrine cancers, gastroesophageal cancers, head and neck cancers, gynecological cancers, colorectal cancers, urothelial cancers, solid state cancers, heterogeneous cancers, homogenous cancers), unknown primary origin and the like, and/or of the same cell lineage (e.g., carcinoma, sarcoma, lymphoma, cholangiocarcinoma, leukemia, mesothelioma, melanoma, or glioblastoma) and/or cancers exhibiting cancer markers, such as, but not limited to, Her2, CA15-3, CA19-9, CA-125, CEA, AFP, PSA, HCG, hormone receptor and NMP-22. Cancers can also be classified by stage (e.g., stage 1, 2, 3, or 4) and whether of primary or secondary origin.

Captured set: As used herein, a "captured set" of nucleic acids refers to nucleic acids that have undergone capture.

Capturing: As used herein, "capturing" or "enriching" one or more target nucleic acids refers to preferentially isolating or separating the one or more target nucleic acids from non-target nucleic acids.

Cell-Free Nucleic Acid: As used herein, "cell-free nucleic acid" refers to nucleic acids not contained within or otherwise bound to a cell or, in some embodiments, nucleic acids remaining in a sample following the removal of intact cells. Cell-free nucleic acids can include, for example, all non-encapsulated nucleic acids sourced from a bodily fluid (e.g., blood, plasma, serum, urine, cerebrospinal fluid (CSF), etc.) from a subject. Cell-free nucleic acids include DNA (cfDNA), RNA (cfRNA), and hybrids thereof, including genomic DNA, mitochondrial DNA, circulating DNA, siRNA, miRNA, circulating RNA (cRNA), tRNA, rRNA, small nucleolar RNA (snoRNA), Piwi-interacting RNA (piRNA), long non-coding RNA (long ncRNA), and/or fragments of any of these. Cell-free nucleic acids can be double-stranded, single-stranded, or a hybrid thereof. A cell-free nucleic acid can be released into bodily fluid through secretion or cell death processes, e.g., cellular necrosis, apoptosis, or the like. Some cell-free nucleic acids are released into bodily fluid from cancer cells, e.g., circulating tumor DNA (ctDNA). Others are released from healthy cells. CtDNA can be non-encapsulated tumor-derived fragmented DNA. A cell-free nucleic acid can have one or more epigenetic modifications, for example, a cell-free nucleic acid can be acetylated, 5-methylated, and/or hydroxy methylated.

Cellular Nucleic Acids: As used herein, "cellular nucleic acids" means nucleic acids that are disposed within one or more cells from which the nucleic acids have originated, at least at the point a sample is taken or collected from a subject, even if those nucleic acids are subsequently removed (e.g., via cell lysis) as part of a given analytical process.

Corresponding to a target region set: As used herein, "corresponding to a target region set" means that a nucleic acid, such as cfDNA, originated from a locus in the target region set or specifically binds one or more probes for the target-region set.

Coverage: As used herein, the terms "coverage", "total molecule count", or "total allele count" are used interchangeably. They refer to the total number of DNA molecules at a particular genomic position in a given sample.

Deoxyribonucleic Acid or Ribonucleic Acid: As used herein, "deoxyribonucleic acid" or "DNA" refers to a natural or modified nucleotide which has a hydrogen group at the 2'-position of the sugar moiety. DNA typically includes a chain of nucleotides comprising four types of nucleotide bases; adenine (A), thymine (T), cytosine (C), and guanine (G). As used herein, "ribonucleic acid" or "RNA" refers to a natural or modified nucleotide which has a hydroxyl group at the 2'-position of the sugar moiety. RNA typically includes a chain of nucleotides comprising four types of nucleotide bases; A, uracil (U), G, and C. As used herein, the term "nucleotide" refers to a natural nucleotide or a modified nucleotide. Certain pairs of nucleotides specifically bind to one another in a complementary fashion (called complementary base pairing). In DNA, adenine (A) pairs with thymine (T) and cytosine (C) pairs with guanine (G). In RNA, adenine (A) pairs with uracil (U) and cytosine (C) pairs with guanine (G). When a first nucleic acid strand binds to a second nucleic acid strand made up of nucleotides that are complementary to those in the first strand, the two strands bind to form a double strand. As used herein, "sequencing data," "nucleic acid sequencing information," "sequence information," "nucleic acid sequence," "nucleotide sequence", "genomic sequence," "sequence read" or "sequencing read" denotes any information or data that is indicative of the order and identity of the nucleotide bases (e.g., adenine, guanine, cytosine, and thymine or uracil) in a molecule (e.g., a whole genome, whole transcriptome, exome, oligonucleotide, polynucleotide, or fragment) of a nucleic acid such as DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, and electronic signature-based systems.

Digestion efficiency: As used herein, "digestion efficiency" or "cutting efficiency" refers to the efficiency of restriction enzyme digestion. The digestion efficiency can be calculated based on the number of control molecules observed upon digesting with restriction enzyme and number of control molecules observed in the absence of restriction enzyme digestion. The MSRE digestion efficiency can be calculated by: Efficiency=1−(number of negative control molecules$_{[MSRE]}$/number of negative control molecules$_{[Mock]}$). The MDRE (an MSRE that preferentially cleaves methylated DNA, also referred to as a methylation-dependent restriction enzyme) digestion efficiency can be calculated by: Efficiency=1−(number of positive control molecules$_{[MDRE]}$/number of positive control molecules$_{[Mock]}$).

DNA sequence: As used herein, "DNA sequence" or "sequence" refers to "raw sequence reads" and/or "consensus sequences." Raw sequence reads are the output of a DNA sequencer, and typically include redundant sequences of the same parent molecule, for example after amplification. "Consensus sequences" are sequences derived from redundant sequences of a parent molecule intended to represent the sequence of the original parent molecule. Consensus sequences includes the base identity at a single position. In some embodiments, consensus sequence can represent a single nucleotide base at a particular genomic position. In some embodiments, consensus sequence can represent a string of nucleotide bases at a plurality of genomic positions. Consensus sequences can be produced by voting (wherein each majority nucleotide, e.g., the most commonly observed nucleotide at a given base position, among the sequences is the consensus nucleotide) or other approaches such as comparing to a reference genome. Consensus sequences can be produced by tagging original parent molecules with unique or non-unique molecular tags, which allow tracking of the progeny sequences (e.g., after amplification) by tracking of the tag and/or use of sequence read internal information. Examples of tagging or barcoding, and uses of tags or barcodes, are provided in, for example, U.S. Patent Pub. Nos. 2015/0368708, 2015/0299812, 2016/0040229, and 2016/0046986, each of which is entirely incorporated herein by reference.

Enriched sample: As used herein, "enriched sample" refers to a sample that has been enriched for specific regions of interest. The sample can be enriched by amplifying regions of interest or by using single-stranded DNA/RNA probes or double stranded DNA probes that can hybridize to nucleic acid molecules of interest (e.g., SureSelect® probes, Agilent Technologies). In some embodiments, an enriched sample refers to a subset or portion of the processed sample that is enriched, where the subset or portion of the processed sample being enriched contains nucleic acid molecules from a sample of cell-free polynucleotides or polynucleotides.

Epigenetic characteristic: As used herein, "epigenetic characteristic" refers to any directly observable measure of the DNA molecule that can be used in the analysis of the epigenetic feature of that DNA molecule. For example, if the epigenetic feature is methylation, then the epigenetic characteristic of the DNA molecule can refer to, but not limited to, the partitioning of the DNA molecule, number of CpG residues in the DNA molecule and the location (or offset) of the DNA molecule. For example, if the epigenetic feature is fragmentomic signal, then the epigenetic characteristics can be, but not limited to, length of the cfDNA molecules, the location (or offset) of the cfDNA molecule—start and/or end positions of the cfDNA molecules.

Epigenetic feature: As used herein, "epigenetic feature" refers to any parameter that may manifest a non-sequence modification of nucleic acids and also includes chromatin modifications. These modifications do not change the sequence of the DNA. The epigenetic features can include, but not limited to, methylation state; fragmentomic signal; position/distribution of nucleosome, CTCF proteins, transcription start sites, regulatory proteins and any other proteins that may bind to the DNA.

Epigenetic target region set: As used herein, "epigenetic target region set" refers to a set of target regions that may manifest non-sequence modifications in neoplastic cells (e.g., tumor cells and cancer cells) and non-tumor cells (e.g., immune cells, cells from tumor microenvironment). These modifications do not change the sequence of the DNA. Examples of non-sequence modifications changes include, but not limited to, changes in methylation (increases or decreases), nucleosome distribution, CTCF binding, transcription start sites, regulatory protein binding regions and any other proteins that may bind to the DNA. For present purposes, loci susceptible to neoplasia-, tumor-, or cancer-associated focal amplifications and/or gene fusions may also be included in an epigenetic target region set because detection of a change in copy number by sequencing or a fused sequence that maps to more than one locus in a reference genome tends to be more similar to detection of exemplary epigenetic changes discussed above than detection of nucleotide substitutions, insertions, or deletions, e.g., in that the focal amplifications and/or gene fusions can be detected at a relatively shallow depth of sequencing because their detection does not depend on the accuracy of base calls at one or a few individual positions. For example, the epigenetic target region set can comprise a set of target regions for analyzing the fragment length or fragment end point location distribution. In some embodiments, the epigenetic target region set includes one or more genomic regions, where the epigenetic state (e.g., methylation state) of cfDNA molecules in these regions is unchanged in cancer, but their presence/quantity in blood indicates increased, aberrant presentation of cfDNA from certain tissue (e.g. cancer origin) into circulation. The terms "epigenetic" and "epigenomic" are used interchangeably herein.

Fragmentomic signal: As used herein, "fragmentomic signal" refers to the distribution of the cfDNA fragment sizes and cfDNA fragment positions at a particular genomic region. Fragmentomic signal can include, but not limited to, cfDNA fragment lengths, start and/or end positions of the cfDNA molecule (fragments' size coverage). Fragmentomic signal can also include the frequency at which a DNA molecule endpoint occurs at genomic location (at a specific position or region of interest surrounding the specific position). Fragmentomic signal can also include the nucleosomal positioning of DNA molecules. In some embodiments, the fragmentomic signal includes DNA molecule's endpoint information, but does not necessarily include a length parameter of the DNA molecule).

Genomic region: As used herein, "genomic region" refers to any region (e.g., range of base pair locations) of a genome, e.g., a chromosome, a chromosome arm, a gene, or an exon. A genomic region may be a contiguous or a non-contiguous region. A "genetic locus" (or "locus") can be a portion or entirety of a genomic region (e.g., a gene, a portion of a gene, or a single nucleotide of a gene). In some embodiments, the size of the genomic region comprises up to a length of a chromosome/chromosome arm or a topologically associated domain (TAD). In some embodiments, the size of the genomic region can be limited to the biological activity of the region (e.g., transcriptional unit or regulatory unit).

Hypermethylation: As used herein, "hypermethylation" refers to an increased level or degree of methylation of nucleic acid molecule(s) relative to the other nucleic acid molecules within a population (e.g., sample) of nucleic acid molecules. In some embodiments, hypermethylation refers to an increased level or degree of methylation of nucleic acid molecule(s) from a particular genomic region in tumor samples relative to the degree of methylation of nucleic acid molecules form the same genomic region in non-tumor samples. In some embodiments, hypermethylated DNA can include DNA molecules comprising at least 1 methylated residue, at least 2 methylated residues, at least 3 methylated residues, at least 5 methylated residues, at least 10 methylated residues, at least 20 methylated residues, at least 25 methylated residues, or at least 30 methylated residues.

Hypomethylation: As used herein, "hypomethylation" refers to a decreased level or degree of methylation of nucleic acid molecule(s) relative to the other nucleic acid molecules within a population (e.g., sample) of nucleic acid molecules. In some embodiments, hypomethylated DNA includes unmethylated DNA molecules. In some embodiments, hypomethylation refers to an decreased level or degree of methylation of nucleic acid molecule(s) from a particular genomic region in tumor samples relative to the degree of methylation of nucleic acid molecules form the same genomic region in non-tumor samples. In some embodiments, hypomethylated DNA can include DNA molecules comprising 0 methylated residues, at most 1 methylated residue, at most 2 methylated residues, at most 3 methylated residues, at most 4 methylated residues, or at most 5 methylated residues.

Methylation: As used herein, "methylation" or "DNA methylation" can refer to the presence of a methyl group to the cytosine at a CpG site (cytosine-phosphate-guanine site—i.e., a cytosine followed by a guanine in a 5'→3' direction of the nucleic acid sequence). In some embodiments, DNA methylation comprises addition of a methyl group to adenine, such as in $N^6$-methyladenine. In some embodiments, DNA methylation is 5-methylation (modification of the 5th carbon of the 6-carbon ring of cytosine). In some embodiments, 5-methylation comprises addition of a methyl group to the 5C position of the cytosine to create 5-methylcytosine (m5c). In some embodiments, methylation comprises a derivative of m5c. Derivatives of m5c include, but are not limited to, 5-hydroxymethylcytosine (5-hmC), 5-formylcytosine (5-fC), and 5-caryboxylcytosine (5-caC). In some embodiments, DNA methylation is 3C methylation (modification of the 3rd carbon of the 6-carbon ring of cytosine). In some embodiments, 3C methylation comprises addition of a methyl group to the 3C position of the cytosine to generate 3-methylcytosine (3mC). Methylation can also occur at non CpG sites, for example, methylation can occur at a CpA, CpT, or CpC site. DNA methylation can change the activity of methylated DNA region. For example, when DNA in a promoter region is methylated, transcription of the gene may be repressed. DNA methylation is critical for normal development and abnormality in methylation may disrupt epigenetic regulation. The disruption, e.g., repression, in epigenetic regulation may cause diseases, such as cancer. Promoter methylation in DNA may be indicative of cancer.

Methylation sensitive restriction enzyme (MSRE): As used herein, "methylation sensitive restriction enzyme" or "MSRE" refers to a restriction enzyme that is sensitive to the methylation status of the DNA (e.g. cytosine methylation) i.e., the presence or absence of methyl group in a nucleotide base alters the rate at which the enzyme cleaves the target DNA. In some embodiments, the methylation sensitive restriction enzymes do not cleave the DNA if a particular nucleotide base is methylated at the recognition sequence. For example, HpaII is a methylation sensitive restriction enzyme with a recognition sequence "CCGG" and it does not cleave DNA if the second cytosine in the recognition sequence is methylated. In some embodiments, the methylation sensitive restriction enzymes cleave the DNA if a particular nucleotide base is methylated at the recognition sequence. For example, SgeI is a methylation sensitive restriction enzyme with a recognition sequence "$^{5m}$CNNG $(N)_9$," and it cleaves DNA if the cytosine in the recognition sequence is methylated ($^{5m}$C). As another example, FspEI is a methylation sensitive restriction enzyme with a recognition sequence "$C^{5m}C(N)_{12}$" and it cleaves DNA if the indicated cytosine in the recognition sequence is methylated ($^{5m}$C). FIG. 1 is a schematic diagram of a methylation sensitive restriction enzyme (MSRE) digesting/cleaving the DNA as the restriction enzyme (RE) recognition site contains unmethylated nucleotides (top) and a schematic diagram of a methylation sensitive restriction enzyme (MSRE) not cleaving the DNA as the restriction enzyme (RE) recognition site (dashed box) contains a methylated nucleotide (bottom) at a position that affects activity of the MSRE. In some embodiments, the enzymatic activity of a MSRE is at least 10, 20, 50, or 100-fold higher on a methylated recognition site relative to an unmethylated version of the same recognition site. In some embodiments, the enzymatic activity of a MSRE is at least 10, 20, 50, or 100-fold higher on an unmethylated recognition site relative to a methylated version of the same recognition site.

Methylation status: As used herein, "methylation status" can refer to the presence or absence of methyl group on a DNA base (e.g. cytosine) at a particular genomic position in a nucleic acid molecule. It can also refer to the degree of methylation in a nucleic acid sequence (e.g., highly methylated, low methylated, intermediately methylated or unmethylated nucleic acid molecules). The methylation status can also refer to the number of nucleotides methylated in a particular nucleic acid molecule.

Mutation: As used herein, "mutation" refers to a variation from a known reference sequence and includes mutations such as, for example, single nucleotide variants (SNVs), and insertions or deletions (indels). A mutation can be a germline or somatic mutation. In some embodiments, a reference sequence for purposes of comparison is a wildtype genomic sequence of the species of the subject providing a test sample, typically the human genome.

Neoplasm: As used herein, the terms "neoplasm" and "tumor" are used interchangeably. They refer to abnormal growth of cells in a subject. A neoplasm or tumor can be benign, potentially malignant, or malignant. A malignant tumor is a referred to as a cancer or a cancerous tumor.

Next-Generation Sequencing: As used herein, "next-generation sequencing" or "NGS" refers to sequencing technologies having increased throughput as compared to traditional Sanger- and capillary electrophoresis-based approaches, for example, with the ability to generate hundreds of thousands of relatively small sequence reads at a time. Some examples of next-generation sequencing techniques include, but are not limited to, sequencing by synthesis, sequencing by ligation, and sequencing by hybridization. In some embodiments, next-generation sequencing includes the use of instruments capable of sequencing single molecules. Example of commercially available instruments for performing next-generation sequencing include, but are not limited to, NextSeq, HiSeq, NovaSeq, MiSeq, Ion PGM and Ion GeneStudio S5.

Nucleic Acid Tag: As used herein, "nucleic acid tag" refers to a short nucleic acid (e.g., less than about 500 nucleotides, about 100 nucleotides, about 50 nucleotides, or about 10 nucleotides in length), used to distinguish nucleic acids from different samples (e.g., representing a sample index), distinguish nucleic acids from different partitions (e.g., representing a partition tag) or different nucleic acid molecules in the same sample (e.g., representing a molecular barcode), of different types, or which have undergone different processing. The nucleic acid tag comprises a predetermined, fixed, non-random, random or semi-random oligonucleotide sequence. Such nucleic acid tags may be used to label different nucleic acid molecules or different nucleic acid samples or sub-samples. Nucleic acid tags can be single-stranded, double-stranded, or at least partially double-stranded. Nucleic acid tags optionally have the same length or varied lengths. Nucleic acid tags can also include double-stranded molecules having one or more blunt-ends, include 5' or 3' single-stranded regions (e.g., an overhang), and/or include one or more other single-stranded regions at other locations within a given molecule. Nucleic acid tags can be attached to one end or to both ends of the other nucleic acids (e.g., sample nucleic acids to be amplified and/or sequenced). Nucleic acid tags can be decoded to reveal information such as the sample of origin, form, or processing of a given nucleic acid. For example, nucleic acid tags can also be used to enable pooling and/or parallel processing of multiple samples comprising nucleic acids bearing different molecular barcodes and/or sample indexes in which the nucleic acids are subsequently being deconvolved by detecting (e.g., reading) the nucleic acid tags. Nucleic acid tags can also be referred to as identifiers (e.g. molecular identifier, sample identifier). Additionally, or alternatively, nucleic acid tags can be used as molecular identifiers (e.g., to distinguish between different molecules or amplicons of different parent molecules in the same sample or sub-sample). This includes, for example, uniquely tagging different nucleic acid molecules in a given sample, or non-uniquely tagging such molecules. In the case of non-unique tagging applications, a limited number of tags (i.e., molecular barcodes) may be used to tag each nucleic acid molecule such that different molecules can be distinguished based on their endogenous sequence information (for example, start and/or stop positions where they map to a selected reference genome, a sub-sequence of one or both ends of a sequence, and/or length of a sequence) in combination with at least one molecular barcode. Typically, a sufficient number of different molecular barcodes are used such that there is a low probability (e.g., less than about a 10%, less than about a 5%, less than about a 1%, or less than about a 0.1% chance) that any two molecules may have the same endogenous sequence information (e.g., start and/or stop positions, subsequences of one or both ends of a sequence, and/or lengths) and also have the same molecular barcode.

Partitioning: As used herein, "partitioning" refers to physically separating or fractionating a mixture of nucleic acid molecules in a sample based on a characteristic of the nucleic acid molecules. The partitioning can be physical partitioning of molecules. Partitioning can involve separating the nucleic acid molecules into groups or sets based on the level of epigenetic feature (for e.g., methylation). For example, the nucleic acid molecules can be partitioned based on the level of methylation of the nucleic acid molecules. In some embodiments, the methods and systems used for partitioning may be found in PCT Patent Application No. PCT/US2017/068329, which is hereby incorporated by reference in its entirety. Following partitioning, the groups or sets of separated or fractionated nucleic acid molecules are also referred to herein as fractions, partitions, or partitioned sets.

Partitioned set: As used herein, "partitioned set" or "partition" refers to a set of nucleic acid molecules partitioned into a set or group based on the differential binding affinity of the nucleic acid molecules or proteins associated with the nucleic acid molecules to a binding agent. The binding agent binds preferentially to the nucleic acid molecules comprising nucleotides with epigenetic modification. For example, if the epigenetic modification is methylation, the binding agent can be a methyl binding domain (MBD) protein. In some embodiments, a partitioned set can comprise nucleic acid molecules belonging to a particular level or degree of epigenetic feature (for e.g., methylation). For example, the nucleic acid molecules can be partitioned into three sets— one set for highly methylated nucleic acid molecules (hyper partitioned set or hypermethylated partitioned set), a second set for low methylated nucleic acid molecules (hypo partitioned set or hypomethylated partitioned set), and a third set for intermediate methylated nucleic acid molecules (intermediate partitioned set or intermediately methylated partitioned set). In another example, the nucleic acid molecules can be partitioned based on the number of methylated nucleotides—one partitioned set can have nucleic acid molecules with nine methylated nucleotides, and another partitioned set can have unmethylated nucleic acid molecules (zero methylated nucleotides).

Polynucleotide: As used herein, "polynucleotide", "nucleic acid", "nucleic acid molecule", or "oligonucleotide" refers to a linear polymer of nucleosides (including deoxyribonucleosides, ribonucleosides, or analogs thereof) joined by inter-nucleosidic linkages. Typically, a polynucleotide comprises at least three nucleosides. Oligonucleotides often range in size from a few monomeric units, e.g., 3-4, to hundreds of monomeric units. Whenever a polynucleotide is represented by a sequence of letters, such as "ATGCCTG", the nucleotides are in 5' 3' order from left to right, and in the case of DNA, "A" denotes deoxyadenosine, "C" denotes deoxycytidine, "G" denotes deoxyguanosine, and "T" denotes deoxythymidine, unless otherwise noted. The letters A, C, G, and T may be used to refer to the bases themselves, to nucleosides, or to nucleotides comprising the bases.

Processing: As used herein, "processing" refers to a set of steps used to generate a library of nucleic acids that is suitable for sequencing. The set of steps can include, but are not limited to, partitioning, end repairing, addition of sequencing adapters, tagging, and/or PCR amplification of nucleic acids.

Quantitative measure: As used herein, "quantitative measure" refers to an absolute or relative measure. A quantitative measure can be, without limitation, a number, a statistical measurement (e.g., frequency, mean, median, standard deviation, or quantile), or a degree or a relative quantity (e.g., high, medium, and low). A quantitative measure can be a ratio of two quantitative measures. A quantitative measure can be a linear combination of quantitative measures. A quantitative measure may be a normalized measure.

Reference Sequence: As used herein, "reference sequence" refers to a known sequence used for purposes of comparison with experimentally determined sequences. For example, a known sequence can be an entire genome, a chromosome, or any segment thereof. A reference sequence can align with a single contiguous sequence of a genome or chromosome or chromosome arm or can include non-contiguous segments that align with different regions of a genome or chromosome. Examples of reference sequences include, for example, human genomes, such as, hg19 and hg38.

Restriction enzyme: As used herein, "restriction enzyme" is an enzyme that recognizes and cleaves the DNA at or near a specific recognition site.

Sample: As used herein, "sample" means anything capable of being analyzed by the methods and/or systems disclosed herein.

Sequencing: As used herein, "sequencing" refers to any of a number of technologies used to determine the sequence (e.g., the identity and order of monomer units) of a biomolecule, e.g., a nucleic acid such as DNA or RNA. Examples of sequencing methods include, but are not limited to, targeted sequencing, single molecule real-time sequencing, exon or exome sequencing, intron sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and a combination thereof. In some embodiments, sequencing can be performed by a gene analyzer such as, for example, gene analyzers commercially available from Illumina, Inc., Pacific Biosciences, Inc., or Applied Biosystems/Thermo Fisher Scientific, among many others.

Sequence Information: As used herein, "sequence information" in the context of a nucleic acid polymer means the order and identity of monomer units (e.g., nucleotides, etc.) in that polymer.

Sequence-variable target region set: As used herein "sequence-variable target region set" refers to a set of target regions that may exhibit changes in sequence such as nucleotide substitutions, insertions, deletions, or gene fusions or transpositions in neoplastic cells (e.g., tumor cells and cancer cells). In some embodiments, a nucleotide substitution is a single nucleotide variation.

Somatic Mutation: As used herein, the terms "somatic mutation" or "somatic variation" are used interchangeably. They refer to a mutation in the genome that occurs after conception. Somatic mutations can occur in any cell of the body except germ cells and accordingly, are not passed on to progeny.

Specifically binds: As used herein, "specifically binds" in the context of an probe or other oligonucleotide and a target sequence means that under appropriate hybridization conditions, the oligonucleotide or probe hybridizes to its target sequence, or replicates thereof, to form a stable probe:target hybrid, while at the same time formation of stable probe: non-target hybrids is minimized. Thus, a probe hybridizes to a target sequence or replicate thereof to a sufficiently greater extent than to a non-target sequence, to enable capture or detection of the target sequence. Appropriate hybridization conditions are well-known in the art, may be predicted based on sequence composition, or can be determined by using routine testing methods (see, e.g., Sambrook et al., Molecular Cloning, A Laboratory Manual, 2nd ed. (Cold Spring Harbor Laboratory Press, Cold Spring Harbor, NY, 1989) at §§ 1.90-1.91, 7.37-7.57, 9.47-9.51 and 11.47-11.57, particularly §§ 9.50-9.51, 11.12-11.13, 11.45-11.47 and 11.55-11.57, incorporated by reference herein).

Subject: As used herein, "subject" refers to an animal, such as a mammalian species (e.g., human) or avian (e.g., bird) species, or other organism, such as a plant. More specifically, a subject can be a vertebrate, e.g., a mammal such as a mouse, a primate, a simian or a human. Animals include farm animals (e.g., production cattle, dairy cattle, poultry, horses, pigs, and the like), sport animals, and companion animals (e.g., pets or support animals). A subject can be a healthy individual, an individual that has or is suspected of having a disease or a predisposition to the disease, or an individual in need of therapy or suspected of needing therapy. The terms "individual" or "patient" are intended to be interchangeable with "subject". For example, a subject can be an individual who has been diagnosed with having a cancer, is going to receive a cancer therapy, and/or has received at least one cancer therapy. The subject can be in remission of a cancer. As another example, the subject can be an individual who is diagnosed of having an autoimmune disease. As another example, the subject can be a female individual who is pregnant or who is planning on getting pregnant, who may have been diagnosed of or suspected of having a disease, e.g., a cancer, an auto-immune disease.

Target-region set: As used herein, "target-region set" or "set of target regions" or "target regions" or "target regions of interest" or "regions of interest" or "genomic regions of interest" refers to a plurality of genomic loci or a plurality of genomic regions targeted for capture and/or targeted by a set of probes (e.g., through sequence complementarity).

Tumor fraction: As used herein, "tumor fraction" refers to the proportion of cfDNA molecules that originated from tumor cells for a given sample, or sample-region pair.

The terms "or a combination thereof" and "or combinations thereof" as used herein refers to any and all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

"Or" is used in the inclusive sense, i.e., equivalent to "and/or," unless the context requires otherwise.

DETAILED DESCRIPTION

Certain embodiments of the invention are described herein. While the invention will be described in conjunction with such embodiments, it will be understood that they are not intended to limit the invention to those embodiments. On the contrary, the invention is intended to cover all alternatives, modifications, and equivalents, which may be included within the invention as defined by the appended claims.

Numeric ranges are inclusive of the numbers defining the range. Measured and measurable values are understood to be approximate, taking into account significant digits and the error associated with the measurement. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

The section headings used herein are for organizational purposes and are not to be construed as limiting the disclosed subject matter in any way. In the event that any document or other material incorporated by reference contradicts any explicit content of this specification, including definitions, this specification controls.

I. Overview

Cancer formation and progression may arise from both genetic modification and epigenetic features of deoxyribonucleic acid (DNA). The present disclosure provides methods and systems for analyzing DNA, such as cell-free DNA (cfDNA). The present disclosure provides methods and systems for reducing signal to noise ratio of methylation partitioning assays.

Without wishing to be bound by any particular theory, cells in or around a cancer or neoplasm may shed more DNA than cells of the same tissue type in a healthy subject. As such, the distribution of tissue of origin of certain DNA samples, such as cfDNA, may change upon carcinogenesis. Thus, for example, an increase in the level of hypermethylation variable target regions that show lower methylation in healthy cfDNA than in at least one other tissue type can be an indicator of the presence (or recurrence, depending on the history of the subject) of cancer. Similarly, an increase in the level of hypomethylation variable target regions in the sample can be an indicator of the presence (or recurrence, depending on the history of the subject) of cancer.

Additionally, cancer can be indicated by non-sequence modifications, such as methylation. Examples of methylation changes in cancer include local gains of DNA methylation in the CpG islands at the TSS of genes involved in normal growth control, DNA repair, cell cycle regulation, and/or cell differentiation. This hypermethylation can be associated with an aberrant loss of transcriptional capacity of involved genes and occurs at least as frequently as point mutations and deletions as a cause of altered gene expression. DNA methylation profiling can be used to detect regions of the genome with different extents of methylation ("differentially methylated regions" or "DMRs"), such as aberrant methylation, that arises during development or by disease, for example, cancer or any cancer-associated disease. For example, regions that are normally hypermethylated or hypomethylated in a given sample type (e.g., cfDNA from the bloodstream) but which may show an abnormal degree of methylation that correlates to a neoplasm or cancer, e.g., because of unusually increased contributions of tissues to the type of sample (e.g., due to increased shedding of DNA in or around the neoplasm or cancer) and/or from extents of methylation can be detected using DNA methylation profiling.

In some embodiments, DNA methylation comprises addition of a methyl group to a cytosine residue at a CpG site (cytosine-phosphate-guanine site (i.e., a cytosine followed by a guanine in a 5'→3' direction of the nucleic acid sequence). In some embodiments, DNA methylation comprises addition of a methyl group to an adenine residue, such as in $N^6$-methyladenine. In some embodiments, DNA methylation is 5-methylation (modification of the 5th carbon of the 6-carbon ring of cytosine). In some embodiments, 5-methylation comprises addition of a methyl group to the 5C position of the cytosine residue to create 5-methylcytosine (m5c or 5-mC or 5mC). In some embodiments, methylation comprises a derivative of m5c. Derivatives of m5c include, but are not limited to, 5-hydroxymethylcytosine (5-hmC or 5hmC), 5-formylcytosine (5-fC), and 5-caryboxylcytosine (5-caC). In some embodiments, DNA methylation is 3C methylation (modification of the 3rd carbon of the 6-carbon ring of the cytosine residue). In some embodiments, 3C methylation comprises addition of a methyl group to the 3C position of the cytosine residue to generate 3-methylcytosine (3mC). Methylation can also occur at non-CpG sites, for example, methylation can occur at a CpA, CpT, or CpC site. DNA methylation can change the activity of methylated DNA region. For example, when DNA in a promoter region is methylated, transcription of the gene may be repressed. DNA methylation is critical for normal development and abnormality in methylation may disrupt epigenetic regulation. The disruption, e.g., repression, in epigenetic regulation may cause diseases, such as cancer. Promoter methylation in DNA may be indicative of cancer.

Methylation profiling can involve determining methylation patterns across different regions of the genome. For example, after partitioning molecules based on extent of methylation (e.g., relative number of methylated nucleotides per molecule) and sequencing, the sequences of molecules in the different partitions can be mapped to a reference genome. This can show regions of the genome that, compared with other regions, are more highly methylated or are less highly methylated. In this way, genomic regions, in contrast to individual molecules, may differ in their extent of methylation.

Combining the signals obtained from methylation profiling with the signals obtained from somatic variations (e.g., SNV, indel, CNV, and gene fusions) facilitate the detection of cancer.

Nucleic acid molecules in a sample may be fractionated or partitioned based on methylation status of the nucleic acid molecules. Partitioning nucleic acid molecules in a sample can increase a rare signal. For example, a genetic variation present in hypermethylated DNA but less (or not) present in hypomethylated DNA can be more easily detected by partitioning a sample into hypermethylated and hypomethylated nucleic acid molecules. By analyzing multiple fractions of a sample, a multi-dimensional analysis of a single molecule can be performed and hence, greater sensitivity can be achieved. Partitioning may include physically partitioning nucleic acid molecules into subsets or groups based on the presence or absence of one or more methylated nucleotides (e.g., nucleotides comprising a methylated base). A sample may be fractionated or partitioned into one or more partitioned sets based on a characteristic that is indicative of differential gene expression or a disease state. A sample may be fractionated based on a characteristic, or combination thereof that provides a difference in signal between a normal and diseased state during analysis of nucleic acids, e.g., cell free DNA ("cfDNA"), non-cfDNA, tumor DNA, circulating tumor DNA ("ctDNA") and cell free nucleic acids ("cfNA").

In some embodiments, the sample can be partitioned into two or more partitioned sets (e.g. at least 3, 4, 5, 6, or 7 partitioned sets) based on the differential binding affinity of the methylated nucleic acid molecules to a binding agent (i.e., a binding agent that binds to methylated nucleotides (e.g., nucleotides comprising a methylated base)). Examples of binding agents include, but not limited to methyl binding domain (MBDs) and methyl binding proteins (MBPs). Examples of MBPs contemplated herein include, but are not limited to:

(a) MeCP2 and MBD2 are proteins preferentially binding to 5-methyl-cytosine over unmodified cytosine;
(b) RPL26, PRP8 and the DNA mismatch repair protein MHS6 preferentially bind to 5-hydroxymethyl-cytosine over unmodified cytosine;
(c) FOXK1, FOXK2, FOXP1, FOXP4, and FOXI3 preferentially bind to 5-formylcytosine over unmodified cytosine (Iurlaro et al., Genome Biol. 14, R119 (2013)); and
(d) Antibodies specific to one or more methylated nucleotide bases.

In such embodiments, nucleic acids overrepresented in a modification bind to the agent at a greater extent than nucleic acids underrepresented in the modification. Alternatively, nucleic acids having modifications may bind in an all or nothing manner. But then, various levels of modifications may be sequentially eluted from the binding agent.

For example, in some embodiments, partitioning can be binary or based on degree/level of methylation. For example, all methylated fragments can be partitioned from unmethylated fragments using methyl-binding domain proteins (e.g., MethylMiner Methylated DNA Enrichment Kit (ThermoFisher Scientific)). Subsequently, additional partitioning may involve eluting fragments having different levels of methylation by adjusting the salt concentration in a solution with the methyl-binding domain and bound fragments. As salt concentration increases, fragments having greater methylation levels are eluted.

Compared to standard methylation analysis methods (e.g. bisulfite sequencing), methylation-partitioning method is highly efficient in recovering analyte molecules and enables simultaneous detection of somatic alterations. However, as the method identifies a molecule's methylation level by partitioning, the sensitivity and specificity of the method is challenged by methylated/unmethylated molecules partitioning incorrectly (e.g. unmethylated molecules partitioning into the hyper partitioned set). This technical noise, from molecule mis-partitioning, of the methylation partitioning assay limits the performance of the assay. In order to increase the signal to noise ratio of a methylation partitioning assay, specific partitioned sets can be subjected to a methylation-sensitive restriction enzyme (RE) digestion reaction to specifically remove the incorrectly partitioned molecules. For example, methylation-sensitive restriction enzymes (MSREs), that only cleave unmethylated molecules bearing the RE recognition site, can be applied to the hyper partitioned set to selectively cleave and remove (from assay process) only the unmethylated molecules that were incorrectly partitioned. Thus, from reducing the number of unmethylated molecules in the hyper partitioned set, the sensitivity and specificity of the assay is improved, which in turn, improves the ability to detect the presence or absence of circulating tumor DNA (ctDNA).

The present disclosure provides methods and systems for improving sensitivity and specificity of the DNA methylation partitioning assays. These methods and systems can be used in various applications, such as predicting prognosis, diagnosis, monitoring, recurrence, and/or relapse of cancer.

Accordingly, in one aspect, the present disclosure provides a method for analyzing nucleic acid molecules in a biological sample, comprising: (a) partitioning at least a subset of the nucleic acid molecules in the biological sample, based on the methylation status of the nucleic acid molecules into a plurality of partitioned sets, wherein the biological sample comprises methylated nucleic acid molecules and unmethylated nucleic acid molecules; (b) digesting at least a subset of the one or more partitioned sets in the plurality of partitioned sets with at least one methylation sensitive restriction enzyme; and (c) determining methylation status at one or more genetic loci of the nucleic acid molecules in at least one of the partitioned sets.

In some embodiments, the method further comprises detecting the presence or absence of cancer in the biological sample. In some embodiments, the method comprises, determining a level of cancer in the biological sample, for example, by determining a level of DNA from cancer cells in the biological sample. In some embodiments, the method further comprises, prior to digesting, attaching one or more adapters to at least one of the end (i.e., 5' and/or 3' ends) of the nucleic acid molecules in the plurality of partitioned sets. In some embodiments, determining the methylation status comprises sequencing at least a subset of the digested nucleic acid molecules. In some embodiments, the method further comprises, prior to determining the methylation status, enriching at least a subset of the nucleic acid molecules in the plurality of partitioned sets for genomic regions of interest, wherein the at least a subset of the nucleic acid molecules comprises digested nucleic acid molecules in the one or more partitioned sets. In some such embodiments, the genomic regions of interest comprise epigenetic target region sets. In some such embodiments, the methods comprise enriching or capturing a first epigenetic target region set from at least a portion of a first partitioned set and enriching or capturing a second epigenetic target region set from at least a portion of a second partitioned set.

In another aspect, the present disclosure provides a method for determining methylation status of nucleic acid molecules, comprising: (a) providing a biological sample of nucleic acid molecules, wherein the nucleic acid molecules comprises methylated nucleic acid molecules and unmethylated nucleic acid molecules; (b) partitioning at least a subset of the nucleic acid molecules in the biological sample based on the methylation status of the nucleic acid molecules into a plurality of partitioned sets; (c) digesting at least a subset of the one or more partitioned sets in the plurality of partitioned sets with at least one methylation sensitive restriction enzyme; (d) enriching at least a subset of the nucleic acid molecules in the plurality of partitioned sets for genomic regions of interest, wherein the at least a subset of the nucleic acid molecules comprises digested nucleic acid molecules in the one or more partitioned sets; and (e) determining methylation status at one or more genetic loci of the nucleic acid molecules in at least one of the partitioned sets. In some such embodiments, the genomic regions of interest comprise epigenetic target region sets. In some such embodiments, the methods comprise enriching or capturing a first epigenetic target region set from at least a portion of a first partitioned set and enriching or capturing a second epigenetic target region set from at least a portion of a second partitioned set.

In some embodiments, the method further comprises detecting the presence or absence of cancer in the biological sample. In some embodiments, the method comprises, determining a level of cancer in the biological sample, for example, by determining a level of DNA from cancer cells in the biological sample. In some embodiments, the method further comprises, prior to digesting, attaching one or more adapters to at least one of the end (i.e., 5' and/or 3' ends) of the nucleic acid molecules in the plurality of partitioned sets. In some embodiments, determining the methylation status comprises sequencing at least a subset of the digested nucleic acid molecules.

Figure 2:
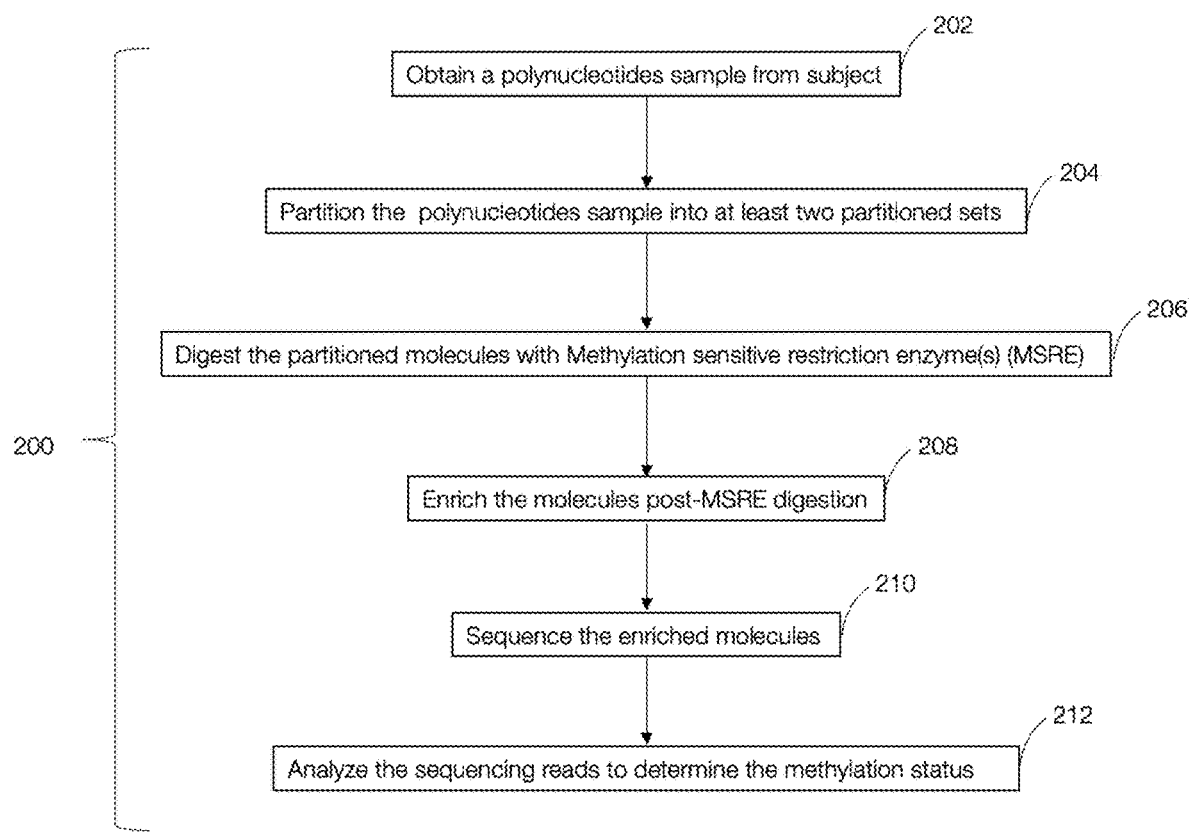
FIG. 2 is a flow chart representation of a method for determining the methylation status of nucleic acid molecules in a polynucleotide sample obtained from a subject according to an embodiment of the disclosure.

FIG. 2 illustrates an example embodiment of a method 200 for determining the methylation status of nucleic acid molecules in a polynucleotide sample obtained from a subject. In 202, a polynucleotide sample is obtained from the subject. In some embodiments, the polynucleotide sample is a DNA sample is obtained from a tumor tissue biopsy. In some embodiments, the polynucleotide sample is a cell-free DNA (cfDNA) sample obtained from blood. In 204, the polynucleotide sample is partitioned into at least two partitioned sets. In some embodiments, the partitioning comprises partitioning the nucleic acid molecules based on a differential binding affinity of the polynucleotides to a binding agent that preferentially binds to polynucleotides comprising methylated nucleotides (e.g., nucleotides comprising a methylated base). Examples of binding agents include, but are not limited to, methyl binding domain (MBDs) and methyl binding proteins (MBPs). Examples of MBPs contemplated herein are listed above.

(e) Antibodies specific to one or more methylated nucleotide bases.

Partitioning can refer to physically separating or fractionating the nucleic acid molecules based on a characteristic of the nucleic acid molecules. The partitioning can be physical partitioning of molecules. Partitioning can involve separating the nucleic acid molecules into groups or sets based on the level of methylation of the nucleic acid molecules. In some embodiments, the methods and systems used for partitioning may be performed as described by PCT Patent Application WO2018/119452, which is hereby incorporated by reference in its entirety. In those embodiments, the nucleic acids are partitioned based on the different levels of methylation (e.g., different number or frequency of methylated nucleotides (e.g., nucleotides comprising a methylated base)). In some embodiments, the nucleic acids can be partitioned into two or more partitioned sets (e.g., at least 3, 4, 5, 6, or 7 partitioned sets). For example, the nucleic acid molecules can be partitioned into three sets—one set for highly methylated nucleic acid molecules (hyper partitioned set or hypermethylated partitioned set), a second set for low methylated nucleic acid molecules (hypo partitioned set or hypomethylated partitioned set), and a third set for intermediate methylated nucleic acid molecules (intermediate partitioned set or intermediately methylated partitioned set). In some embodiments, the partitioned sets are representatives of nucleic acids having different levels of methylation (over representative or under representative of modifications). Over representation and under representation can be defined by the number of methylated nucleotides present in a DNA molecule (e.g., cfDNA molecule) relative to the median number of methylated nucleotides per strand in a population. For example, if the median number of 5-methylcytosine nucleotides in nucleic acid molecules in a sample is 2, a nucleic acid molecule including more than two 5-methylcytosine residues is over-represented and a nucleic acid with 1 or zero 5-methylcytosine residues is under-represented. The effect of the affinity separation is to enrich for nucleic acids that are over-represented in a modification (i.e., methylation level) in a bound phase and for nucleic acids that are under-represented in a modification in an unbound phase (i.e., in solution). The nucleic acids in the bound phase can be eluted before subsequent processing.

In 206, the nucleic acid molecules in at least one partitioned set are digested with at least one methylation sensitive restriction enzyme (MSRE). In some embodiments, the nucleic acids in at least one partitioned set are digested with at least two MSREs. In some embodiments, two MSREs are used for digesting the nucleic acid molecules in at least one partitioned set. In some embodiments, the two MSREs are BstUI and HpaII. In some embodiments, the two MSREs are HhaI and AccII. In some embodiments, three MSREs are used for digesting the nucleic acid molecules in at least one partitioned set. In some embodiments, the three MSREs are BstUI, HpaII and Hin6I. In some embodiments, the MSRE is selected from the group consisting of AatII, AccII, AciI, Aor13HI, Aor15HI, BspT104I, BssHII, BstUI, Cfr10I, ClaI, CpoI, Eco52I, HaeII, HapII, HhaI, Hin6I, HpaII, HpyCH4IV, MluI, MspI, NaeI, NotI, NruI, NsbI, PmaCI, Psp1406I, PvuI, SacII, SalI, SmaI, and SnaBI. In some embodiments, any commercially available MSRE can be used (MSREs provided by Takara Bio USA Inc., New England Biolabs® Inc. and/or Thermo Fisher Scientific Inc. can be used).

In some embodiments, FspEI is used for digesting the nucleic acid molecules in at least one other partitioned set (e.g., a hypomethylated partition). In some embodiments, BstUI, HpaII and Hin6I are used for digesting the nucleic acid molecules in at least one partitioned set (e.g., a hypermethylated partition) and FspEI is used for digesting the nucleic acid molecules in at least one other partitioned set (e.g., a hypomethylated partition). In embodiments involving an intermediately methylated partition, the nucleic acid molecules therein may be digested with at least one methylation sensitive restriction enzyme that preferentially cleaves methylated or unmethylated DNA. In some embodiments, the nucleic acid molecules in an intermediately methylated partition are digested with the same MSRE(s) as the hypermethylated partition. For example, the intermediately methylated partition may be pooled with the hypermethylated partition and then the pooled partitions may be subjected to digestion. In some embodiments, the nucleic acid molecules in an intermediately methylated partition are digested with the same MSRE(s) as the hypomethylated partition. For example, the intermediately methylated partition may be pooled with the hypomethylated partition and then the pooled partitions may be subjected to digestion.

In some embodiments, prior to restriction digestion with MSRE, at least one adapter is attached to at least one end of the nucleic acid molecules (i.e., 5' and/or 3' ends of the DNA molecule). In some such embodiments, adapters are attached to both ends of the nucleic acid molecules. In other embodiments, after the digestion but prior to enriching in 208, at least one adapter is attached to at least one end of the nucleic acid molecules. In some embodiments, the adapter is resistant to digestion by the methylation sensitive restriction enzymes. In some embodiments, the adapter comprises one or more methylated nucleotides (e.g., nucleotides comprising a methylated base). In some embodiments, the methylated nucleotides can be 5-methylcytosine and/or 5-hydroxymethylcytosine. In some embodiments, the adapter comprises one or more nucleotide analogs resistant to methylation sensitive restriction enzymes. In some embodiments, the adapter comprises a nucleotide sequence not recognized by methylation sensitive restriction enzymes. In some embodiments, the tags may be provided as components of adapters. In some embodiments, the tag comprises molecular barcode (i.e., molecule identifier). In some embodiments, the tag attached to nucleic acid molecules in one partitioned set is different from the tag attached to nucleic acid molecules in the other partitioned set(s). In some embodiments, one partitioned set is differentially tagged from the other partitioned set(s). Differential tagging of the partitioned sets helps in keeping track of the nucleic acid molecules belonging to a particular partitioned set. The nucleic acid molecules in different partitioned sets receive different tags that can distinguish members of one partitioned set from another. The tags linked to nucleic acid molecules of the same partition set can be the same or different from one another. But if different from one another, the tags can have part of their sequence in common so as to identify the molecules to which they are attached as being of a particular partitioned set. For example, if the molecules of the sample are partitioned into two partitioned sets—P1 and P2, then the molecules in P1 can be tagged with A1, A2, A3, and so forth, and the molecules in P2 can be tagged with B1, B2, B3, and so forth. Such a tagging system allows distinguishing the partitioned sets and between the molecules within a partitioned set. In some embodiments, the tag comprises partition tag (i.e., partition identifier). In such embodiments, the nucleic acid molecules within a partitioned set receive the same partition tag and is different from the partition tag attached to the nucleic acid molecules of the other partitioned set(s).

In 208, after MSRE digestion, the nucleic acid molecules in the one or more partitioned sets can be enriched for genomic regions of interest. In some embodiments, the genomic regions of interest can comprise differentially methylated regions for cancer detection. In 210, at least a subset of the enriched molecules is sequenced by a next generation sequencer. In 212, the sequencing reads generated by the sequencer are then analyzed using bioinformatic tools/algorithms to determine the number of molecules in the one or more partitioned sets, which in turn is used to determine the methylation status at one or more genetic loci of the nucleic acid molecules in at least one partitioned sets. In some embodiments, the one or more genetic loci can comprise multiple genetic loci. In some embodiments, the one or more genetic loci can comprise one or more genomic regions. In some embodiments, the genomic regions can be promoter region of genes. In some embodiments, prior to sequencing, the nucleic acid molecules can be amplified via PCR amplification. In some embodiments, the primers used in the amplification can comprise at least one sample index.

In some embodiments, the method can further comprise, detecting the presence or absence of cancer in the subject based on the methylation status at one or more genetic loci of the nucleic acid molecules in at least one partitioned set. In some embodiments, the method further comprises, determining a level of cancer in the polynucleotide sample, for example, by determining a level of DNA from cancer cells in the polynucleotide sample.

In another aspect, the present disclosure provides a method for determining methylation status of nucleic acid molecules, comprising: (a) providing a biological sample of nucleic acid molecules, wherein the nucleic acid molecules comprises methylated nucleic acid molecules and unmethylated nucleic acid molecules; (b) partitioning at least a subset of the nucleic acid molecules in the biological sample based on the methylation status of the nucleic acid molecules into a plurality of partitioned sets; (c) attaching one or more adapters to at least one end of the nucleic acid molecules in the plurality of partitioned sets; (d) digesting at least a subset of the one or more partitioned sets in the plurality of partitioned sets with at least one methylation sensitive restriction enzyme; (d) enriching at least a subset of the nucleic acid molecules in the plurality of partitioned sets for genomic regions of interest; wherein the at least a subset of the nucleic acid molecules comprises digested nucleic acid molecules in the one or more partitioned sets; and (e) determining methylation status at one or more genetic loci of the nucleic acid molecules in at least one of the partitioned sets. In some such embodiments, the genomic regions of interest comprise epigenetic target region sets. In some such embodiments, the methods comprise enriching or capturing a first epigenetic target region set from at least a portion of a first partitioned set and enriching or capturing a second epigenetic target region set from at least a portion of a second partitioned set.

In some embodiments, the method further comprises detecting the presence or absence of cancer in the biological sample. In some embodiments, the method comprises, determining a level of cancer in the biological sample, for example, by determining a level of DNA from cancer cells in the biological sample. In some embodiments, the method further comprises, prior to digesting, attaching one or more adapters to at least one of the end (i.e., 5' and/or 3' ends) of the nucleic acid molecules in the plurality of partitioned sets. In some embodiments, determining the methylation status comprises sequencing at least a subset of the digested nucleic acid molecules.

Figure 3:
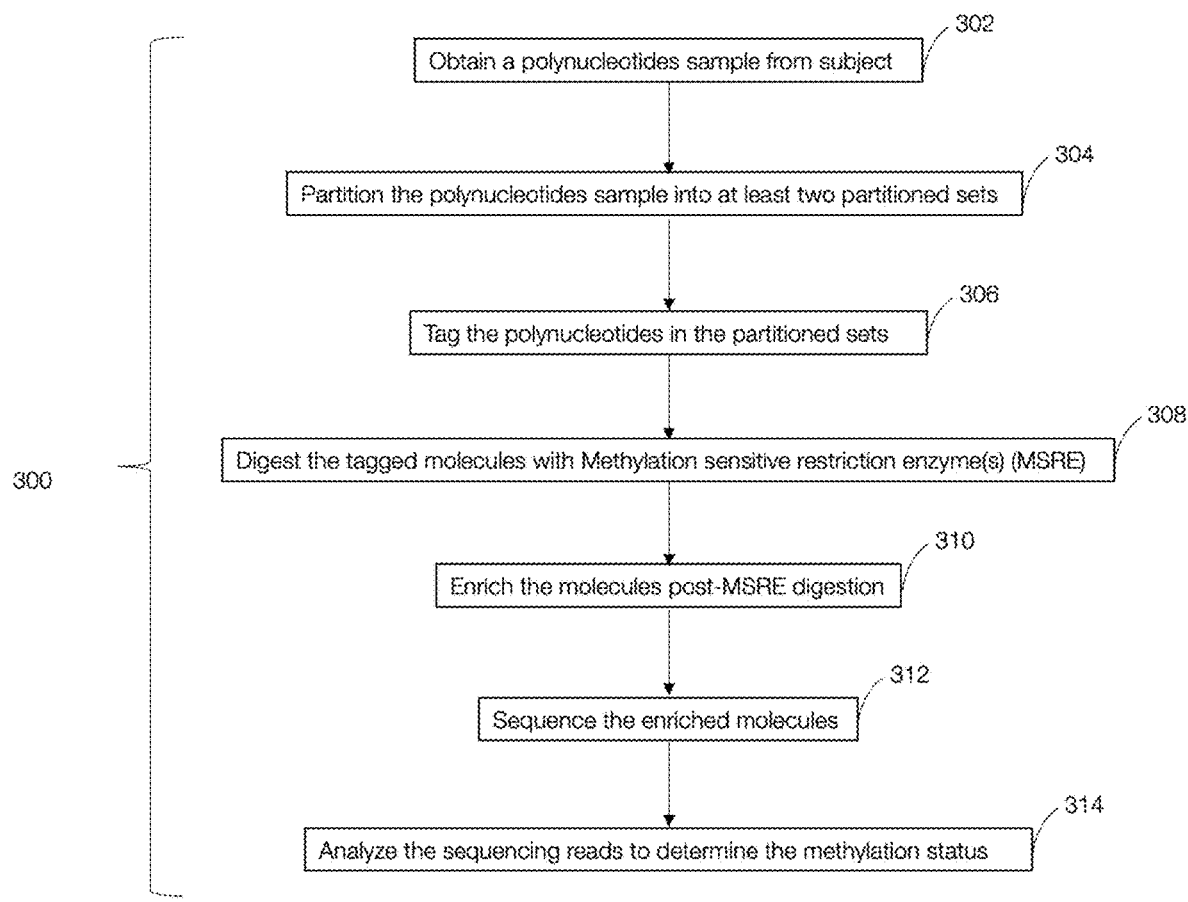
FIG. 3 is a flow chart representation of a method for detecting the presence or absence of cancer in a subject according to an embodiment of the disclosure.

FIG. 3 illustrates an example embodiment of a method 300 for detecting the presence or absence of cancer in a subject according to an embodiment of the disclosure. In 302, a polynucleotide sample is obtained from the subject. In some embodiments, the polynucleotide sample is a DNA sample is obtained from a tumor tissue biopsy. In some embodiments, the polynucleotide sample is a cell-free DNA (cfDNA) sample obtained from blood (e.g., from plasma). In 304, the polynucleotide sample is partitioned into at least two partitioned sets. In some embodiments, the partitioning comprises partitioning the nucleic acid molecules based on a differential binding affinity of the polynucleotides to a binding agent that preferentially binds to polynucleotides comprising methylated nucleotides (e.g., nucleotides comprising a methylated base). Examples of binding agents include, but are not limited to, methyl binding domain (MBDs) and methyl binding proteins (MBPs). Examples of MBPs contemplated herein are listed above.

In some embodiments, the nucleic acids can be partitioned into two or more partitioned sets (e.g., at least 3, 4, 5, 6, or 7 partitioned sets). In some embodiments, the partitioned sets are representatives of nucleic acids having different levels of methylation (over representative or under representative of modifications). For example, the nucleic acid molecules can be partitioned into three sets—one set for highly methylated nucleic acid molecules (hyper partitioned set or hypermethylated partitioned set), a second set for low methylated nucleic acid molecules (hypo partitioned set or hypomethylated partitioned set), and a third set for intermediate methylated nucleic acid molecules (intermediate partitioned set or intermediately methylated partitioned set).

In 306, the nucleic acid molecules in the one or more partitioned sets are attached with adapters, wherein the adapter comprises at least one tag and is attached to at least one end of the nucleic acid molecules (i.e., 5' and/or 3' ends of the DNA molecule). In some embodiments, the adapter is resistant to digestion by the methylation sensitive restriction enzymes. In some embodiments, the adapter comprises one or more methylated nucleotides (e.g., nucleotides comprising a methylated base). In some embodiments, the methylated nucleotides can be 5-methylcytosine and/or 5-hydroxymethylcytosine. In some embodiments, the adapter comprises one or more nucleotide analogs resistant to methylation sensitive restriction enzymes. In some embodiments, the adapter comprises a nucleotide sequence not recognized by methylation sensitive restriction enzymes. In some embodiments, the adapter does not comprise a nucleotide sequence recognized by the methylation sensitive restriction enzyme(s) used in the method. In some embodiments, the adapter comprises one or more modifications (e.g., a linkage modification, such as phosphorothioate) that inhibits cleavage by the methylation sensitive restriction enzyme(s). In some embodiments, the tags may be provided as components of adapters. In some embodiments, the tag comprises molecular barcode (i.e., molecule identifier). In some embodiments, the tag attached to nucleic acid molecules in one partitioned set is different from the tag attached to nucleic acid molecules in the other partitioned set(s). In some embodiments, one partitioned set is differentially tagged from the other partitioned set(s). Differential tagging of the partitioned sets helps in keeping track of the nucleic acid molecules belonging to a particular partitioned set. The nucleic acid molecules in different partitioned sets receive different tags that can distinguish members of one partitioned set from another. The tags linked to nucleic acid molecules of the same partition set can be the same or different from one another. But if different from one another, the tags can have part of their sequence in common so as to identify the molecules to which they are attached as being of a particular partitioned set. For example, if the molecules of the sample are partitioned into two partitioned sets—P1 and P2, then the molecules in P1 can be tagged with A1, A2, A3, and so forth, and the molecules in P2 can be tagged with B1, B2, B3, and so forth. Such a tagging system allows distinguishing the partitioned sets and between the molecules within a partitioned set. In some embodiments, the tag comprises partition tag (i.e., partition identifier). In such embodiments, the nucleic acid molecules within a partitioned set receive the same partition tag and is different from the partition tag attached to the nucleic acid molecules of the other partitioned set(s). In some embodiments, the tag sequences used do not comprise a nucleotide sequence recognized by the methylation sensitive restriction enzyme(s) used in the method.

In 308, the nucleic acid molecules in at least one partitioned set is digested with at least one methylation sensitive restriction enzyme (MSRE). In some embodiments, the nucleic acids in at least one partitioned set is digested with at least two MSREs. In some embodiments, two MSREs are used for digesting the nucleic acid molecules in at least one partitioned set. In some embodiments, the two MSREs are BstUI and HpaII. In some embodiments, the two MSREs are HhaI and AccII. In some embodiments, three MSREs are used for digesting the nucleic acid molecules in at least one partitioned set. In some embodiments, the three MSREs are BstUI, HpaII and Hin6I. In some embodiments, the MSRE is selected from the group consisting of AatII, AccII, AciI, Aor13HI, Aor15HI, BspT104I, BssHII, BstUI, Cfr10I, ClaI, CpoI, Eco52I, HaeII, HapII, HhaI, Hin6I, HpaII, HpyCH4IV, MluI, MspI, NaeI, NotI, NruI, NsbI, PmaCI, Psp1406I, PvuI, SacII, SalI, SmaI, and SnaBI. In some embodiments, any commercially available MSRE can be used (MSREs provided by Takara Bio USA Inc., New England Biolabs® Inc. and/or Thermo Fisher Scientific Inc. can be used).

In 310, after MSRE digestion, the nucleic acid molecules in the one or more partitioned sets can be enriched for genomic regions of interest. In some embodiments, the genomic regions of interest can comprise differentially methylated regions for cancer detection. In 312, at least a subset of the enriched molecules is sequenced by a next generation sequencer. In 314, the sequencing reads generated by the sequencer are then analyzed using bioinformatic tools/algorithms to determine the number of molecules in the one or more partitioned sets, which in turn is used to determine the methylation status at one or more genetic loci of the nucleic acid molecules in at least one partitioned sets. In some embodiments, the one or more genetic loci can comprise multiple genetic loci. In some embodiments, the one or more genetic loci can comprise one or more genomic regions. In some embodiments, the genomic regions can be promoter region of genes. In some embodiments, prior to sequencing, the nucleic acid molecules can be amplified via PCR amplification. In some embodiments, the primers used in the amplification can comprise at least one sample index. In some embodiments, nucleic acid molecules digested by a MSRE are not amplified. In some such embodiments, essentially all nucleic acid molecules in a sample are amplified except the nucleic acid molecules digested by a MSRE.

In some embodiments, the method can further comprise, detecting the presence or absence of cancer in the subject based on the methylation status at one or more genetic loci of the nucleic acid molecules in at least one partitioned set. In some embodiments, the method further comprises, determining a level of cancer in the polynucleotide sample, for example, by determining a level of DNA from cancer cells in the polynucleotide sample.

Figure 4:
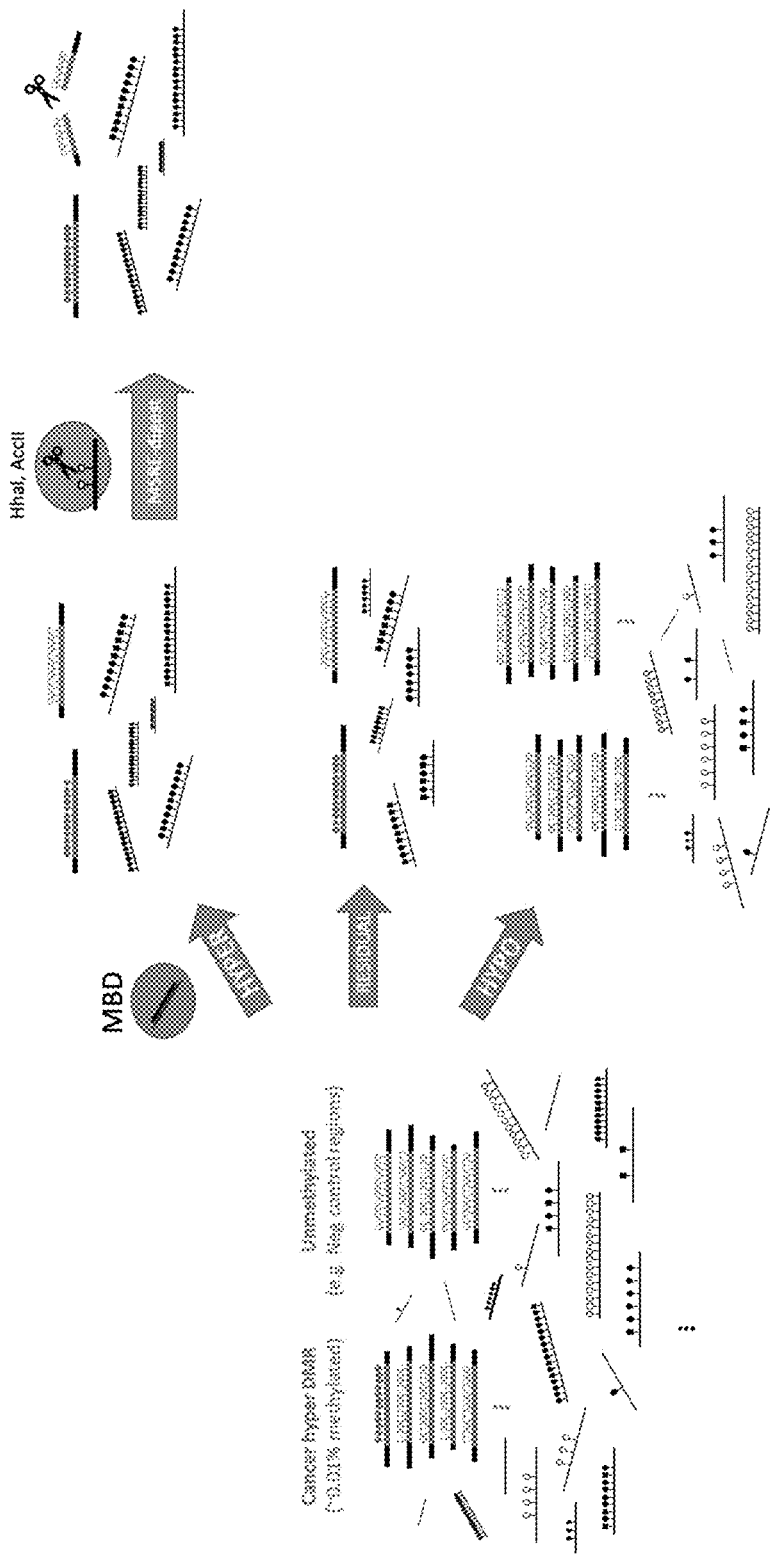
FIG. 4 is a schematic diagram of a method for detecting the presence or absence of cancer in a subject according to certain embodiments of the disclosure.

FIG. 4 illustrates an exemplary workflow to detect the presence or absence of cancer according to certain embodiments of the disclosure beginning with a cfDNA sample, in which cfDNA is isolated from the blood sample and the cfDNA sample comprises cfDNA molecules belonging to cancer hypermethylated DMR regions and unmethylated control regions; the cfDNA is partitioned using a methyl-binding domain protein (MBD) into hypo methylated, residual (i.e., intermediately methylated), and hyper methylated partitioned sets; each partitioned set is subjected to molecular barcoding to distinguishably tag DNA from the hypo, residual, and hyper partitioned sets; the hyper partitioned set is digested with two MSREs—HhaI and AccI, cleaving the unmethylated cfDNA molecules at the RE recognition site; and then partitioned sets (including the MSRE digested hyper partitioned set) are pooled, captured, amplified, and sequenced. In some embodiments, nucleic acid molecules digested by a MSRE are not amplified. In some such embodiments, essentially all nucleic acid molecules in a sample are amplified except the nucleic acid molecules digested by a MSRE.

In some embodiments, MSREs are chosen to maximize the number of methylation biomarker sequences (i.e., DMRs) targeted. In some embodiments, if two or more MSREs are used in a single digestion, the enzyme buffers should be compatible (verified by the vendor and/or tested empirically). Additionally, MSREs should have a mechanism to inactivate their activity that is compatible with downstream assay processing. For example, if MSRE digestion is performed prior to ligation, heat inactivation (>65°

C.) of MSRE would not be appropriate as it would denature dsDNA, rendering it incompatible with adapter ligation reaction.

In some embodiments, the methylation sensitive restriction enzymes that do not cleave the DNA if a particular nucleotide base is methylated at the recognition sequence can be used. Such MSREs can be used in hyper partition only in order to remove unmethylated molecules that partitioned incorrectly in the hyper partition; thereby improving methylated nucleic acid molecule detection specificity. In some embodiments, the methylation sensitive restriction enzymes that cleave the DNA if a particular nucleotide base is methylated at the recognition sequence can be used. Such MSREs can be used in hypo partition in order to remove methylated molecules that partitioned incorrectly in the hypo partition; thereby improving unmethylated nucleic acid molecules detection specificity. In some embodiments, both hyper (and residual) and hypo partitions are digested with MSREs such that (i) MSRE(s) that cleave DNA if there are unmethylated nucleotide(s) at the recognition site are used in hyper (and residual) partition and (ii) MSRE(s) that cleave DNA if there are methylated nucleotide(s) at the recognition site are used in the hypo partition.

In some embodiments, after adapter ligation, if more than one partition (e.g. hyper and residual) is to be digested with same MSREs, the digestions can be performed on each partition separately or the partitions can be combined and digested in one reaction. In some embodiments, performing the digestion separately on each partition can be advantageous if necessary enzyme performance (efficiency, specificity) can only be achieved using with separate reactions. In some embodiments, combining the partitions and then performed MSRE digestion can be beneficial in reducing assay's cost of goods sold—COGS (SPRI beads, enzymes, PCR plates, pipetting tips, etc.) and for streamlining the scaled, automated assay (i.e. single digestion reaction per sample).

In some embodiments, if MSRE digestion (where MSRE cleaves unmethylated DNA at the recognition site) is performed prior to the ligation of adapters, the cleaved fragments of the molecules can be retained and the ends of molecules matching RE recognition sites are used to identify a unmethylated molecule in the hyper partition. In such embodiments, when analyzing cfDNA sample, if there is genomic DNA contamination, then genomic DNA can be cleaved by MSRE (prior to adapter ligation) and can lead to genomic DNA contamination. This can be avoided by performing adapter ligation prior to MSRE digestion.

In some embodiments, all the partitioned sets or a subset of all the partitioned sets can be sequenced. In some embodiments, only the one or more partitioned sets for which MSRE digestion was performed can be sequenced to analyze nucleic acid molecules in the cancer DMRs.

In some embodiments, the polynucleotide sample is partitioned into two partitioned sets. In some embodiments, the polynucleotide sample is partitioned into three partitioned sets. In some embodiments, MSRE digestion is performed to nucleic acid molecules in hyper partition and hypo partition, wherein the MSRE used in hyper partition cleaves DNA if the recognition site has unmethylated nucleotides and the MSRE used in hypo partition cleaves DNA if the recognition site has methylated nucleotides. This enables simultaneous sensitive detection of hyper and hypo DMRs.

In some embodiments, the polynucleotide sample is between 1 ng and 500 ng. In some embodiments, the polynucleotide sample is less than 500 ng. In some embodiments, the polynucleotide sample is selected from the group consisting of a DNA sample, an RNA sample, a cell-free DNA sample, and a cell-free RNA sample. In some embodiments, the polynucleotide sample is a cfDNA sample obtained from the blood of the subject. In some embodiments, the polynucleotide sample is a DNA sample obtained from the tumor tissue biopsy.

II. General Features of the Methods

A. Samples

A sample can be any biological sample isolated from a subject. Samples can include body tissues, whole blood, platelets, serum, plasma, stool, red blood cells, white blood cells or leucocytes, endothelial cells, tissue biopsies (e.g., biopsies from known or suspected solid tumors), cerebrospinal fluid, synovial fluid, lymphatic fluid, ascites fluid, interstitial or extracellular fluid (e.g., fluid from intercellular spaces), gingival fluid, crevicular fluid, bone marrow, pleural effusions, cerebrospinal fluid, saliva, mucous, sputum, semen, sweat, and urine. Samples may thus be bodily fluids, such as blood and fractions thereof, and urine. Such samples can include nucleic acids shed from tumors. The nucleic acids can include DNA and RNA, and can be in double- and single-stranded forms. In some embodiments, a sample comprises cell-free DNA. A sample can be in the form originally isolated from a subject or can have been subjected to further processing to remove or add components, such as cells, enrich for one component relative to another, or convert one form of nucleic acid to another, such as RNA to DNA or single-stranded nucleic acids to double-stranded. Thus, for example, a bodily fluid for analysis can be plasma or serum containing cell-free nucleic acids, e.g., cell-free DNA (cfDNA).

A sample can be isolated or obtained from a subject and transported to a site of sample analysis. The sample may be preserved and shipped at a desirable temperature, e.g., room temperature, 4° C., −20° C., and/or −80° C. A sample can be isolated or obtained from a subject at the site of the sample analysis. The subject can be a human, a mammal, an animal, a companion animal, a service animal, or a pet. The subject may have a cancer. The subject may not have cancer or a detectable cancer symptom. The subject may have been treated with one or more cancer therapy, e.g., any one or more of chemotherapies. The subject may be in remission. The subject may or may not be diagnosed of being susceptible to cancer or any cancer-associated genetic mutations/disorders.

In some embodiments, the sample volume of bodily fluid taken from a subject depends on the desired read depth for sequenced regions. Examples of volumes are about 0.4-40 milliliters (mL), about 5-20 mL, about 10-20 mL. For example, the volume can be about 0.5 mL, about 1 mL, about 5 mL, about 10 mL, about 20 mL, about 30 mL, about 40 mL, or more milliliters. A volume of sampled plasma is typically between about 5 mL to about 20 mL.

The sample can comprise various amounts of nucleic acid. Typically, the amount of nucleic acid in a given sample is equates with multiple genome equivalents. For example, a sample of about 30 nanograms (ng) DNA can contain about 10,000 ($10^4$) haploid human genome equivalents and, in the case of cfDNA, about 200 billion ($2 \times 10^{11}$) individual polynucleotide molecules. Similarly, a sample of about 100 ng of DNA can contain about 30,000 haploid human genome equivalents and, in the case of cfDNA, about 600 billion individual molecules.

In some embodiments, a sample comprises nucleic acids from different sources, e.g., from cells and from cell-free sources (e.g., blood samples, etc.). Typically, a sample includes nucleic acids carrying mutations. For example, a sample optionally comprises DNA carrying germline mutations and/or somatic mutations. Typically, a sample comprises DNA carrying cancer-associated mutations (e.g., cancer-associated somatic mutations).

Example amounts of cell-free nucleic acids in a sample before amplification typically range from about 1 femtogram (fg) to about 1 microgram (μg), e.g., about 1 picogram (pg) to about 200 nanograms (ng), about 1 ng to about 100 ng, about 10 ng to about 1000 ng. In some embodiments, a sample includes up to about 600 ng, up to about 500 ng, up to about 400 ng, up to about 300 ng, up to about 200 ng, up to about 100 ng, up to about 50 ng, or up to about 20 ng of cell-free nucleic acid molecules. Optionally, the amount is at least about 1 fg, at least about 10 fg, at least about 100 fg, at least about 1 pg, at least about 10 pg, at least about 100 pg, at least about 1 ng, at least about 10 ng, at least about 100 ng, at least about 150 ng, or at least about 200 ng of cell-free nucleic acid molecules. In some embodiments, the amount is up to about 1 fg, about 10 fg, about 100 fg, about 1 pg, about 10 pg, about 100 pg, about 1 ng, about 10 ng, about 100 ng, about 150 ng, or about 200 ng of cell-free nucleic acid molecules. In some embodiments, methods include obtaining between about 1 fg to about 200 ng cell-free nucleic acid molecules from samples.

Cell-free nucleic acids typically have a size distribution of between about 100 nucleotides in length and about 500 nucleotides in length, with molecules of about 110 nucleotides in length to about 230 nucleotides in length representing about 90% of molecules in the sample, with a mode of about 168 nucleotides length (in samples from human subjects) and a second minor peak in a range between about 240 nucleotides to about 440 nucleotides in length. In some embodiments, cell-free nucleic acids are from about 160 nucleotides to about 180 nucleotides in length, or from about 320 nucleotides to about 360 nucleotides in length, or from about 440 nucleotides to about 480 nucleotides in length.

In some embodiments, cell-free nucleic acids are isolated from bodily fluids through a partitioning step in which cell-free nucleic acids, as found in solution, are separated from intact cells and other non-soluble components of the bodily fluid. In some embodiments, partitioning includes techniques such as centrifugation or filtration. Alternatively, cells in bodily fluids may be lysed, and cell-free and cellular nucleic acids may be processed together. Generally, after addition of buffers and wash steps, cell-free nucleic acids may be precipitated with, for example, an alcohol. In some embodiments, additional clean-up steps are used, such as silica-based columns to remove contaminants or salts. Non-specific bulk carrier nucleic acids, for example, are optionally added throughout the reaction to optimize aspects of the example procedure, such as yield. After such processing, samples typically include various forms of nucleic acids including double-stranded DNA, single-stranded DNA and/or single-stranded RNA. Optionally, single-stranded DNA and/or single-stranded RNA are converted to double-stranded forms so that they are included in subsequent processing and analysis steps.

Double-stranded DNA molecules in a sample and single stranded nucleic acid molecules that have been converted to double stranded DNA molecules can be linked to adapters at either one end or both ends. Typically, double stranded molecules are blunt ended by treatment with a polymerase with a 5'-3' polymerase and a 3'-5' exonuclease (or proof reading function), in the presence of all four standard nucleotides. Klenow large fragment and T4 polymerase are examples of suitable polymerase. The blunt ended DNA molecules can be ligated with at least partially double stranded adapter (e.g., a Y shaped or bell-shaped adapter). Alternatively, complementary nucleotides can be added to blunt ends of sample nucleic acids and adapters to facilitate ligation. Contemplated herein are both blunt end ligation and sticky end ligation. In blunt end ligation, both the nucleic acid molecules and the adapter tags have blunt ends. In sticky-end ligation, typically, the nucleic acid molecules bear an "A" overhang and the adapters bear a "T" overhang.

B. Partitioning, Adding Adapters, Tagging

In another embodiment, a partitioning scheme can be performed using the following exemplary procedure. Nucleic acids are linked at both ends to Y-shaped adapters including primer binding sites and tags. The molecules are amplified. The amplified molecules are then fractionated by contact with an antibody preferentially binding to 5-methylcytosine to produce two partitions. One partition includes original molecules lacking methylation and amplification copies having lost methylation. The other partition includes original DNA molecules with methylation. The partition including original DNA molecules with methylation is subjected to a procedure that affects a first nucleobase in the DNA differently from a second nucleobase in the DNA of the first partition, wherein the first nucleobase is a modified or unmodified nucleobase, the second nucleobase is a modified or unmodified nucleobase different from the first nucleobase, and the first nucleobase and the second nucleobase have the same base pairing specificity. The two partitions are then processed and sequenced separately with further amplification of the methylated partition. The sequence data of the two partitions can then be compared. In this example, tags are not used to distinguish between methylated and unmethylated DNA but rather to distinguish between different molecules within these partitions so that one can determine whether reads with the same start and stop points are based on the same or different molecules.

Tags may be incorporated into or otherwise joined to adapters by chemical synthesis, ligation (e.g., blunt-end ligation or sticky-end ligation), or overlap extension polymerase chain reaction (PCR), among other methods. Such adapters may be ultimately joined to the target nucleic acid molecule. In other embodiments, one or more rounds of amplification cycles (e.g., PCR amplification) are generally applied to introduce sample indexes to a nucleic acid molecule using conventional nucleic acid amplification methods. The amplifications may be conducted in one or more reaction mixtures (e.g., a plurality of microwells in an array). Molecular barcodes and/or sample indexes may be introduced simultaneously, or in any sequential order. In some embodiments, molecular barcodes and/or sample indexes are introduced prior to and/or after sequence capturing steps are performed. In some embodiments, only the molecular barcodes are introduced prior to probe capturing and the sample indexes are introduced after sequence capturing steps are performed. In some embodiments, both the molecular barcodes and the sample indexes are introduced prior to performing probe-based capturing steps. In some embodiments, the sample indexes are introduced after sequence capturing steps are performed. In some embodiments, molecular barcodes are incorporated to the nucleic acid molecules (e.g. cfDNA molecules) in a sample through adapters via ligation (e.g., blunt-end ligation or sticky-end ligation). In some embodiments, sample indexes are incorporated to the nucleic acid molecules (e.g. cfDNA molecules) in a sample through overlap extension polymerase chain reaction (PCR). Typically, sequence capturing protocols involve introducing a single-stranded nucleic acid molecule complementary to a targeted nucleic acid sequence, e.g., a coding sequence of a genomic region and mutation of such region is associated with a cancer type.

In some embodiments, the tags may be located at one end or at both ends of the sample nucleic acid molecule. In some embodiments, tags are predetermined or random or semi-random sequence oligonucleotides. In some embodiments, the tags may be less than or equal to about 500, 200, 100, 50, 20, 10, 9, 8, 7, 6, 5, 4, 3, 2, or 1 nucleotides in length. The tags may be linked to sample nucleic acids randomly or non-randomly.

In some embodiments, each sample is uniquely tagged with a sample index or a combination of sample indexes. In some embodiments, each nucleic acid molecule of a sample or sub-sample is uniquely tagged with a molecular barcode or a combination of molecular barcodes. In other embodiments, a plurality of molecular barcodes may be used such that molecular barcodes are not necessarily unique to one another in the plurality (e.g., non-unique molecular barcodes). In these embodiments, molecular barcodes are generally attached (e.g., by ligation) to individual molecules such that the combination of the molecular barcode and the sequence it may be attached to creates a unique sequence that may be individually tracked. Detection of non-unique molecular barcodes in combination with endogenous sequence information (e.g., the beginning (start) and/or end (stop) genomic location/position corresponding to the sequence of the original nucleic acid molecule in the sample, start and stop genomic positions corresponding to the sequence of the original nucleic acid molecule in the sample, the beginning (start) and/or end (stop) genomic location/position of the sequence read that is mapped to the reference sequence, start and stop genomic positions of the sequence read that is mapped to the reference sequence, sub-sequences of sequence reads at one or both ends, length of sequence reads, and/or length of the original nucleic acid molecule in the sample) typically allows for the assignment of a unique identity to a particular molecule. In some embodiments, beginning region comprises the first 1, first 2, the first 5, the first 10, the first 15, the first 20, the first 25, the first 30 or at least the first 30 base positions at the 5' end of the sequencing read that align to the reference sequence. In some embodiments, the end region comprises the last 1, last 2, the last 5, the last 10, the last 15, the last 20, the last 25, the last 30 or at least the last 30 base positions at the 3' end of the sequencing read that align to the reference sequence. The length, or number of base pairs, of an individual sequence read are also optionally used to assign a unique identity to a given molecule. As described herein, fragments from a single strand of nucleic acid having been assigned a unique identity, may thereby permit subsequent identification of fragments from the parent strand, and/or a complementary strand.

In some embodiments, molecular barcodes are introduced at an expected ratio of a set of identifiers (e.g., a combination of unique or non-unique molecular barcodes) to molecules in a sample. One example format uses from about 2 to about 1,000,000 different molecular barcode sequences, or from about 5 to about 150 different molecular barcode sequences, or from about 20 to about 50 different molecular barcode sequences, ligated to both ends of a target molecule. Alternatively, from about 25 to about 1,000,000 different molecular barcode sequences may be used. For example, 20-50× 20-50 molecular barcode sequences (i.e., one of the 20-50 different molecular barcode sequences can be attached to each end of the target molecule) can be used. Such numbers of identifiers are typically sufficient for different molecules having the same start and stop points to have a high probability (e.g., at least 94%, 99.5%, 99.99%, or 99.999%) of receiving different combinations of identifiers. In some embodiments, about 80%, about 90%, about 95%, or about 99% of molecules have the same combinations of molecular barcodes.

In some embodiments, the assignment of unique or non-unique molecular barcodes in reactions is performed using methods and systems described in, for example, U.S. Patent Application Nos. 20010053519, 20030152490, and 20110160078, and U.S. Pat. Nos. 6,582,908, 7,537,898, 9,598,731, and 9,902,992, each of which is hereby incorporated by reference in its entirety. Alternatively, in some embodiments, different nucleic acid molecules of a sample may be identified using only endogenous sequence information (e.g., start and/or stop positions, sub-sequences of one or both ends of a sequence, and/or lengths).

In certain embodiments described herein, a population of different forms of nucleic acids (e.g., hypermethylated and hypomethylated DNA in a sample) can be physically partitioned prior to analysis, e.g., sequencing, or tagging and sequencing. For example, in some embodiments, the partitioning comprises separating nucleic acid molecules into partition sets based on a differential binding affinity of the nucleic acid molecules to a binding agent that preferentially binds to nucleic acid molecules comprising methylated nucleotides. In some embodiments, partitioned sets are modified by, for example, digesting at least a subset of at least one partitioned set with a MSRE. This approach can be used to determine, for example, whether hypermethylation variable epigenetic target regions show hypermethylation characteristic of tumor cells or hypomethylation variable epigenetic target regions show hypomethylation characteristic of tumor cells. Additionally, by partitioning a heterogeneous nucleic acid population, one may increase rare signals, e.g., by enriching rare nucleic acid molecules that are more prevalent in one fraction (or partition) of the population. For example, a genetic variation present in hyper-methylated DNA but less (or not) in hypomethylated DNA can be more easily detected by partitioning a sample into hyper-methylated and hypo-methylated nucleic acid molecules. By analyzing multiple fractions of a sample, a multi-dimensional analysis of a single locus of a genome or species of nucleic acid can be performed and hence, greater sensitivity can be achieved.

In some instances, a heterogeneous nucleic acid sample is partitioned into two or more partitions (e.g., at least 3, 4, 5, 6 or 7 partitions). In some embodiments, each partition is differentially tagged—i.e., each partition can have a different set of molecular barcodes. Tagged partitions can then be pooled together for collective sample prep and/or sequencing. The partitioning-tagging-pooling steps can occur more than once, with each round of partitioning occurring based on a different characteristics (examples provided herein) and tagged using differential tags that are distinguished from other partitions and partitioning means.

Examples of characteristics that can be used for partitioning include sequence length, methylation level, nucleosome binding, sequence mismatch, immunoprecipitation, and/or proteins that bind to DNA. Resulting partitions can include one or more of the following nucleic acid forms: single-stranded DNA (ssDNA), double-stranded DNA (dsDNA), shorter DNA fragments and longer DNA fragments. In some embodiments, partitioning based on a cytosine modification (e.g., cytosine methylation) or methylation generally is performed and is optionally combined with at least one additional partitioning step, which may be based on any of the foregoing characteristics or forms of DNA. In some embodiments, a heterogeneous population of nucleic acids is partitioned into nucleic acids with one or more epigenetic modifications and without the one or more epigenetic modifications. Examples of epigenetic modifications include presence or absence of methylation; level of methylation; type of methylation (e.g., 5-methylcytosine versus other types of methylation, such as adenine methylation and/or cytosine hydroxymethylation); and association and level of association with one or more proteins, such as histones. Alternatively, or additionally, a heterogeneous population of nucleic acids can be partitioned into nucleic acid molecules associated with nucleosomes and nucleic acid molecules devoid of nucleosomes. Alternatively, or additionally, a heterogeneous population of nucleic acids may be partitioned into single-stranded DNA (ssDNA) and double-stranded DNA (dsDNA). Alternatively, or additionally, a heterogeneous population of nucleic acids may be partitioned based on nucleic acid length (e.g., molecules of up to 160 bp and molecules having a length of greater than 160 bp).

In some embodiments, a population of nucleic acids is partitioned into two or more different partitions. Each partition is representative of a different nucleic acid form, and a first partition comprises DNA with a cytosine modification in a greater proportion than a second partition. Each partition is distinctly tagged. The first partition is subjected to a procedure that affects a first nucleobase in the DNA differently from a second nucleobase in the DNA of the first partition, wherein the first nucleobase is a modified or unmodified nucleobase, the second nucleobase is a modified or unmodified nucleobase different from the first nucleobase, and the first nucleobase and the second nucleobase have the same base pairing specificity. The tagged nucleic acids are pooled together prior to sequencing. Sequence reads are obtained and analyzed, including to distinguish the first nucleobase from the second nucleobase in the DNA of the first partition, in silico. Tags are used to sort reads from different partitions. Analysis to detect genetic variants can be performed on a partition-by-partition level, as well as whole nucleic acid population level. For example, analysis can include in silico analysis to determine genetic variants, such as CNV, SNV, indel, fusion in nucleic acids in each partition. In some instances, in silico analysis can include determining chromatin structure. For example, coverage of sequence reads can be used to determine nucleosome positioning in chromatin. Higher coverage can correlate with higher nucleosome occupancy in genomic region while lower coverage can correlate with lower nucleosome occupancy or nucleosome depleted region (NDR).

Samples can include nucleic acids varying in modifications including post-replication modifications to nucleotides and binding, usually noncovalently, to one or more proteins.

In an embodiment, the population of nucleic acids is one obtained from a serum, plasma or blood sample from a subject suspected of having neoplasia, a tumor, or cancer or previously diagnosed with neoplasia, a tumor, or cancer. The population of nucleic acids includes nucleic acids having varying levels of methylation. Methylation can occur from any one or more post-replication or transcriptional modifications. Post-replication modifications include modifications of the nucleotide cytosine, particularly at the 5-position of the nucleobase, e.g., 5-methylcytosine, 5-hydroxymethylcytosine, 5-formylcytosine and 5-carboxylcytosine.

Agents used in the partitioning, such as binding agents, can be antibodies with the desired specificity, natural binding partners or variants thereof (Bock et al., Nat Biotech 28: 1106-1114 (2010); Song et al., Nat Biotech 29: 68-72 (2011)), or artificial peptides selected e.g., by phage display to have specificity to a given target.

Examples of binding agents contemplated herein include methyl binding domain (MBDs) and methyl binding proteins (MBPs) as described herein, including proteins such as MeCP2 and antibodies preferentially binding to 5-methylcytosine. Where an antibody is used to immunoprecipitate methylated DNA, the methylated DNA may be recovered in single-stranded form. In such embodiments, a second strand can be synthesized. Hypermethylated (and optionally intermediately methylated) partitions may then be contacted with an MSRE that does not cleave hemi-methylated DNA but cleaves unmethylated DNA, such as HpaII, BstUI, or Hin6i. Alternatively or in addition, hypomethylated (and optionally intermediately methylated) partitions may then be contacted with an MSRE that cleaves hemi-methylated DNA but does not cleave unmethylated DNA.

Likewise, partitioning of different forms of nucleic acids can be performed using histone binding proteins which can separate nucleic acids bound to histones from free or unbound nucleic acids. Examples of histone binding proteins that can be used in the methods disclosed herein include RBBP4, RbAp48 and SANT domain peptides.

Although for some binding agents and some nucleic acid modifications, binding to the agent may occur in an essentially all or none manner depending on whether a nucleic acid bears a modification, the separation may be one of degree. In such instances, nucleic acids overrepresented in a modification bind to the agent at a greater extent that nucleic acids underrepresented in the modification. Alternatively, nucleic acids having modifications may bind in an all or nothing manner. But then, various levels of modifications may be sequentially eluted from the binding agent.

For example, in some embodiments, partitioning can be binary or based on degree/level of modifications. For example, all methylated fragments can be partitioned from unmethylated fragments using methyl-binding domain proteins (e.g., MethylMinder Methylated DNA Enrichment Kit (ThermoFisher Scientific). Subsequently, additional partitioning may involve eluting fragments having different levels of methylation by adjusting the salt concentration in a solution with the methyl-binding domain and bound fragments. As salt concentration increases, fragments having greater methylation levels are eluted.

In some instances, the final partitions are representative of nucleic acids having different extents of modifications (overrepresentative or underrepresentative of modifications). Overrepresentation and underrepresentation can be defined by the number of modifications born by a nucleic acid relative to the median number of modifications per strand in a population. For example, if the median number of 5-methylcytosine residues in nucleic acid in a sample is 2, a nucleic acid including more than two 5-methylcytosine residues is overrepresented in this modification and a nucleic acid with 1 or zero 5-methylcytosine residues is underrepresented. The effect of the affinity separation is to enrich for nucleic acid molecules overrepresented in a modification in a bound phase and for nucleic acid molecules underrepresented in a modification in an unbound phase (i.e. in solution). The nucleic acid molecules in the bound phase can be eluted before subsequent processing.

When using MethylMiner Methylated DNA Enrichment Kit (ThermoFisher Scientific) DNA comprising various levels of methylation can be partitioned using sequential elutions. For example, a hypomethylated partition (no methylation) can be separated from a methylated partition by contacting the nucleic acid population with the MBD from the kit, which is attached to magnetic beads. The beads are used to separate out the methylated nucleic acids from the non-methylated nucleic acids. Subsequently, one or more elution steps are performed sequentially to elute nucleic acids having different levels of methylation. For example, a first set of methylated nucleic acids can be eluted at a salt concentration of 160 mM or higher, e.g., at least 150 mM, at least 200 mM, 300 mM, 400 mM, 500 mM, 600 mM, 700 mM, 800 mM, 900 mM, 1000 mM, or 2000 mM. After such methylated nucleic acids are eluted, magnetic separation is once again used to separate higher level of methylated nucleic acids from those with lower level of methylation. The elution and magnetic separation steps can repeat themselves to create various partitions such as a hypomethylated partition (representative of no methylation), a methylated partition (representative of low level of methylation), and a hyper methylated partition (representative of high level of methylation).

In some methods, nucleic acids bound to an agent used for partitioning are subjected to a wash step. The wash step washes off nucleic acids weakly bound to the binding agent. Such nucleic acids can be enriched in nucleic acids having the modification to an extent close to the mean or median (i.e., intermediate between nucleic acids remaining bound to the solid phase and nucleic acids not binding to the solid phase on initial contacting of the sample with the agent).

The partitioning results in at least two, and sometimes three or more partitions of nucleic acids with different extents of a modification. While the partitions are still separate, the nucleic acids of at least one partition, and usually two or three (or more) partitions are linked to nucleic acid tags, usually provided as components of adapters, with the nucleic acids in different partitions receiving different tags that distinguish members of one partition from another. The tags linked to nucleic acid molecules of the same partition can be the same or different from one another. But if different from one another, the tags may have part of their code in common so as to identify the molecules to which they are attached as being of a particular partition.

For further details regarding partitioning nucleic acid samples based on characteristics such as methylation, see WO2018/119452, which is incorporated herein by reference.

In some embodiments, the nucleic acid molecules can be partitioned into different partitions based on the nucleic acid molecules that are bound to a specific protein or a fragment thereof and those that are not bound to that specific protein or fragment thereof.

Nucleic acid molecules can be partitioned based on DNA-protein binding. Protein-DNA complexes can be partitioned based on a specific property of a protein. Examples of such properties include various epitopes, modifications (e.g., histone methylation or acetylation) or enzymatic activity. Examples of proteins which may bind to DNA and serve as a binding agent for partitioning may include, but are not limited to, protein A and protein G. Any suitable method can be used to partition the nucleic acid molecules based on protein bound regions. Examples of methods used to partition nucleic acid molecules based on protein bound regions include, but are not limited to, SDS-PAGE, chromatin-immuno-precipitation (ChIP), heparin chromatography, and asymmetrical field flow fractionation (AF4).

In general, elution is a function of the number of methylated sites per nucleic acid molecule, with molecules having more methylation eluting under increased salt concentrations. To elute the DNA into distinct populations or partitions based on the extent of methylation, one can use a series of elution buffers of increasing NaCl concentration. Salt concentration can range from about 100 nm to about 2500 mM NaCl. In one embodiment, the process results in three (3) partitions. Molecules are contacted with a solution at a first salt concentration and comprising a molecule comprising a methyl binding domain, which molecule can be attached to a capture moiety, such as streptavidin. At the first salt concentration a population of molecules will bind to the MBD and a population will remain unbound. The unbound population can be separated as a "hypomethylated" population. For example, a first partition representative of the hypomethylated form of DNA is that which remains unbound at a low salt concentration, e.g., 100 mM or 160 mM. A second partition representative of intermediate methylated DNA is eluted using an intermediate salt concentration, e.g., between 100 mM and 2000 mM concentration. This is also separated from the sample. A third partition representative of hypermethylated form of DNA is eluted using a high salt concentration, e.g., at least about 2000 mM.

Partitioning procedures may result in imperfect sorting of DNA molecules among the resulting partitions or fractions. For example, a minority of the molecules in a hypomethylated partition may be highly modified (e.g., hypermethylated), and/or a minority of the molecules in a hypermethylated partition may be unmodified or mostly unmodified (e.g., unmethylated or mostly unmethylated). Such molecules are considered nonspecifically partitioned. The methods described herein comprise steps that can reduce technical noise from nonspecifically partitioned DNA, e.g., by degrading it and/or by converting certain bases such that nonspecifically partitioned DNA can be identified following sequencing. Thus, the methods described herein can provide improved sensitivity and/or streamlined analysis.

In some instances, each partitioned set (representative of a different nucleic acid form) is differentially tagged with molecular barcodes, and the partitioned sets are pooled together prior to sequencing. In other instances, the different forms are separately sequenced.

In some embodiments, the nucleic acid molecules (from the sample of polynucleotides, e.g., after partitioning) may be tagged with sample indexes and/or molecular barcodes (referred to generally as "tags"). Tags can be used to label nucleic acids of partitions so as to correlate the tag (or tags) with a specific partition. Alternatively, tags can be used in embodiments of the invention that do not employ a partitioning step. Tags or indexes can be molecules, such as nucleic acids, containing information that indicates a feature of the molecule with which the tag is associated. For example, molecules can bear a sample tag or sample index (which distinguishes molecules in one sample from those in a different sample), a partition tag (which distinguishes molecules in one partition from those in a different partition) or a molecular tag/molecular barcode/barcode (which distinguishes different molecules from one another (in both unique and non-unique tagging scenarios). In certain embodiments, a tag can comprise one or a combination of barcodes. In some embodiments, the barcode has, for example, between 10 and 100 nucleotides. A collection of barcodes can have degenerate sequences or can have sequences having a certain hamming distance, as desired for the specific purpose. So, for example, a molecular barcode can be comprised of one barcode or a combination of two barcodes, each attached to different ends of a molecule. Additionally or alternatively, for different partitions and/or samples, different sets of molecular barcodes, molecular tags, or molecular indexes can be used such that the barcodes serve as a molecular tag through their individual sequences and also serve to identify the partition and/or sample to which they correspond based the set of which they are a member.

Tagging strategies can be divided into unique tagging and non-unique tagging strategies. In unique tagging, all or substantially all of the molecules in a sample bear a different tag, so that reads can be assigned to original molecules based on tag information alone. Tags used in such methods are sometimes referred to as "unique tags". In non-unique tagging, different molecules in the same sample can bear the same tag, so that other information in addition to tag information is used to assign a sequence read to an original molecule. Such information may include start and stop coordinate, coordinate to which the molecule maps, start or stop coordinate alone, etc. Tags used in such methods are sometimes referred to as "non-unique tags". Accordingly, it is not necessary to uniquely tag every molecule in a sample. It suffices to uniquely tag molecules falling within an identifiable class within a sample. Thus, molecules in different identifiable families can bear the same tag without loss of information about the identity of the tagged molecule.

In certain embodiments of non-unique tagging, the number of different tags used can be sufficient that there is a very high likelihood (e.g., at least 99%, at least 99.9%, at least 99.99% or at least 99.999% that all molecules of a particular group bear a different tag. It is to be noted that when barcodes are used as tags, and when barcodes are attached, e.g., randomly, to both ends of a molecule, the combination of barcodes, together, can constitute a tag. This number, in term, is a function of the number of molecules falling into the calls. For example, the class may be all molecules mapping to the same start-stop position on a reference genome. The class may be all molecules mapping across a particular genetic locus, e.g., a particular base or a particular region (e.g., up to 100 bases or a gene or an exon of a gene). In certain embodiments, the number of different tags used to uniquely identify a number of molecules, z, in a class can be between any of $2*z, 3*z, 4*z, 5*z, 6*z, 7*z, 8*z, 9*z, 10*z, 11*z, 12*z, 13*z, 14*z, 15*z, 16*z, 17*z, 18*z, 19*z, 20*z$ or $100*z$ (e.g., lower limit) and any of $100,000*z, 10,000*z, 1000*z$ or $100*z$ (e.g., upper limit).

For example, in a sample of about 5 ng to 30 ng of cell free DNA, one expects around 3000 molecules to map to a particular nucleotide coordinate, and between about 3 and 10 molecules having any start coordinate to share the same stop coordinate. Accordingly, about 50 to about 50,000 different tags (e.g., between about 6 and 220 barcode combinations) can suffice to uniquely tag all such molecules. To uniquely tag all 3000 molecules mapping across a nucleotide coordinate, about 1 million to about 20 million different tags would be required.

Generally, assignment of unique or non-unique tags barcodes in reactions follows methods and systems described by US patent applications 20010053519, 20030152490, 20110160078, and U.S. Pat. Nos. 6,582,908 and 7,537,898 and 9,598,731. Tags can be linked to sample nucleic acids randomly or non-randomly.

In some embodiments, the tagged nucleic acids are sequenced after loading into a microwell plate. The microwell plate can have 96, 384, or 1536 microwells. In some cases, they are introduced at an expected ratio of unique tags to microwells. For example, the unique tags may be loaded so that more than about 1, 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 unique tags are loaded per genome sample. In some cases, the unique tags may be loaded so that less than about 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 unique tags are loaded per genome sample. In some cases, the average number of unique tags loaded per sample genome is less than, or greater than, about 1, 2, 3, 4, 5, 6, 7, 8, 9, 10, 20, 50, 100, 500, 1000, 5000, 10000, 50,000, 100,000, 500,000, 1,000,000, 10,000,000, 50,000,000 or 1,000,000,000 unique tags per genome sample.

A preferred format uses 20-50 different tags (e.g., barcodes) ligated to both ends of target nucleic acids. For example 35 different tags (e.g., barcodes) ligated to both ends of target molecules creating 35×35 permutations, which equals 1225 for 35 tags. Such numbers of tags are sufficient so that different molecules having the same start and stop points have a high probability (e.g., at least 94%, 99.5%, 99.99%, 99.999%) of receiving different combinations of tags. Other barcode combinations include any number between 10 and 500, e.g., about 15×15, about 35×35, about 75×75, about 100×100, about 250×250, about 500×500.

In some cases, unique tags may have predetermined or random or semi-random sequences. In other cases, a plurality of barcodes may be used such that barcodes are not necessarily unique to one another in the plurality. In this example, barcodes may be ligated to individual nucleic acid molecules such that the combination of the barcode and the sequence it may be ligated to creates a unique sequence that may be individually tracked. As described herein, detection of non-unique barcodes in combination with sequence data of beginning (start) and end (stop) portions of sequence reads may allow assignment of a unique identity to a particular molecule. The length or number of base pairs, of an individual sequence read may also be used to assign a unique identity to such a molecule. As described herein, fragments from a single strand of nucleic acid having been assigned a unique identity, may thereby permit subsequent identification of fragments from the parent strand.

In some embodiments, adapters, e.g., adapters comprising tags, are added to the nucleic acids after partitioning the nucleic acids, in other embodiments adapters may be added to the nucleic acids prior to partitioning the nucleic acids. In some such methods, a population of nucleic acids bearing a modification to different extents (e.g., 0, 1, 2, 3, 4, 5 or more methyl groups per nucleic acid molecule) is contacted with adapters before partitioning of the population depending on the extent of the modification. Adapters are attached to either one end or both ends of nucleic acid molecules in the population. In some embodiments, the adapters include different tags of sufficient numbers that the number of combinations of tags results in a low probability e.g., 95, 99 or 99.9% of two nucleic acids with the same start and stop points receiving the same combination of tags. Adapters, whether bearing the same or different tags, can include the same or different primer binding sites, but preferably adapters include the same primer binding site. In some embodiments, the nucleic acids are amplified from primers binding to the primer binding sites within the adapters after partitioning. Following amplification, the different partitions can then be subject to further processing steps, which may include further (e.g., clonal) amplification, and sequence analysis, in parallel but separately. Sequence data from the different partitions can then be compared.

In some embodiments, a single tag can be used to label a specific partition. In some embodiments, multiple different tags can be used to label a specific partitioned set. In embodiments employing multiple different tags to label a specific partition, the set of tags used to label one partition can be readily differentiated from the set of tags used to label other partitions. In some embodiments, a tag can be multi-functional—i.e., it can simultaneously act as a molecular identifier (i.e., molecular barcode), partition identifier (i.e., partition tag) and sample identifier (i.e., sample index). For example, if there are four DNA samples and each DNA sample is partitioned into three partitions, then the DNA molecules in each of the twelve partitions (i.e., twelve partitions for the four DNA samples in total) can be tagged with a separate set of tags such that the tag sequence attached to the DNA molecule reveals the identity of the DNA molecule, the partition it belongs to and the sample from which it was originated. In some embodiments, a tag can be used both as a molecular barcode and as a partition tag. For example, if a DNA sample is partitioned into three partitions, then DNA molecule in each partition is tagged with a separated set of tags such that the tag sequence attached to a DNA molecule reveals the identity of the DNA molecule and the partition it belongs to. In some embodiments, a tag can be used both as a molecular barcode and as a sample index. For example, if there are four DNA samples, then DNA molecules in each sample will be tagged with a separate set of tags that can be distinguishable from each sample such that the tag sequence attached to the DNA molecule serves as a molecule identifier and as a sample identifier.

In some embodiments, the tags may have additional functions, for example the tags can be used to index sample sources or used as unique molecular identifiers (which can be used to improve the quality of sequencing data by differentiating sequencing errors from mutations, for example as in Kinde et al., Proc Nat'l Acad Sci USA 108: 9530-9535 (2011), Kou et al., *PLoS ONE*, 11: e0146638 (2016)) or used as non-unique molecule identifiers, for example as described in U.S. Pat. No. 9,598,731. Similarly, in some embodiments, the tags may have additional functions, for example the tags can be used to index sample sources or used as non-unique molecular identifiers (which can be used to improve the quality of sequencing data by differentiating sequencing errors from mutations).

In one embodiment, partition tagging comprises tagging molecules in each partition with a partition tag. After re-combining partitions (e.g., to reduce the number of sequencing runs needed and avoid unnecessary cost) and sequencing molecules, the partition tags identify the source partition. In another embodiment, different partitions are tagged with different sets of molecular tags, e.g., comprised of a pair of barcodes. In this way, each molecular barcode indicates the source partition as well as being useful to distinguish molecules within a partition. For example, a first set of 35 barcodes can be used to tag molecules in a first partition, while a second set of 35 barcodes can be used tag molecules in a second partition.

In some embodiments, after partitioning and tagging with partition tags, the molecules may be pooled for sequencing in a single run. In some embodiments, a sample tag is added to the molecules, e.g., in a step subsequent to addition of partition tags and pooling. Sample tags can facilitate pooling material generated from multiple samples for sequencing in a single sequencing run.

Alternatively, in some embodiments, partition tags may be correlated to the sample as well as the partition. As a simple example, a first tag can indicate a first partition of a first sample; a second tag can indicate a second partition of the first sample; a third tag can indicate a first partition of a second sample; and a fourth tag can indicate a second partition of the second sample.

While tags may be attached to molecules already partitioned based on one or more epigenetic characteristics, the final tagged molecules in the library may no longer possess that epigenetic characteristic. For example, while single stranded DNA molecules may be partitioned and tagged, the final tagged molecules in the library are likely to be double stranded. Similarly, while DNA may be subject to partition based on different levels of methylation, in the final library, tagged molecules derived from these molecules are likely to be unmethylated. Accordingly, the tag attached to molecule in the library typically indicates the characteristic of the "parent molecule" from which the ultimate tagged molecule is derived, not necessarily to characteristic of the tagged molecule, itself.

As an example, barcodes 1, 2, 3, 4, etc. are used to tag and label molecules in the first partition; barcodes A, B, C, D, etc. are used to tag and label molecules in the second partition; and barcodes a, b, c, d, etc. are used to tag and label molecules in the third partition. Differentially tagged partitions can be pooled prior to sequencing. Differentially tagged partitions can be separately sequenced or sequenced together concurrently, e.g., in the same flow cell of an Illumina sequencer.

After sequencing, analysis of reads to detect genetic variants can be performed on a partition-by-partition level, as well as a whole nucleic acid population level. Tags are used to sort reads from different partitions. Analysis can include in silico analysis to determine genetic and epigenetic variation (one or more of methylation, chromatin structure, etc.) using sequence information, genomic coordinates length, coverage and/or copy number. In some embodiments, higher coverage can correlate with higher nucleosome occupancy in genomic region while lower coverage can correlate with lower nucleosome occupancy or a nucleosome depleted region (NDR).

C. Digesting Nucleic Acid Molecules with Restriction Enzymes

In some embodiments, a partition or partitioned set (e.g., a first, second, or third partitioned set prepared by partitioning a sample as described herein, such as on the basis of a level of a cytosine modification, such as methylation, e.g., 5-methylation) is digested by contacting the partition or partitioned set with a methylation sensitive restriction enzyme (MSRE). In some embodiments where partitioning is performed on the basis of a cytosine modification, the first partition is the partition with a higher level of the modification; the second partition is the partition with a lower level of the modification; and, when present, the third partition has a level of the modification intermediate between the first and second partitions.

As discussed above, partitioning procedures may result in imperfect sorting of DNA molecules among the partitions. The choice of MSRE can be made so as to degrade non-specifically partitioned DNA. For example, the second partition can be contacted with a MSRE that selectively digests methylated nucleic acid molecules. This can degrade non-specifically partitioned DNA in the second partition (e.g., methylated DNA) to produce a treated second partition. Alternatively or in addition, the first partition can be contacted with a MSRE that selectively digests unmethylated nucleic acid molecules, thereby degrading nonspecifically partitioned DNA in the first partition to produce a treated first partition. Degradation of nonspecifically partitioned DNA in either or both of the first or second partitions is proposed as an improvement to the performance of methods that rely on accurate partitioning of DNA on the basis of a cytosine modification, e.g., to detect the presence of aberrantly modified DNA in a sample, to determine the tissue of origin of DNA, and/or to determine whether a subject has cancer. For example, such degradation may provide improved sensitivity and/or simplify downstream analyses.

In a contacting a partition with a nuclease, such as a MSRE, one or more nucleases can be used. In some embodiments, a partition is contacted with a plurality of nucleases. The partition may be contacted with the nucleases sequentially or simultaneously. Simultaneous use of nucleases may be advantageous when the nucleases are active under similar conditions (e.g., buffer composition) to avoid unnecessary sample manipulation. Contacting the second partition with more than one MSRE can more completely degrade nonspecifically partitioned hypermethylated DNA. Similarly, contacting the first partition with more than one MSRE can more completely degrade nonspecifically partitioned hypomethylated and/or unmethylated DNA.

In some embodiments, a MSRE that selectively digests methylated nucleic acid molecules comprises one or more of MspJI, LpnPI, FspEI, or McrBC. In some embodiments, at least two MSREs that selectively digest methylated nucleic acid molecules are used. In some embodiments, at least three MSREs that selectively digest methylated nucleic acid molecules are used.

In some embodiments, a MSRE that selectively digests unmethylated nucleic acid molecules comprises one or more of AatII, AccII, AciI, Aor13HI, Aor15HI, BspT104I, BssHII, BstUI, Cfr10I, ClaI, CpoI, Eco52I, HaeII, HapII, HhaI, Hin6I, HpaII, HpyCH4IV, MluI, MspI, NaeI, NotI, NruI, NsbI, PmaCI, Psp1406I, PvuI, SacII, SalI, SmaI, and SnaBI. In some embodiments, at least two MSREs are used that selectively digest unmethylated nucleic acid molecules. In some embodiments, at least three MSREs are used that selectively digest unmethylated nucleic acid molecules. In some embodiments, the MSREs comprise BstUI and HpaII. In some embodiments, the two MSREs comprise HhaI and AccII. In some embodiments, the MSREs comprise BstUI, HpaII and Hin6I.

In some embodiments, a partition is contacted with a nuclease as described above after a step of tagging or attaching adapters to both ends of the DNA. The tags or adapters can be resistant to cleavage by the nuclease using any of the approaches described above. In this approach, cleavage can prevent the nonspecifically partitioned molecule from being carried through the analysis because the cleavage products lack tags or adapters at both ends.

Alternatively, a step of tagging or attaching adapters can be performed after digestion with a nuclease as described above. Cleaved molecules can be then identified in sequence reads based on having an end (point of attachment to tag or adapter) corresponding to a nuclease recognition site. Processing the molecules in this way can also allow the acquisition of information from the cleaved molecule, e.g., observation of somatic mutations. When tagging or attaching adapters after contacting the partition with a nuclease, and low molecular weight DNA such as cfDNA is being analyzed, it may be desirable to remove high molecular weight DNA (such as contaminating genomic DNA) from the sample before the contacting step. It may also be desirable to use nucleases that can be heat-inactivated at a relatively low temperature (e.g., 65° C. or less, or 60° C. or less) to avoid denaturing DNA, in that denaturation may interfere with subsequent ligation steps.

Where a sample is partitioned into three partitions, including a third partition containing intermediately methylated molecules, the third partition is in some embodiments contacted with a MSRE, e.g., an MSRE that selectively digests selectively digests unmethylated nucleic acid molecules. Such a step may have any of the features described elsewhere herein with respect to contacting steps, and may be performed before or after a step of tagging or attaching adapters as discussed above. In some embodiments, the first and third partitions are combined before being contacted with a MSRE. Such a step may have any of the features described elsewhere herein with respect to contacting steps, and may be performed before or after a step of tagging or attaching adapters as discussed above. In some embodiments, the first and third partitions are differentially tagged before being combined.

In some embodiments, where a sample is partitioned into three partitions, including a third partition containing intermediately methylated molecules, the third partition is in some embodiments contacted with an MSRE that selectively digests methylated nucleic acid molecules. Such a step may have any of the features described elsewhere herein with respect to contacting steps, and may be performed before or after a step of tagging or attaching adapters as discussed above. In some embodiments, the second and third partitions are combined before being contacted with the MSRE. Such a step may have any of the features described elsewhere herein with respect to contacting steps, and may be performed before or after a step of tagging or attaching adapters as discussed above. In some embodiments, the second and third partitions are differentially tagged before being combined.

In some embodiments, the DNA is purified after being contacted with the nuclease, e.g., using SPRI beads. Such purification may occur after heat inactivation of the nuclease. Alternatively, purification can be omitted; thus, for example, a subsequent step such as amplification can be performed on the partition containing heat-inactivated nuclease. In another embodiment, the contacting step can occur in the presence of a purification reagent such as SPRI beads, e.g., to minimize losses associated with tube transfers. After cleavage and heat inactivation, the SPRI beads can be re-used for cleanup by adding molecular crowding reagents (e.g., PEG) and salt.

D. Amplification

Sample nucleic acids may be flanked by adapters and amplified by PCR and other amplification methods using nucleic acid primers binding to primer binding sites in adapters flanking a DNA molecule to be amplified. In some embodiments, amplification methods involve cycles of extension, denaturation, and annealing resulting from thermocycling, or can be isothermal as, for example, in transcription mediated amplification. Other examples of amplification methods that may be optionally utilized include the ligase chain reaction, strand displacement amplification, nucleic acid sequence-based amplification, and self-sustained sequence-based replication.

Typically, the amplification reactions generate a plurality of non-uniquely or uniquely tagged nucleic acid amplicons with molecular barcodes and sample indexes at size ranging from about 150 nucleotides (nt), to about 700 nt, from 250 nt to about 350 nt, or from about 320 nt to about 550 nt. In some embodiments, the amplicons have a size of about 180 nt. In some embodiments, the amplicons have a size of about 200 nt.

In some embodiments, the present methods comprise dsDNA ligations with T-tailed and C-tailed adapters, which result in amplification of at least 50, 60, 70 or 80% of double stranded nucleic acids before linking to adapters. Preferably the present methods increase the amount or number of amplified molecules relative to control methods performed with T-tailed adapters alone by at least 10, 15 or 20%.

In some embodiments, nucleic acid molecules digested by a MSRE are not amplified. In some such embodiments, essentially all nucleic acid molecules in a sample are amplified except the nucleic acid molecules digested by a MSRE.

E. Enrichment/Capturing

In some embodiments, methods disclosed herein comprise capturing or enriching one or more target regions of nucleic acid molecules. Capture may be performed using any suitable approach known in the art. In some embodiments, capturing comprises contacting the DNA to be captured with a set of target-specific probes, for example, probes as described herein. Capturing may be performed on one or more partitions prepared during methods disclosed herein. In some embodiments, DNA is captured from at least the first partition or the second partition, e.g., at least the first partition and the second partition. Capturing may be performed on any, any two, or all subsets of a partition or partitioned set. In some embodiments, the partitions are differentially tagged (e.g., as described herein) and then pooled before undergoing capture.

The capturing step may be performed using conditions suitable for specific nucleic acid hybridization, which generally depend to some extent on features of the probes such as length, base composition, etc. Those skilled in the art will be familiar with appropriate conditions given general knowledge in the art regarding nucleic acid hybridization. In some embodiments, complexes of target-specific probes and DNA are formed.

In some embodiments, a method described herein comprises capturing cfDNA obtained from a test subject for a plurality of sets of target regions. The target regions comprise epigenetic target regions, which may show differences in methylation levels and/or fragmentation patterns depending on whether they originated from a tumor or from healthy cells. The target regions also comprise sequence-variable target regions, which may show differences in sequence depending on whether they originated from a tumor or from healthy cells. The capturing step produces a captured set of cfDNA molecules. In some embodiments, the cfDNA molecules corresponding to the sequence-variable target region set are captured at a greater capture yield in the captured set of cfDNA molecules than cfDNA molecules corresponding to the epigenetic target region set. For additional discussion of capturing steps, capture yields, and related aspects, see WO2020/160414, which is incorporated herein by reference for all purposes.

In some embodiments, a method described herein comprises contacting cfDNA obtained from a test subject with a set of target-specific probes, wherein the set of target-specific probes is configured to capture cfDNA corresponding to the sequence-variable target region set at a greater capture yield than cfDNA corresponding to the epigenetic target region set.

It can be beneficial to capture cfDNA corresponding to the sequence-variable target region set at a greater capture yield than cfDNA corresponding to the epigenetic target region set because a greater depth of sequencing may be necessary to analyze the sequence-variable target regions with sufficient confidence or accuracy than may be necessary to analyze the epigenetic target regions. The volume of data needed to determine fragmentation patterns (e.g., to test for perturbation of transcription start sites or CTCF binding sites) or fragment abundance (e.g., in hypermethylated and hypomethylated partitions) is generally less than the volume of data needed to determine the presence or absence of cancer-related sequence mutations. Capturing the target region sets at different yields can facilitate sequencing the target regions to different depths of sequencing in the same sequencing run (e.g., using a pooled mixture and/or in the same sequencing cell).

In various embodiments, the methods further comprise sequencing the captured cfDNA, e.g., to different degrees of sequencing depth for the epigenetic and sequence-variable target region sets, consistent with the discussion herein.

In some embodiments, complexes of target-specific probes and DNA are separated from DNA not bound to target-specific probes. For example, where target-specific probes are bound covalently or noncovalently to a solid support, a washing or aspiration step can be used to separate unbound material. Alternatively, where the complexes have chromatographic properties distinct from unbound material (e.g., where the probes comprise a ligand that binds a chromatographic resin), chromatography can be used.

As discussed in detail elsewhere herein, the set of target-specific probes may comprise a plurality of sets such as probes for a sequence-variable target region set and probes for an epigenetic target region set. In some such embodiments, the capturing step is performed with the probes for the sequence-variable target region set and the probes for the epigenetic target region set in the same vessel at the same time, e.g., the probes for the sequence-variable and epigenetic target region sets are in the same composition. This approach provides a relatively streamlined workflow. In some embodiments, the concentration of the probes for the sequence-variable target region set is greater that the concentration of the probes for the epigenetic target region set.

Alternatively, the capturing step is performed with the sequence-variable target region probe set in a first vessel and with the epigenetic target region probe set in a second vessel, or the contacting step is performed with the sequence-variable target region probe set at a first time and a first vessel and the epigenetic target region probe set at a second time before or after the first time. This approach allows for preparation of separate first and second compositions comprising captured DNA corresponding to the sequence-variable target region set and captured DNA corresponding to the epigenetic target region set. The compositions can be processed separately as desired (e.g., to fractionate based on methylation as described elsewhere herein) and recombined in appropriate proportions to provide material for further processing and analysis such as sequencing.

In some embodiments, the DNA is amplified. In some embodiments, amplification is performed before the capturing step. In some embodiments, amplification is performed after the capturing step.

In some embodiments, adapters are included in the DNA. This may be done concurrently with an amplification procedure, e.g., by providing the adapters in a 5' portion of a primer, e.g., as described above. Alternatively, adapters can be added by other approaches, such as ligation.

In some embodiments, tags, which may be or include barcodes, are included in the DNA, e.g., included in adapters added to the DNA. Tags can facilitate identification of the origin of a nucleic acid. For example, barcodes can be used to allow the origin (e.g., subject) whence the DNA came to be identified following pooling of a plurality of samples for parallel sequencing. This may be done concurrently with an amplification procedure, e.g., by providing the barcodes in a 5' portion of a primer, e.g., as described above. In some embodiments, adapters and tags/barcodes are provided by the same primer or primer set. For example, the barcode may be located 3' of the adapter and 5' of the target-hybridizing portion of the primer. Alternatively, barcodes can be added by other approaches, such as ligation, optionally together with adapters in the same ligation substrate.

Additional details regarding amplification, tags, and barcodes are discussed in other sections herein, which can be combined to the extent practicable with any of the embodiments set forth herein.

In some embodiments, sequences are enriched prior to sequencing the nucleic acids. Enrichment may be optionally performed for specific target regions or may be performed nonspecifically ("target sequences"). In some embodiments, targeted regions of interest may be enriched/captured with nucleic acid capture probes ("baits"), such as a target region probe set, selected for one or more bait set panels using a differential tiling and capture scheme. A differential tiling and capture scheme generally uses bait sets of different relative concentrations to differentially tile (e.g., at different "resolutions") across genomic regions associated with the baits, subject to a set of constraints (e.g., sequencer constraints such as sequencing load, utility of each bait, etc.), and capture the targeted nucleic acids at a desired level for downstream sequencing. These targeted genomic regions of interest optionally include natural or synthetic nucleotide sequences of the nucleic acid construct. In some embodiments, biotin-labeled beads with probes to one or more regions of interest can be used to capture target sequences, and optionally followed by amplification of those regions, to enrich for the regions of interest. In some embodiments, the nucleic acid capture probes can be single-stranded RNA or double-strand DNA molecules.

Sequence capture typically involves the use of oligonucleotide probes that hybridize to the target nucleic acid sequence. In some embodiments, a probe set strategy involves tiling the probes across a region of interest. Such probes can be, for example, from about 60 to about 120 nucleotides in length. The set can have a depth (e.g., depth of coverage) of about 2×, 3×, 4×, 5×, 6×, 7×, 8×, 9×, 10×, 15×, 20×, 50×, or more than 50×. The effectiveness of sequence capture generally depends, in part, on the length of the sequence in the target molecule that is complementary (or nearly complementary) to the sequence of the probe.

In some embodiments, a first target region set is captured from the first partition, comprising at least epigenetic target regions. The epigenetic target regions captured from the first partition may comprise hypermethylation variable target regions. In some embodiments, the hypermethylation variable target regions are CpG-containing regions that are unmethylated or have low methylation in cfDNA from healthy subjects (e.g., below-average methylation relative to bulk cfDNA). In some embodiments, the hypermethylation variable target regions are regions that show lower methylation in healthy cfDNA than in at least one other tissue type. Without wishing to be bound by any particular theory, cancer cells may shed more DNA into the bloodstream than healthy cells of the same tissue type. As such, the distribution of tissue of origin of cfDNA may change upon carcinogenesis. Thus, an increase in the level of hypermethylation variable target regions in the first partition can be an indicator of the presence (or recurrence, depending on the history of the subject) of cancer.

In some embodiments, a second target region set is captured from the second partition, comprising at least epigenetic target regions. The epigenetic target regions may comprise hypomethylation variable target regions. In some embodiments, the hypomethylation variable target regions are CpG-containing regions that are methylated or have high methylation in cfDNA from healthy subjects (e.g., above-average methylation relative to bulk cfDNA). In some embodiments, the hypomethylation variable target regions are regions that show higher methylation in healthy cfDNA than in at least one other tissue type. Without wishing to be bound by any particular theory, cancer cells may shed more DNA into the bloodstream than healthy cells of the same tissue type. As such, the distribution of tissue of origin of cfDNA may change upon carcinogenesis. Thus, an increase in the level of hypomethylation variable target regions in the second partition can be an indicator of the presence (or recurrence, depending on the history of the subject) of cancer.

In some embodiments, the enriched DNA molecules (or the captured set) may comprise DNA corresponding to a sequence-variable target region set and an epigenetic target region set. In some embodiments the quantity of captured sequence-variable target region DNA is greater than the quantity of the captured epigenetic target region DNA, when normalized for the difference in the size of the targeted regions (footprint size). In some embodiments, the compositions, methods and systems described in PCT Patent Application No. PCT/US2020/016120, which is hereby incorporated by reference in its entirety.

Alternatively, first and second captured sets may be provided, comprising, respectively, DNA corresponding to a sequence-variable target region set and DNA corresponding to an epigenetic target region set. The first and second captured sets may be combined to provide a combined captured set.

In a captured set comprising DNA corresponding to the sequence-variable target region set and the epigenetic target region set, including a combined captured set as discussed above, the DNA corresponding to the sequence-variable target region set may be present at a greater concentration than the DNA corresponding to the epigenetic target region set, e.g., a 1.1 to 1.2-fold greater concentration, a 1.2- to 1.4-fold greater concentration, a 1.4- to 1.6-fold greater concentration, a 1.6- to 1.8-fold greater concentration, a 1.8- to 2.0-fold greater concentration, a 2.0- to 2.2-fold greater concentration, a 2.2- to 2.4-fold greater concentration a 2.4- to 2.6-fold greater concentration, a 2.6- to 2.8-fold greater concentration, a 2.8- to 3.0-fold greater concentration, a 3.0- to 3.5-fold greater concentration, a 3.5- to 4.0, a 4.0- to 4.5-fold greater concentration, a 4.5- to 5.0-fold greater concentration, a 5.0- to 5.5-fold greater concentration, a 5.5- to 6.0-fold greater concentration, a 6.0- to 6.5-fold greater concentration, a 6.5- to 7.0-fold greater, a 7.0- to 7.5-fold greater concentration, a 7.5- to 8.0-fold greater concentration, an 8.0- to 8.5-fold greater concentration, an 8.5- to 9.0-fold greater concentration, a 9.0- to 9.5-fold greater concentration, 9.5- to 10.0-fold greater concentration, a 10- to 11-fold greater concentration, an 11- to 12-fold greater concentration a 12- to 13-fold greater concentration, a 13- to 14-fold greater concentration, a 14- to 15-fold greater concentration, a 15- to 16-fold greater concentration, a 16- to 17-fold greater concentration, a 17- to 18-fold greater concentration, an 18- to 19-fold greater concentration, a 19- to 20-fold greater concentration, a 20- to 30-fold greater concentration, a 30- to 40-fold greater concentration, a 40- to 50-fold greater concentration, a 50- to 60-fold greater concentration, a 60- to 70-fold greater concentration, a 70- to 80-fold greater concentration, a 80- to 90-fold greater concentration, or a 90- to 100-fold greater concentration. The degree of difference in concentrations accounts for normalization for the footprint sizes of the target regions, as discussed in the definition section.

a. Epigenetic Target Region Set

The epigenetic target region set may comprise one or more types of target regions likely to differentiate DNA from neoplastic (e.g., tumor or cancer) cells and from healthy cells, e.g., non-neoplastic circulating cells. Exemplary types of such regions are discussed in detail herein. In some embodiments, methods according to the disclosure comprise determining whether cfDNA molecules corresponding to the epigenetic target region set comprise or indicate cancer-associated epigenetic modifications (e.g., hypermethylation in one or more hypermethylation variable target regions; one or more perturbations of CTCF binding; and/or one or more perturbations of transcription start sites) and/or copy number variations (e.g., focal amplifications). The epigenetic target region set may also comprise one or more control regions, e.g., as described herein.

In some embodiments, the epigenetic target region set has a footprint of at least 100 kbp, e.g., at least 200 kbp, at least 300 kbp, or at least 400 kbp. In some embodiments, the epigenetic target region set has a footprint in the range of 100-20 Mbp, e.g., 100-200 kbp, 200-300 kbp, 300-400 kbp, 400-500 kbp, 500-600 kbp, 600-700 kbp, 700-800 kbp, 800-900 kbp, 900-1,000 kbp, 1-1.5 Mbp, 1.5-2 Mbp, 2-3 Mbp, 3-4 Mbp, 4-5 Mbp, 5-6 Mbp, 6-7 Mbp, 7-8 Mbp, 8-9 Mbp, 9-10 Mbp, or 10-20 Mbp. In some embodiments, the epigenetic target region set has a footprint of at least 20 Mbp.

i. Hypermethylation Variable Target Regions

In some embodiments, the epigenetic target region set comprises one or more hypermethylation variable target regions. In general, hypermethylation variable target regions refer to regions where an increase in the level of observed methylation indicates an increased likelihood that a sample (e.g., of cfDNA) contains DNA produced by neoplastic cells, such as tumor or cancer cells. For example, hypermethylation of promoters of tumor suppressor genes has been observed repeatedly. See, e.g., Kang et al., Genome Biol. 18:53 (2017) and references cited therein. In another example, as discussed above, hypermethylation variable target regions can include regions that do not necessarily differ in methylation in cancerous tissue relative to DNA from healthy tissue of the same type, but do differ in methylation (e.g., have more methylation) relative to cfDNA that is typical in healthy subjects.

An extensive discussion of methylation variable target regions in colorectal cancer is provided in Lam et al., Biochim Biophys Acta. 1866:106-20 (2016). These include VIM, SEPT9, ITGA4, OSM4, GATA4 and NDRG4. An exemplary set of hypermethylation variable target regions comprising the genes or portions thereof based on the colorectal cancer (CRC) studies is provided in Table 1. Many of these genes likely have relevance to cancers beyond colorectal cancer; for example, TP53 is widely recognized as a critically important tumor suppressor and hypermethylation-based inactivation of this gene may be a common oncogenic mechanism.

TABLE 1

Exemplary hypermethylation target regions (genes or portions thereof) based on CRC studies.

| Gene Name | Additional Gene | Chromosome |
|---|---|---|
| VIM | | chr10 |
| SEPT9 | | chr17 |
| CYCD2 | CCND | chr12 |
| TFPI2 | | chr7 |

TABLE 1-continued

Exemplary hypermethylation target regions (genes or portions thereof) based on CRC studies.

| Gene Name | Additional Gene | Chromosome |
|---|---|---|
| GATA4 | | chr8 |
| RARB2 | RARB | chr3 |
| p16INK4 | CDK | chr9 |
| MGMT | MGM | chr10 |
| APC | | chr5 |
| NDRG4 | | chr16 |
| HLTF | | chr3 |
| HPP1 | TMEF | chr2 |
| hMLH1 | MLH1 | chr3 |
| RASSF1 | RASS | chr3 |
| CDH13 | | chr16 |
| IGFBP3 | | chr7 |
| ITGA4 | | chr2 |

In some embodiments, the hypermethylation variable target regions comprise a plurality of genes or portions thereof listed in Table 1, e.g., at least 10%, 20%, 30%, 40%, 50%, 60%, 70%, 80%, 90%, or 100% of the genes or portions thereof listed in Table 1. For example, for each locus included as a target region, there may be one or more probes with a hybridization site that binds between the transcription start site and the stop codon (the last stop codon for genes that are alternatively spliced) of the gene. In some embodiments, the one or more probes bind within 300 bp upstream and/or downstream of the genes or portions thereof listed in Table 1, e.g., within 200 or 100 bp.

Methylation variable target regions in various types of lung cancer are discussed in detail, e.g., in Ooki et al., Clin. Cancer Res. 23:7141-52 (2017); Belinksy, Annu. Rev. Physiol. 77:453-74 (2015); Hulbert et al., Clin. Cancer Res. 23:1998-2005 (2017); Shi et al., BMC Genomics 18:901 (2017); Schneider et al., BMC Cancer. 11:102 (2011); Lissa et al., Transl Lung Cancer Res 5(5):492-504 (2016); Skvortsova et al., Br. J. Cancer. 94(10):1492-1495 (2006); Kim et al., Cancer Res. 61:3419-3424 (2001); Furonaka et al., Pathology International 55:303-309 (2005); Gomes et al., Rev. Port. Pneumol. 20:20-30 (2014); Kim et al., Oncogene. 20:1765-70 (2001); Hopkins-Donaldson et al., Cell Death Differ. 10:356-64 (2003); Kikuchi et al., Clin. Cancer Res. 11:2954-61 (2005); Heller et al., Oncogene 25:959-968 (2006); Licchesi et al., Carcinogenesis. 29:895-904 (2008); Guo et al., Clin. Cancer Res. 10:7917-24 (2004); Palmisano et al., Cancer Res. 63:4620-4625 (2003); and Toyooka et al., Cancer Res. 61:4556-4560, (2001). In an example, hypermethylation variable target regions can include regions that do not necessarily differ in methylation in cancerous tissue relative to DNA from healthy tissue of the same type, but do differ in methylation (e.g., have more methylation) relative to cfDNA that is typical in healthy subjects. Where, for example, the presence of a cancer results in increased cell death such as apoptosis of cells of the tissue type corresponding to the cancer, such a cancer can be detected at least in part using such hypermethylation variable target regions. In some embodiments, hypermethylation variable target regions include one or more genomic regions, where the cfDNA molecules in those regions do not differ in methylation state in cancer subjects relative to cfDNA from healthy subjects, but the presence/increased quantity of hypermethylated cfDNA in those regions is indicative of a particular tissue type (e.g., cancer origin) and is presented as cfDNA with increased apoptosis (e.g. tumor shedding) into circulation.

An exemplary set of hypermethylation variable target regions comprising genes or portions thereof based on the lung cancer studies is provided in Table 2. Many of these genes likely have relevance to cancers beyond lung cancer; for example, Casp8 (Caspase 8) is a key enzyme in programmed cell death and hypermethylation-based inactivation of this gene may be a common oncogenic mechanism not limited to lung cancer. Additionally, a number of genes appear in both Tables 1 and 2, indicating generality.

TABLE 2

Exemplary hypermethylation target regions (genes or portions thereof) based on lung cancer studies.

| Gene Name | Chromosome |
| --- | --- |
| MARCH11 | chr5 |
| TAC1 | chr7 |
| TCF21 | chr6 |
| SHOX2 | chr3 |
| p16 | chr3 |
| Casp8 | chr2 |
| CDH13 | chr16 |
| MGMT | chr10 |
| MLH1 | chr3 |
| MSH2 | chr2 |
| TSLC1 | chr11 |
| APC | chr5 |
| DKK1 | chr10 |
| DKK3 | chr11 |
| LKB1 | chr11 |
| WIF1 | chr12 |
| RUNX3 | chr1 |
| GATA4 | chr8 |
| GATA5 | chr20 |
| PAX5 | chr9 |
| E-Cadherin | chr16 |
| H-Cadherin | chr16 |

Any of the foregoing embodiments concerning target regions identified in Table 2 may be combined with any of the embodiments described above concerning target regions identified in Table 1. In some embodiments, the hypermethylation variable target regions comprise a plurality of genes or portions thereof listed in Table 1 or Table 2, e.g., at least 10%, 20%, 30%, 40%, 50%, 60%, 70%, 80%, 90%, or 100% of the genes or portions thereof listed in Table 1 or Table 2.

Additional hypermethylation target regions may be obtained, e.g., from the Cancer Genome Atlas. Kang et al., Genome Biology 18:53 (2017), describe construction of a probabilistic method called Cancer Locator using hypermethylation target regions from breast, colon, kidney, liver, and lung. In some embodiments, the hypermethylation target regions can be specific to one or more types of cancer. Accordingly, in some embodiments, the hypermethylation target regions include one, two, three, four, or five subsets of hypermethylation target regions that collectively show hypermethylation in one, two, three, four, or five of breast, colon, kidney, liver, and lung cancers.

In some embodiments, where different epigenetic target regions are captured from the first and second partitions, the epigenetic target regions captured from the first partition comprise hypermethylation variable target regions.

ii. Hypomethylation Variable Target Regions

Global hypomethylation is a commonly observed phenomenon in various cancers. See, e.g., Hon et al., Genome Res. 22:246-258 (2012) (breast cancer); Ehrlich, Epigenomics 1:239-259 (2009) (review article noting observations of hypomethylation in colon, ovarian, prostate, leukemia, hepatocellular, and cervical cancers). For example, regions such as repeated elements, e.g., LINE1 elements, Alu elements, centromeric tandem repeats, pericentromeric tandem repeats, and satellite DNA, and intergenic regions that are ordinarily methylated in healthy cells may show reduced methylation in tumor cells. Accordingly, in some embodiments, the epigenetic target region set includes hypomethylation variable target regions, where a decrease in the level of observed methylation indicates an increased likelihood that a sample (e.g., of cfDNA) contains DNA produced by neoplastic cells, such as tumor or cancer cells. In an example, hypomethylation variable target regions can include regions that do not necessarily differ in methylation state in cancerous tissue relative to DNA from healthy tissue of the same type, but do differ in methylation (e.g., are less methylated) relative to cfDNA that is typical in healthy subjects. Where, for example, the presence of a cancer results in increased cell death such as apoptosis of cells of the tissue type corresponding to the cancer, such a cancer can be detected at least in part using such hypomethylation variable target regions. In some embodiments, hypomethylation variable target regions include one or more genomic regions, where the cfDNA molecules in those regions do not differ in methylation state in cancer subjects relative to cfDNA from healthy subjects, but the presence/increased quantity of hypomethylated cfDNA in those regions is indicative of a particular tissue type (e.g., cancer origin) and is presented as cfDNA with increased apoptosis (e.g. tumor shedding) into circulation.

In some embodiments, hypomethylation variable target regions include repeated elements and/or intergenic regions. In some embodiments, repeated elements include one, two, three, four, or five of LINE1 elements, Alu elements, centromeric tandem repeats, pericentromeric tandem repeats, and/or satellite DNA.

Exemplary specific genomic regions that show cancer-associated hypomethylation include nucleotides 8403565-8953708 and 151104701-151106035 of human chromosome 1, e.g., according to the hg19 or hg38 human genome construct. In some embodiments, the hypomethylation variable target regions overlap or comprise one or both of these regions.

In some embodiments, where different epigenetic target regions are captured from the first and second partitions, the epigenetic target regions captured from the second partition comprise hypomethylation variable target regions.

iii. CTCF Binding Regions

CTCF is a DNA-binding protein that contributes to chromatin organization and often colocalizes with cohesin. Perturbation of CTCF binding sites has been reported in a variety of different cancers. See, e.g., Katainen et al., Nature Genetics, doi:10.1038/ng.3335, published online 8 Jun. 2015; Guo et al., Nat. Commun. 9:1520 (2018). CTCF binding results in recognizable patterns in cfDNA that can be detected by sequencing, e.g., through fragment length analysis. For example, details regarding sequencing-based fragment length analysis are provided in Snyder et al., Cell 164:57-68 (2016); WO 2018/009723; and US20170211143A1, each of which are incorporated herein by reference.

Thus, perturbations of CTCF binding result in variation in the fragmentation patterns of cfDNA. As such, CTCF binding sites represent a type of fragmentation variable target regions.

There are many known CTCF binding sites. See, e.g., the CTCFBSDB (CTCF Binding Site Database), available on the Internet at insulatordb.uthsc.edu/; Cuddapah et al., Genome Res. 19:24-32 (2009); Martin et al., Nat. Struct. Mol. Biol. 18:708-14 (2011); Rhee et al., Cell. 147:1408-19

(2011), each of which are incorporated by reference. Exemplary CTCF binding sites are at nucleotides 56014955-56016161 on chromosome 8 and nucleotides 95359169-95360473 on chromosome 13, e.g., according to the hg19 or hg38 human genome construct.

Accordingly, in some embodiments, the epigenetic target region set includes CTCF binding regions. In some embodiments, the CTCF binding regions comprise at least 10, 20, 50, 100, 200, or 500 CTCF binding regions, or 10-20, 20-50, 50-100, 100-200, 200-500, or 500-1000 CTCF binding regions, e.g., such as CTCF binding regions described above or in one or more of CTCFBSDB or the Cuddapah et al., Martin et al., or Rhee et al. articles cited above.

In some embodiments, at least some of the CTCF sites can be methylated or unmethylated, wherein the methylation state is correlated with the whether or not the cell is a cancer cell. In some embodiments, the epigenetic target region set comprises at least 100 bp, at least 200 bp, at least 300 bp, at least 400 bp, at least 500 bp, at least 750 bp, at least 1000 bp upstream and/or downstream regions of the CTCF binding sites.

iv. Transcription Start Sites

Transcription start sites may also show perturbations in neoplastic cells. For example, nucleosome organization at various transcription start sites in healthy cells of the hematopoietic lineage—which contributes substantially to cfDNA in healthy individuals— may differ from nucleosome organization at those transcription start sites in neoplastic cells. This results in different cfDNA patterns that can be detected by sequencing, for example, as discussed generally in Snyder et al., Cell 164:57-68 (2016); WO 2018/009723; and US20170211143A1. In another example, transcription start sites that do not necessarily differ epigenetically in cancerous tissue relative to DNA from healthy tissue of the same type, but do differ epigenetically (e.g., with respect to nucleosome organization) relative to cfDNA that is typical in healthy subjects. Where, for example, the presence of a cancer results in increased cell death such as apoptosis of cells of the tissue type corresponding to the cancer, such a cancer can be detected at least in part using such transcription start sites.

Thus, perturbations of transcription start sites also result in variation in the fragmentation patterns of cfDNA. As such, transcription start sites also represent a type of fragmentation variable target regions.

Human transcriptional start sites are available from DBTSS (DataBase of Human Transcription Start Sites), available on the Internet at dbtss.hgc.jp and described in Yamashita et al., Nucleic Acids Res. 34 (Database issue): D86-D89 (2006), which is incorporated herein by reference.

Accordingly, in some embodiments, the epigenetic target region set includes transcriptional start sites. In some embodiments, the transcriptional start sites comprise at least 10, 20, 50, 100, 200, or 500 transcriptional start sites, or 10-20, 20-50, 50-100, 100-200, 200-500, or 500-1000 transcriptional start sites, e.g., such as transcriptional start sites listed in DBTSS. In some embodiments, at least some of the transcription start sites can be methylated or unmethylated, wherein the methylation state is correlated with the whether or not the cell is a cancer cell. In some embodiments, the epigenetic target region set comprises at least 100 bp, at least 200 bp, at least 300 bp, at least 400 bp, at least 500 bp, at least 750 bp, at least 1000 bp upstream and/or downstream regions of the transcription start sites.

v. Copy Number Variations; Focal Amplifications

Although copy number variations such as focal amplifications are somatic mutations, they can be detected by sequencing based on read frequency in a manner analogous to approaches for detecting certain epigenetic changes such as changes in methylation. As such, regions that may show copy number variations such as focal amplifications in cancer can be included in the epigenetic target region set and may comprise one or more of AR, BRAF, CCND1, CCND2, CCNE1, CDK4, CDK6, EGFR, ERBB2, FGFR1, FGFR2, KIT, KRAS, MET, MYC, PDGFRA, PIK3CA, and RAF1. For example, in some embodiments, the epigenetic target region set comprises at least 2, 3, 4, 5, 6, 7, 8, 9, 10, 11, 12, 13, 14, 15, 16, 17, or 18 of the foregoing targets.

iv. Methylation Control Regions

It can be useful to include control regions to facilitate data validation. In some embodiments, the epigenetic target region set includes control regions that are expected to be methylated or unmethylated in essentially all samples, regardless of whether the DNA is derived from a cancer cell or a normal cell. In some embodiments, the epigenetic target region set includes control hypomethylated regions that are expected to be hypomethylated in essentially all samples. In some embodiments, the epigenetic target region set includes control hypermethylated regions that are expected to be hypermethylated in essentially all samples.

b. Sequence-Variable Target Region Set

In some embodiments, the sequence-variable target region set comprises a plurality of regions known to undergo somatic mutations in cancer (referred to herein as cancer-associated mutations). Accordingly, methods may comprise determining whether cfDNA molecules corresponding to the sequence-variable target region set comprise cancer-associated mutations.

In some embodiments, the sequence-variable target region set targets a plurality of different genes or genomic regions ("panel") selected such that a determined proportion of subjects having a cancer exhibits a genetic variant or tumor marker in one or more different genes or genomic regions in the panel. The panel may be selected to limit a region for sequencing to a fixed number of base pairs. The panel may be selected to sequence a desired amount of DNA, e.g., by adjusting the affinity and/or amount of the probes as described elsewhere herein. The panel may be further selected to achieve a desired sequence read depth. The panel may be selected to achieve a desired sequence read depth or sequence read coverage for an amount of sequenced base pairs. The panel may be selected to achieve a theoretical sensitivity, a theoretical specificity, and/or a theoretical accuracy for detecting one or more genetic variants in a sample.

Probes for detecting the panel of regions can include those for detecting genomic regions of interest (hotspot regions) as well as nucleosome-aware probes (e.g., KRAS codons 12 and 13) and may be designed to optimize capture based on analysis of cfDNA coverage and fragment size variation impacted by nucleosome binding patterns and GC sequence composition. Regions used herein can also include non-hotspot regions optimized based on nucleosome positions and GC models.

Examples of listings of genomic locations of interest may be found in Table 3 and Table 4. In some embodiments, a sequence-variable target region set used in the methods of the present disclosure comprises at least a portion of at least 5, at least 10, at least 15, at least 20, at least 25, at least 30, at least 35, at least 40, at least 45, at least 50, at least 55, at least 60, at least 65, or 70 of the genes of Table 3. In some embodiments, a sequence-variable target region set used in the methods of the present disclosure comprises at least 5, at least 10, at least 15, at least 20, at least 25, at least 30, at least 35, at least 40, at least 45, at least 50, at least 55, at least 60, at least 65, or 70 of the SNVs of Table 3. In some embodiments, a sequence-variable target region set used in the methods of the present disclosure comprises at least 1, at least 2, at least 3, at least 4, at least 5, or 6 of the fusions of Table 3. In some embodiments, a sequence-variable target region set used in the methods of the present disclosure comprise at least a portion of at least 1, at least 2, or 3 of the indels of Table 3. In some embodiments, a sequence-variable target region set used in the methods of the present disclosure comprises at least a portion of at least 5, at least 10, at least 15, at least 20, at least 25, at least 30, at least 35, at least 40, at least 45, at least 50, at least 55, at least 60, at least 65, at least 70, or 73 of the genes of Table 4. In some embodiments, a sequence-variable target region set used in the methods of the present disclosure comprises at least 5, at least 10, at least 15, at least 20, at least 25, at least 30, at least 35, at least 40, at least 45, at least 50, at least 55, at least 60, at least 65, at least 70, or 73 of the SNVs of Table 4. In some embodiments, a sequence-variable target region set used in the methods of the present disclosure comprises at least 1, at least 2, at least 3, at least 4, at least 5, or 6 of the fusions of Table 4. In some embodiments, a sequence-variable target region set used in the methods of the present disclosure comprises at least a portion of at least 1, at least 2, at least 3, at least 4, at least 5, at least 6, at least 7, at least 8, at least 9, at least 10, at least 11, at least 12, at least 13, at least 14, at least 15, at least 16, at least 17, or 18 of the indels of Table 4. Each of these genomic locations of interest may be identified as a backbone region or hot-spot region for a given panel. An example of a listing of hot-spot genomic locations of interest may be found in Table 5. The coordinates in Table 5 are based on the hg19 assembly of the human genome, but one skilled in the art will be familiar with other assemblies and can identify coordinate sets corresponding to the indicated exons, introns, codons, etc. in an assembly of their choice. In some embodiments, a sequence-variable target region set used in the methods of the present disclosure comprises at least a portion of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 of the genes of Table 5. Each hot-spot genomic region is listed with several characteristics, including the associated gene, chromosome on which it resides, the start and stop position of the genome representing the gene's locus, the length of the gene's locus in base pairs, the exons covered by the gene, and the critical feature (e.g., type of mutation) that a given genomic region of interest may seek to capture.

TABLE 3

| Point Mutations (SNVs) and Indels | | | | | | Fusions |
|---|---|---|---|---|---|---|
| AKT1 | ALK | APC | AR | ARAF | ARID1A | ALK |
| ATM | BRAF | BRCA1 | BRCA2 | CCND1 | CCND2 | FGFR2 |
| CCNE1 | CDH1 | CDK4 | CDK6 | CDKN2A | CDKN2B | FGFR3 |
| CTNNB1 | EGFR | ERBB2 | ESR1 | EZH2 | FBXW7 | NTRK1 |
| FGFR1 | FGFR2 | FGFR3 | GATA3 | GNA11 | GNAQ | RET |
| GNAS | HNF1A | HRAS | IDH1 | IDH2 | JAK2 | ROS1 |
| JAK3 | KIT | KRAS | MAP2K1 | MAP2K2 | MET | |
| MLH1 | MPL | MYC | NF1 | NFE2L2 | NOTCH1 | |
| NPM1 | NRAS | NTRK1 | PDGFRA | PIK3CA | PTEN | |
| PTPN11 | RAF1 | RB1 | RET | RHEB | RHOA | |
| RIT1 | ROS1 | SMAD4 | SMO | SRC | STK11 | |
| TERT | TP53 | TSC1 | VHL | | | |

TABLE 4

| Point Mutations (SNVs) and Indels | | | | | | Fusions |
|---|---|---|---|---|---|---|
| AKT1 | ALK | APC | AR | ARAF | ARID1A | ALK |
| ATM | BRAF | BRCA1 | BRCA2 | CCND1 | CCND2 | FGFR2 |
| CCNE1 | CDH1 | CDK4 | CDK6 | CDKN2A | DDR2 | FGFR3 |
| CTNNB1 | EGFR | ERBB2 | ESR1 | EZH2 | FBXW7 | NTRK1 |
| FGFR1 | FGFR2 | FGFR3 | GATA3 | GNA11 | GNAQ | RET |
| GNAS | HNF1A | HRAS | IDH1 | IDH2 | JAK2 | ROS1 |
| JAK3 | KIT | KRAS | MAP2K1 | MAP2K2 | MET | |
| MLH1 | MPL | MYC | NF1 | NFE2L2 | NOTCH1 | |
| NPM1 | NRAS | NTRK1 | PDGFRA | PIK3CA | PTEN | |
| PTPN11 | RAF1 | RB1 | RET | RHEB | RHOA | |
| RIT1 | ROS1 | SMAD4 | SMO | MAPK1 | STK11 | |
| TERT | TP53 | TSC1 | VHL | MAPK3 | MTOR | |
| NTRK3 | | | | | | |

TABLE 5

| Gene | Chromosome | Start Position | Stop Position | Length (bp) | Exons/Introns Covered | Feature |
|---|---|---|---|---|---|---|
| ALK | chr2 | 29446405 | 29446655 | 250 | intron 19 | Fusion |
| ALK | chr2 | 29446062 | 29446197 | 135 | intron 20 | Fusion |
| ALK | chr2 | 29446198 | 29446404 | 206 | exon 20 | Fusion |

TABLE 5-continued

| Gene | Chromosome | Start Position | Stop Position | Length (bp) | Exons/Introns Covered | Feature |
|---|---|---|---|---|---|---|
| ALK | chr2 | 29447353 | 29447473 | 120 | intron 19 | Fusion |
| ALK | chr2 | 29447614 | 29448316 | 702 | intron 19 | Fusion |
| ALK | chr2 | 29448317 | 29448441 | 124 | exon 19 | Fusion |
| ALK | chr2 | 29449366 | 29449777 | 411 | intron 18 | Fusion |
| ALK | chr2 | 29449778 | 29449950 | 172 | exon 18 | Fusion |
| BRAF | chr7 | 140453064 | 140453203 | 139 | exon 15 | BRAF V600 |
| CTNNB1 | chr3 | 41266007 | 41266254 | 247 | exon 3 | S37 |
| EGFR | chr7 | 55240528 | 55240827 | 299 | exons 18 and 19 | G719 and deletions |
| EGFR | chr7 | 55241603 | 55241746 | 143 | exon 20 | Insertions/T790M |
| EGFR | chr7 | 55242404 | 55242523 | 119 | exon 21 | L858R |
| ERBB2 | chr17 | 37880952 | 37881174 | 222 | exon 20 | Insertions |
| ESR1 | chr6 | 152419857 | 152420111 | 254 | exon 10 | V534, P535, L536, Y537, D538 |
| FGFR2 | chr10 | 123279482 | 123279693 | 211 | exon 6 | S252 |
| GATA3 | chr10 | 8111426 | 8111571 | 145 | exon 5 | SS/Indels |
| GATA3 | chr10 | 8115692 | 8116002 | 310 | exon 6 | SS/Indels |
| GNAS | chr20 | 57484395 | 57484488 | 93 | exon 8 | R844 |
| IDH1 | chr2 | 209113083 | 209113394 | 311 | exon 4 | R132 |
| IDH2 | chr15 | 90631809 | 90631989 | 180 | exon 4 | R140, R172 |
| KIT | chr4 | 55524171 | 55524258 | 87 | exon 1 | |
| KIT | chr4 | 55561667 | 55561957 | 290 | exon 2 | |
| KIT | chr4 | 55564439 | 55564741 | 302 | exon 3 | |
| KIT | chr4 | 55565785 | 55565942 | 157 | exon 4 | |
| KIT | chr4 | 55569879 | 55570068 | 189 | exon 5 | |
| KIT | chr4 | 55573253 | 55573463 | 210 | exon 6 | |
| KIT | chr4 | 55575579 | 55575719 | 140 | exon 7 | |
| KIT | chr4 | 55589739 | 55589874 | 135 | exon 8 | |
| KIT | chr4 | 55592012 | 55592226 | 214 | exon 9 | |
| KIT | chr4 | 55593373 | 55593718 | 345 | exons 10 and 11 | 557, 559, 560, 576 |
| KIT | chr4 | 55593978 | 55594297 | 319 | exons 12 and 13 | V654 |
| KIT | chr4 | 55595490 | 55595661 | 171 | exon 14 | T670, S709 |
| KIT | chr4 | 55597483 | 55597595 | 112 | exon 15 | D716 |
| KIT | chr4 | 55598026 | 55598174 | 148 | exon 16 | L783 |
| KIT | chr4 | 55599225 | 55599368 | 143 | exon 17 | C809, R815, D816, L818, D820, S821F, N822, Y823 |
| KIT | chr4 | 55602653 | 55602785 | 132 | exon 18 | A829P |
| KIT | chr4 | 55602876 | 55602996 | 120 | exon 19 | |
| KIT | chr4 | 55603330 | 55603456 | 126 | exon 20 | |
| KIT | chr4 | 55604584 | 55604733 | 149 | exon 21 | |
| KRAS | chr12 | 25378537 | 25378717 | 180 | exon 4 | A146 |
| KRAS | chr12 | 25380157 | 25380356 | 199 | exon 3 | Q61 |
| KRAS | chr12 | 25398197 | 25398328 | 131 | exon 2 | G12/G13 |
| MET | chr7 | 116411535 | 116412255 | 720 | exon 13, exon 14, intron 13, intron 14 | MET exon 14 SS |
| NRAS | chr1 | 115256410 | 115256609 | 199 | exon 3 | Q61 |
| NRAS | chr1 | 115258660 | 115258791 | 131 | exon 2 | G12/G13 |
| PIK3CA | chr3 | 178935987 | 178936132 | 145 | exon 10 | E545K |
| PIK3CA | chr3 | 178951871 | 178952162 | 291 | exon 21 | H1047R |
| PTEN | chr10 | 89692759 | 89693018 | 259 | exon 5 | R130 |
| SMAD4 | chr18 | 48604616 | 48604849 | 233 | exon 12 | D537 |
| TERT | chr5 | 1294841 | 1295512 | 671 | promoter | chr5: 1295228 |
| TP53 | chr17 | 7573916 | 7574043 | 127 | exon 11 | Q331, R337, R342 |
| TP53 | chr17 | 7577008 | 7577165 | 157 | exon 8 | R273 |
| TP53 | chr17 | 7577488 | 7577618 | 130 | exon 7 | R248 |
| TP53 | chr17 | 7578127 | 7578299 | 172 | exon 6 | R213/Y220 |
| TP53 | chr17 | 7578360 | 7578564 | 204 | exon 5 | R175/Deletions |
| TP53 | chr17 | 7579301 | 7579600 | 299 | exon 4 | |
| | | | | 12574 (total target region) | | |
| | | | | 16330 (total probe coverage) | | |

Additionally, or alternatively, suitable target region sets are available from the literature. For example, Gale et al., PLoS One 13: e0194630 (2018), which is incorporated herein by reference, describes a panel of 35 cancer-related gene targets that can be used as part or all of a sequence-variable target region set. These 35 targets are AKT1, ALK, BRAF, CCND1, CDK2A, CTNNB1, EGFR, ERBB2, ESR1, FGFR1, FGFR2, FGFR3, FOXL2, GATA3, GNA11, GNAQ, GNAS, HRAS, IDH1, IDH2, KIT, KRAS, MED12, MET, MYC, NFE2L2, NRAS, PDGFRA, PIK3CA, PPP2R1A, PTEN, RET, STK11, TP53, and U2AF1.

In some embodiments, the sequence-variable target region set comprises target regions from at least 10, 20, 30, or 35 cancer-related genes, such as the cancer-related genes listed above.

In some embodiments, the sequence-variable target region set has a footprint of at least 50 kbp, e.g., at least 100 kbp, at least 200 kbp, at least 300 kbp, or at least 400 kbp. In some embodiments, the sequence-variable target region set has a footprint in the range of 100-2000 kbp, e.g., 100-200 kbp, 200-300 kbp, 300-400 kbp, 400-500 kbp, 500-600 kbp, 600-700 kbp, 700-800 kbp, 800-900 kbp, 900-1,000 kbp, 1-1.5 Mbp or 1.5-2 Mbp. In some embodiments, the sequence-variable target region set has a footprint of at least 2 Mbp.

c. Collections of Target-Specific Probes

In some embodiments, a collection of target-specific probes is used in methods described herein. In some embodiments, the collection of target-specific probes comprises target-binding probes specific for a sequence-variable target region set and target-binding probes specific for an epigenetic target region set. In some embodiments, the capture yield of the target-binding probes specific for the sequence-variable target region set is higher (e.g., at least 2-fold higher) than the capture yield of the target-binding probes specific for the epigenetic target region set. In some embodiments, the collection of target-specific probes is configured to have a capture yield specific for the sequence-variable target region set higher (e.g., at least 2-fold higher) than its capture yield specific for the epigenetic target region set.

In some embodiments, the capture yield of the target-binding probes specific for the sequence-variable target region set is at least 1.25-, 1.5-, 1.75-, 2-, 2.25-, 2.5-, 2.75-, 3-, 3.5-, 4-, 4.5-, 5-, 6-, 7-, 8-, 9-, 10-, 11-, 12-, 13-, 14-, or 15-fold higher than the capture yield of the target-binding probes specific for the epigenetic target region set. In some embodiments, the capture yield of the target-binding probes specific for the sequence-variable target region set is 1.25- to 1.5-, 1.5- to 1.75-, 1.75- to 2-, 2- to 2.25-, 2.25- to 2.5-, 2.5- to 2.75-, 2.75- to 3-, 3- to 3.5-, 3.5- to 4-, 4- to 4.5-, 4.5- to 5-, 5- to 5.5-, 5.5- to 6-, 6- to 7-, 7- to 8-, 8- to 9-, 9- to 10-, 10- to 11-, 11- to 12-, 13- to 14-, or 14- to 15-fold higher than the capture yield of the target-binding probes specific for the epigenetic target region set.

In some embodiments, the collection of target-specific probes is configured to have a capture yield specific for the sequence-variable target region set at least 1.25-, 1.5-, 1.75-, 2-, 2.25-, 2.5-, 2.75-, 3-, 3.5-, 4-, 4.5-, 5-, 6-, 7-, 8-, 9-, 10-, 11-, 12-, 13-, 14-, or 15-fold higher than its capture yield for the epigenetic target region set. In some embodiments, the collection of target-specific probes is configured to have a capture yield specific for the sequence-variable target region set is 1.25- to 1.5-, 1.5- to 1.75-, 1.75- to 2-, 2- to 2.25-, 2.25- to 2.5-, 2.5- to 2.75-, 2.75- to 3-, 3- to 3.5-, 3.5- to 4-, 4- to 4.5-, 4.5- to 5-, 5- to 5.5-, 5.5- to 6-, 6- to 7-, 7- to 8-, 8- to 9-, 9- to 10-, 10- to 11-, 11- to 12-, 13- to 14-, or 14- to 15-fold higher than its capture yield specific for the epigenetic target region set.

The collection of probes can be configured to provide higher capture yields for the sequence-variable target region set in various ways, including concentration, different lengths and/or chemistries (e.g., that affect affinity), and combinations thereof. Affinity can be modulated by adjusting probe length and/or including nucleotide modifications as discussed below.

In some embodiments, the target-specific probes specific for the sequence-variable target region set are present at a higher concentration than the target-specific probes specific for the epigenetic target region set. In some embodiments, concentration of the target-binding probes specific for the sequence-variable target region set is at least 1.25-, 1.5-, 1.75-, 2-, 2.25-, 2.5-, 2.75-, 3-, 3.5-, 4-, 4.5-, 5-, 6-, 7-, 8-, 9-, 10-, 11-, 12-, 13-, 14-, or 15-fold higher than the concentration of the target-binding probes specific for the epigenetic target region set. In some embodiments, the concentration of the target-binding probes specific for the sequence-variable target region set is 1.25- to 1.5-, 1.5- to 1.75-, 1.75- to 2-, 2- to 2.25-, 2.25- to 2.5-, 2.5- to 2.75-, 2.75- to 3-, 3- to 3.5-, 3.5- to 4-, 4- to 4.5-, 4.5- to 5-, 5- to 5.5-, 5.5- to 6-, 6- to 7-, 7- to 8-, 8- to 9-, 9- to 10-, 10- to 11-, 11- to 12-, 13- to 14-, or 14- to 15-fold higher than the concentration of the target-binding probes specific for the epigenetic target region set. In such embodiments, concentration may refer to the average mass per volume concentration of individual probes in each set.

In some embodiments, the target-specific probes specific for the sequence-variable target region set have a higher affinity for their targets than the target-specific probes specific for the epigenetic target region set. Affinity can be modulated in any way known to those skilled in the art, including by using different probe chemistries. For example, certain nucleotide modifications, such as cytosine 5-methylation (in certain sequence contexts), modifications that provide a heteroatom at the 2' sugar position, and LNA nucleotides, can increase stability of double-stranded nucleic acids, indicating that oligonucleotides with such modifications have relatively higher affinity for their complementary sequences. See, e.g., Severin et al., Nucleic Acids Res. 39: 8740-8751 (2011); Freier et al., Nucleic Acids Res. 25: 4429-4443 (1997); U.S. Pat. No. 9,738,894. Also, longer sequence lengths will generally provide increased affinity. Other nucleotide modifications, such as the substitution of the nucleobase hypoxanthine for guanine, reduce affinity by reducing the amount of hydrogen bonding between the oligonucleotide and its complementary sequence. In some embodiments, the target-specific probes specific for the sequence-variable target region set have modifications that increase their affinity for their targets. In some embodiments, alternatively or additionally, the target-specific probes specific for the epigenetic target region set have modifications that decrease their affinity for their targets. In some embodiments, the target-specific probes specific for the sequence-variable target region set have longer average lengths and/or higher average melting temperatures than the target-specific probes specific for the epigenetic target region set. These embodiments may be combined with each other and/or with differences in concentration as discussed above to achieve a desired fold difference in capture yield, such as any fold difference or range thereof described above.

In some embodiments, the target-specific probes comprise a capture moiety. The capture moiety may be any of the capture moieties described herein, e.g., biotin. In some embodiments, the target-specific probes are linked to a solid support, e.g., covalently or noncovalently such as through the interaction of a binding pair of capture moieties. In some embodiments, the solid support is a bead, such as a magnetic bead.

In some embodiments, the target-specific probes specific for the sequence-variable target region set and/or the target-specific probes specific for the epigenetic target region set are a bait set as discussed above, e.g., probes comprising capture moieties and sequences selected to tile across a panel of regions, such as genes.

In some embodiments, the target-specific probes are provided in a single composition. The single composition may be a solution (liquid or frozen). Alternatively, it may be a lyophilizate.

Alternatively, the target-specific probes may be provided as a plurality of compositions, e.g., comprising a first composition comprising probes specific for the epigenetic target region set and a second composition comprising probes specific for the sequence-variable target region set. These probes may be mixed in appropriate proportions to provide a combined probe composition with any of the foregoing fold differences in concentration and/or capture yield. Alternatively, they may be used in separate capture procedures (e.g., with aliquots of a sample or sequentially with the same sample) to provide first and second compositions comprising captured epigenetic target regions and sequence-variable target regions, respectively.

ii. Probes Specific for Epigenetic Target Regions

The probes for the epigenetic target region set may comprise probes specific for one or more types of target regions likely to differentiate DNA from neoplastic (e.g., tumor or cancer) cells from healthy cells, e.g., non-neoplastic circulating cells. Exemplary types of such regions are discussed in detail herein, e.g., in the sections above concerning captured sets. The probes for the epigenetic target region set may also comprise probes for one or more control regions, e.g., as described herein.

In some embodiments, the probes for the epigenetic target region set have a footprint of at least 100 kbp, e.g., at least 200 kbp, at least 300 kbp, or at least 400 kbp. In some embodiments, the epigenetic target region set has a footprint in the range of 100-20 Mbp, e.g., 100-200 kbp, 200-300 kbp, 300-400 kbp, 400-500 kbp, 500-600 kbp, 600-700 kbp, 700-800 kbp, 800-900 kbp, 900-1,000 kbp, 1-1.5 Mbp, 1.5-2 Mbp, 2-3 Mbp, 3-4 Mbp, 4-5 Mbp, 5-6 Mbp, 6-7 Mbp, 7-8 Mbp, 8-9 Mbp, 9-10 Mbp, or 10-20 Mbp. In some embodiments, the epigenetic target region set has a footprint of at least 20 Mbp.

a. Hypermethylation Variable Target Regions

In some embodiments, the probes for the epigenetic target region set comprise probes specific for one or more hypermethylation variable target regions. Hypermethylation variable target regions may also be referred to herein as hypermethylated DMRs (differentially methylated regions). The hypermethylation variable target regions may be any of those set forth above. For example, in some embodiments, the probes specific for hypermethylation variable target regions comprise probes specific for a plurality of loci listed in Table 1, e.g., at least 10%, 20%, 30%, 40%, 50%, 60%, 70%, 80%, 90%, or 100% of the loci listed in Table 1. In some embodiments, the probes specific for hypermethylation variable target regions comprise probes specific for a plurality of loci listed in Table 2, e.g., at least 10%, 20%, 30%, 40%, 50%, 60%, 70%, 80%, 90%, or 100% of the loci listed in Table 2. In some embodiments, the probes specific for hypermethylation variable target regions comprise probes specific for a plurality of loci listed in Table 1 or Table 2, e.g., at least 10%, 20%, 30%, 40%, 50%, 60%, 70%, 80%, 90%, or 100% of the loci listed in Table 1 or Table 2. In some embodiments, for each locus included as a target region, there may be one or more probes with a hybridization site that binds between the transcription start site and the stop codon (the last stop codon for genes that are alternatively spliced) of the gene. In some embodiments, the one or more probes bind within 300 bp of the listed position, e.g., within 200 or 100 bp. In some embodiments, a probe has a hybridization site overlapping the position listed above. In some embodiments, the probes specific for the hypermethylation target regions include probes specific for one, two, three, four, or five subsets of hypermethylation target regions that collectively show hypermethylation in one, two, three, four, or five of breast, colon, kidney, liver, and lung cancers.

b. Hypomethylation Variable Target Regions

In some embodiments, the probes for the epigenetic target region set comprise probes specific for one or more hypomethylation variable target regions. Hypomethylation variable target regions may also be referred to herein as hypomethylated DMRs (differentially methylated regions). The hypomethylation variable target regions may be any of those set forth above. For example, the probes specific for one or more hypomethylation variable target regions may include probes for regions such as repeated elements, e.g., LINE1 elements, Alu elements, centromeric tandem repeats, pericentromeric tandem repeats, and satellite DNA, and intergenic regions that are ordinarily methylated in healthy cells may show reduced methylation in tumor cells.

In some embodiments, probes specific for hypomethylation variable target regions include probes specific for repeated elements and/or intergenic regions. In some embodiments, probes specific for repeated elements include probes specific for one, two, three, four, or five of LINE1 elements, Alu elements, centromeric tandem repeats, pericentromeric tandem repeats, and/or satellite DNA.

Exemplary probes specific for genomic regions that show cancer-associated hypomethylation include probes specific for nucleotides 8403565-8953708 and/or 151104701-151106035 of human chromosome 1. In some embodiments, the probes specific for hypomethylation variable target regions include probes specific for regions overlapping or comprising nucleotides 8403565-8953708 and/or 151104701-151106035 of human chromosome 1.

c. CTCF Binding Regions

In some embodiments, the probes for the epigenetic target region set include probes specific for CTCF binding regions. In some embodiments, the probes specific for CTCF binding regions comprise probes specific for at least 10, 20, 50, 100, 200, or 500 CTCF binding regions, or 10-20, 20-50, 50-100, 100-200, 200-500, or 500-1000 CTCF binding regions, e.g., such as CTCF binding regions described above or in one or more of CTCFBSDB or the Cuddapah et al., Martin et al., or Rhee et al. articles cited above. In some embodiments, the probes for the epigenetic target region set comprise at least 100 bp, at least 200 bp at least 300 bp, at least 400 bp, at least 500 bp, at least 750 bp, or at least 1000 bp upstream and downstream regions of the CTCF binding sites.

d. Transcription Start Sites

In some embodiments, the probes for the epigenetic target region set include probes specific for transcriptional start sites. In some embodiments, the probes specific for transcriptional start sites comprise probes specific for at least 10, 20, 50, 100, 200, or 500 transcriptional start sites, or 10-20, 20-50, 50-100, 100-200, 200-500, or 500-1000 transcriptional start sites, e.g., such as transcriptional start sites listed in DBTSS. In some embodiments, the probes for the epigenetic target region set comprise probes for sequences at least 100 bp, at least 200 bp, at least 300 bp, at least 400 bp, at least 500 bp, at least 750 bp, or at least 1000 bp upstream and downstream of the transcriptional start sites.

e. Focal Amplifications

As noted above, although focal amplifications are somatic mutations, they can be detected by sequencing based on read frequency in a manner analogous to approaches for detecting certain epigenetic changes such as changes in methylation. As such, regions that may show focal amplifications in cancer can be included in the epigenetic target region set, as discussed above. In some embodiments, the probes specific for the epigenetic target region set include probes specific for focal amplifications. In some embodiments, the probes specific for focal amplifications include probes specific for one or more of AR, BRAF, CCND1, CCND2, CCNE1, CDK4, CDK6, EGFR, ERBB2, FGFR1, FGFR2, KIT, KRAS, MET, MYC, PDGFRA, PIK3CA, and RAF1. For example, in some embodiments, the probes specific for focal amplifications include probes specific for one or more of at least 2, 3, 4, 5, 6, 7, 8, 9, 10, 11, 12, 13, 14, 15, 16, 17, or 18 of the foregoing targets.

f. Control Regions

It can be useful to include control regions to facilitate data validation. In some embodiments, the probes specific for the epigenetic target region set include probes specific for control methylated regions that are expected to be methylated in essentially all samples. In some embodiments, the probes specific for the epigenetic target region set include probes specific for control hypomethylated regions that are expected to be hypomethylated in essentially all samples.

ii. Probes Specific for Sequence-Variable Target Regions

The probes for the sequence-variable target region set may comprise probes specific for a plurality of regions known to undergo somatic mutations in cancer. The probes may be specific for any sequence-variable target region set described herein. Exemplary sequence-variable target region sets are discussed in detail herein, e.g., in the sections above concerning captured sets.

In some embodiments, the sequence-variable target region probe set has a footprint of at least 0.5 kb, e.g., at least 1 kb, at least 2 kb, at least 5 kb, at least 10 kb, at least 20 kb, at least 30 kb, or at least 40 kb. In some embodiments, the epigenetic target region probe set has a footprint in the range of 0.5-100 kb, e.g., 0.5-2 kb, 2-10 kb, 10-20 kb, 20-30 kb, 30-40 kb, 40-50 kb, 50-60 kb, 60-70 kb, 70-80 kb, 80-90 kb, and 90-100 kb. In some embodiments, the sequence-variable target region probe set has a footprint of at least 50 kbp, e.g., at least 100 kbp, at least 200 kbp, at least 300 kbp, or at least 400 kbp. In some embodiments, the sequence-variable target region probe set has a footprint in the range of 100-2000 kbp, e.g., 100-200 kbp, 200-300 kbp, 300-400 kbp, 400-500 kbp, 500-600 kbp, 600-700 kbp, 700-800 kbp, 800-900 kbp, 900-1,000 kbp, 1-1.5 Mbp or 1.5-2 Mbp. In some embodiments, the sequence-variable target region set has a footprint of at least 2 Mbp.

In some embodiments, probes specific for the sequence-variable target region set comprise probes specific for at least a portion of at least 5, at least 10, at least 15, at least 20, at least 25, at least 30, at least 35, at least 40, at least 45, at least 50, at least 55, at least 60, at least 65, or at least 70 of the genes of Table 3. In some embodiments, probes specific for the sequence-variable target region set comprise probes specific for the at least 5, at least 10, at least 15, at least 20, at least 25, at least 30, at least 35, at least 40, at least 45, at least 50, at least 55, at least 60, at least 65, or 70 of the SNVs of Table 3. In some embodiments, probes specific for the sequence-variable target region set comprise probes specific for at least 1, at least 2, at least 3, at least 4, at least 5, or 6 of the fusions of Table 3. In some embodiments, probes specific for the sequence-variable target region set comprise probes specific for at least a portion of at least 1, at least 2, or 3 of the indels of Table 3. In some embodiments, probes specific for the sequence-variable target region set comprise probes specific for at least a portion of at least 5, at least 10, at least 15, at least 20, at least 25, at least 30, at least 35, at least 40, at least 45, at least 50, at least 55, at least 60, at least 65, at least 70, or 73 of the genes of Table 4. In some embodiments, probes specific for the sequence-variable target region set comprise probes specific for at least 5, at least 10, at least 15, at least 20, at least 25, at least 30, at least 35, at least 40, at least 45, at least 50, at least 55, at least 60, at least 65, at least 70, or 73 of the SNVs of Table 4. In some embodiments, probes specific for the sequence-variable target region set comprise probes specific for at least 1, at least 2, at least 3, at least 4, at least 5, or 6 of the fusions of Table 4. In some embodiments, probes specific for the sequence-variable target region set comprise probes specific for at least a portion of at least 1, at least 2, at least 3, at least 4, at least 5, at least 6, at least 7, at least 8, at least 9, at least 10, at least 11, at least 12, at least 13, at least 14, at least 15, at least 16, at least 17, or 18 of the indels of Table 4. In some embodiments, probes specific for the sequence-variable target region set comprise probes specific for at least a portion of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 of the genes of Table 5.

In some embodiments, the probes specific for the sequence-variable target region set comprise probes specific for target regions from at least 10, 20, 30, or 35 cancer-related genes, such as AKT1, ALK, BRAF, CCND1, CDK2A, CTNNB1, EGFR, ERBB2, ESR1, FGFR1, FGFR2, FGFR3, FOXL2, GATA3, GNA11, GNAQ, GNAS, HRAS, IDH1, IDH2, KIT, KRAS, MED12, MET, MYC, NFE2L2, NRAS, PDGFRA, PIK3CA, PPP2R1A, PTEN, RET, STK11, TP53, and U2AF1.

F. Sequencing

Sample nucleic acids, optionally flanked by adapters, with or without prior amplification are generally subjected to sequencing. Sequencing methods or commercially available formats that are optionally utilized include, for example, Sanger sequencing, high-throughput sequencing, pyrosequencing, sequencing-by-synthesis, single-molecule sequencing, nanopore-based sequencing, semiconductor sequencing, sequencing-by-ligation, sequencing-by-hybridization, RNA-Seq (Illumina), Digital Gene Expression (Helicos), next-generation sequencing (NGS), Single Molecule Sequencing by Synthesis (SMSS) (Helicos), massively-parallel sequencing, Clonal Single Molecule Array (Solexa), shotgun sequencing, Ion Torrent, Oxford Nanopore, Roche Genia, Maxim-Gilbert sequencing, primer walking, sequencing using PacBio, SOLiD, Ion Torrent, or Nanopore platforms. Sequencing reactions can be performed in a variety of sample processing units, which may include multiple lanes, multiple channels, multiple wells, or other means of processing multiple sample sets substantially simultaneously. Sample processing units can also include multiple sample chambers to enable the processing of multiple runs simultaneously.

In some embodiments, a sequencing step is performed on a library comprising captured set of target regions, which may comprise any of the target region sets described herein. In some embodiments, a sequencing step is performed on a library comprising a partition that has not undergone capture/enrichment (e.g., a whole genome sample). For example, target regions may be captured from the first partition and the second sample and then sequenced; or target regions may be captured from the first partition and combined with the second partition after processing such as contacting and tagging steps; or target regions may be captured from the second partition and combined with the first partition after processing such as contacting and tagging steps; or both the first and second partitions may be processed and combined without undergoing capture/enrichment.

The sequencing reactions can be performed on one or more nucleic acid fragment types or regions containing markers of cancer or of other diseases. The sequencing reactions can also be performed on any nucleic acid fragment present in the sample. The sequence reactions may be performed on at least about 5%, 10%, 15%, 20%, 25%, 30%, 40%, 50%, 60%, 70%, 80%, 90%, 95%, 99%, 99.9%, or 100% of the genome. In other cases, sequence reactions may be performed on less than about 5%, 10%, 15%, 20%, 25%, 30%, 40%, 50%, 60%, 70%, 80%, 90%, 95%, 99%, 99.9%, or 100% of the genome. Sequence coverage can performed on at least 5, 10, 20, 70, 100% of the genome, at least 200 or 500 different genes, or up to 5000, 2500, 1000, 500 or 100 different genes.

Simultaneous sequencing reactions may be performed using multiplex sequencing techniques. In some embodiments, cell-free polynucleotides are sequenced with at least about 1000, 2000, 3000, 4000, 5000, 6000, 7000, 8000, 9000, 10000, 50000, or 100,000 sequencing reactions. In other embodiments, cell-free polynucleotides are sequenced with less than about 1000, 2000, 3000, 4000, 5000, 6000, 7000, 8000, 9000, 10000, 50000, or 100,000 sequencing reactions. Sequencing reactions are typically performed sequentially or simultaneously. Subsequent data analysis is generally performed on all or part of the sequencing reactions. In some embodiments, data analysis is performed on at least about 1000, 2000, 3000, 4000, 5000, 6000, 7000, 8000, 9000, 10000, 50000, or 100,000 sequencing reactions. In other embodiments, data analysis may be performed on less than about 1000, 2000, 3000, 4000, 5000, 6000, 7000, 8000, 9000, 10000, 50000, or 100,000 sequencing reactions. An example of a read depth is from about 1000 to about 50000 reads per locus (e.g., base position). Another example of a read depth has at least 50000 reads per locus (e.g., base position).

1. Differential Depth of Sequencing

In some embodiments, nucleic acids corresponding to the sequence-variable target region set are sequenced to a greater depth of sequencing than nucleic acids corresponding to the epigenetic target region set. For example, the depth of sequencing for nucleic acids corresponding to the sequence variant target region set may be at least 1.25-, 1.5-, 1.75-, 2-, 2.25-, 2.5-, 2.75-, 3-, 3.5-, 4-, 4.5-, 5-, 6-, 7-, 8-, 9-, 10-, 11-, 12-, 13-, 14-, or 15-fold greater, or 1.25- to 1.5-, 1.5- to 1.75-, 1.75- to 2-, 2- to 2.25-, 2.25- to 2.5-, 2.5- to 2.75-, 2.75- to 3-, 3- to 3.5-, 3.5- to 4-, 4- to 4.5-, 4.5- to 5-, 5- to 5.5-, 5.5- to 6-, 6- to 7-, 7- to 8-, 8- to 9-, 9- to 10-, 10- to 11-, 11- to 12-, 13- to 14-, 14- to 15-fold, or 15- to 100-fold greater, than the depth of sequencing for nucleic acids corresponding to the epigenetic target region set. In some embodiments, said depth of sequencing is at least 2-fold greater. In some embodiments, said depth of sequencing is at least 5-fold greater. In some embodiments, said depth of sequencing is at least 10-fold greater. In some embodiments, said depth of sequencing is 4- to 10-fold greater. In some embodiments, said depth of sequencing is 4- to 100-fold greater. Each of these embodiments refer to the extent to which nucleic acids corresponding to the sequence-variable target region set are sequenced to a greater depth of sequencing than nucleic acids corresponding to the epigenetic target region set.

In some embodiments, the captured DNA corresponding to the sequence-variable target region set and the captured DNA corresponding to the epigenetic target region set are sequenced concurrently, e.g., in the same sequencing cell (such as the flow cell of an Illumina sequencer) and/or in the same composition, which may be a pooled composition resulting from recombining separately captured sets or a composition obtained by capturing the cfDNA corresponding to the sequence-variable target region set and the captured DNA corresponding to the epigenetic target region set in the same vessel.

G. Additional Features of Certain Methods a. Subjecting a Sample or Partition to a Procedure that Affects a First Nucleobase in the DNA Differently from a Second Nucleobase in the DNA Methods disclosed herein may comprise a step of subjecting a sample or first partition to a procedure that affects a first nucleobase in the DNA differently from a second nucleobase in the DNA of the first partition, wherein the first nucleobase is a modified or unmodified nucleobase, the second nucleobase is a modified or unmodified nucleobase different from the first nucleobase, and the first nucleobase and the second nucleobase have the same base pairing specificity (e.g., while the second partition is contacted with a MSRE according to any of the embodiments described elsewhere herein). In some embodiments, if the first nucleobase is a modified or unmodified adenine, then the second nucleobase is a modified or unmodified adenine; if the first nucleobase is a modified or unmodified cytosine, then the second nucleobase is a modified or unmodified cytosine; if the first nucleobase is a modified or unmodified guanine, then the second nucleobase is a modified or unmodified guanine; and if the first nucleobase is a modified or unmodified thymine, then the second nucleobase is a modified or unmodified thymine (where modified and unmodified uracil are encompassed within modified thymine for the purpose of this step). Such a procedure can be used to identify nucleotides in the partition that have or lack certain modifications, such as methylation.

In some embodiments, the first nucleobase is a modified or unmodified cytosine, then the second nucleobase is a modified or unmodified cytosine. For example, first nucleobase may comprise unmodified cytosine (C) and the second nucleobase may comprise one or more of 5-methylcytosine (mC) and 5-hydroxymethylcytosine (hmC). Alternatively, the second nucleobase may comprise C and the first nucleobase may comprise one or more of mC and hmC. Other combinations are also possible, as indicated, e.g., in the Summary above and the following discussion, such as where one of the first and second nucleobases comprises mC and the other comprises hmC.

In some embodiments, the procedure that affects a first nucleobase in the DNA differently from a second nucleobase in the DNA of the first partition comprises bisulfite conversion. Treatment with bisulfite converts unmodified cytosine and certain modified cytosine nucleotides (e.g. 5-formyl cytosine (fC) or 5-carboxylcytosine (caC)) to uracil whereas other modified cytosines (e.g., 5-methylcytosine, 5-hydroxylmethylcystosine) are not converted. Thus, where bisulfite conversion is used, the first nucleobase comprises one or more of unmodified cytosine, 5-formyl cytosine, 5-carboxylcytosine, or other cytosine forms affected by bisulfite, and the second nucleobase may comprise one or more of mC and hmC, such as mC and optionally hmC. Sequencing of bisulfite-treated DNA identifies positions that are read as cytosine as being mC or hmC positions. Meanwhile, positions that are read as T are identified as being T or a bisulfite-susceptible form of C, such as unmodified cytosine, 5-formyl cytosine, or 5-carboxylcytosine. Performing bisulfite conversion on a first partition as described herein thus facilitates identifying positions containing mC or hmC using the sequence reads obtained from the first partition. For an exemplary description of bisulfite conversion, see, e.g., Moss et al., Nat Commun. 2018; 9: 5068.

In some embodiments, the procedure that affects a first nucleobase in the DNA differently from a second nucleobase in the DNA of the first partition comprises oxidative bisulfite (Ox-BS) conversion. This procedure first converts hmC to fC, which is bisulfite susceptible, followed by bisulfite conversion. Thus, when oxidative bisulfite conversion is used, the first nucleobase comprises one or more of unmodified cytosine, fC, caC, hmC, or other cytosine forms affected by bisulfite, and the second nucleobase comprises mC. Sequencing of Ox-BS converted DNA identifies positions that are read as cytosine as being mC positions. Meanwhile, positions that are read as T are identified as being T, hmC, or a bisulfite-susceptible form of C, such as unmodified cytosine, fC, or hmC. Performing Ox-BS conversion on a first partition as described herein thus facilitates identifying positions containing mC using the sequence reads obtained from the first partition. For an exemplary description of oxidative bisulfite conversion, see, e.g., Booth et al., Science 2012; 336: 934-937.

In some embodiments, the procedure that affects a first nucleobase in the DNA differently from a second nucleobase in the DNA of the first partition comprises Tet-assisted bisulfite (TAB) conversion. In TAB conversion, hmC is protected from conversion and mC is oxidized in advance of bisulfite treatment, so that positions originally occupied by mC are converted to U while positions originally occupied by hmC remain as a protected form of cytosine. For example, as described in Yu et al., Cell 2012; 149: 1368-80, β-glucosyl transferase can be used to protect hmC (forming 5-glucosylhydroxymethylcytosine (ghmC)), then a TET protein such as mTet1 can be used to convert mC to caC, and then bisulfite treatment can be used to convert C and caC to U while ghmC remains unaffected. Thus, when TAB conversion is used, the first nucleobase comprises one or more of unmodified cytosine, fC, caC, mC, or other cytosine forms affected by bisulfite, and the second nucleobase comprises hmC. Sequencing of TAB-converted DNA identifies positions that are read as cytosine as being hmC positions. Meanwhile, positions that are read as T are identified as being T, mC, or a bisulfite-susceptible form of C, such as unmodified cytosine, fC, or caC. Performing TAB conversion on a first partition as described herein thus facilitates identifying positions containing hmC using the sequence reads obtained from the first partition.

In some embodiments, the procedure that affects a first nucleobase in the DNA differently from a second nucleobase in the DNA of the first partition comprises Tet-assisted conversion with a substituted borane reducing agent, optionally wherein the substituted borane reducing agent is 2-picoline borane, borane pyridine, tert-butylamine borane, or ammonia borane. In Tet-assisted pic-borane conversion with a substituted borane reducing agent conversion, a TET protein is used to convert mC and hmC to caC, without affecting unmodified C. caC, and fC if present, are then converted to dihydrouracil (DHU) by treatment with 2-picoline borane (pic-borane) or another substituted borane reducing agent such as borane pyridine, tert-butylamine borane, or ammonia borane, also without affecting unmodified C. See, e.g., Liu et al., Nature Biotechnology 2019; 37:424-429 (e.g., at Supplementary FIG. 1 and Supplementary Note 7). DHU is read as a T in sequencing. Thus, when this type of conversion is used, the first nucleobase comprises one or more of mC, fC, caC, or hmC, and the second nucleobase comprises unmodified cytosine. Sequencing of the converted DNA identifies positions that are read as cytosine as being unmodified C positions. Meanwhile, positions that are read as T are identified as being T, mC, fC, caC, or hmC. Performing TAP conversion on a first partition as described herein thus facilitates identifying positions containing unmodified C using the sequence reads obtained from the first partition. This procedure encompasses Tet-assisted pyridine borane sequencing (TAPS), described in further detail in Liu et al. 2019, supra.

Alternatively, protection of hmC (e.g., using βGT) can be combined with Tet-assisted conversion with a substituted borane reducing agent. hmC can be protected as noted above through glucosylation using βGT, forming ghmC. Treatment with a TET protein such as mTet1 then converts mC to caC but does not convert C or ghmC. caC is then converted to DHU by treatment with pic-borane or another substituted borane reducing agent such as borane pyridine, tert-butylamine borane, or ammonia borane, also without affecting unmodified C or ghmC. Thus, when Tet-assisted conversion with a substituted borane reducing agent is used, the first nucleobase comprises mC, and the second nucleobase comprises one or more of unmodified cytosine or hmC, such as unmodified cytosine and optionally hmC, fC, and/or caC. Sequencing of the converted DNA identifies positions that are read as cytosine as being either hmC or unmodified C positions. Meanwhile, positions that are read as T are identified as being T, fC, caC, or mC. Performing TAPSβ conversion on a first partition as described herein thus facilitates distinguishing positions containing unmodified C or hmC on the one hand from positions containing mC using the sequence reads obtained from the first partition. For an exemplary description of this type of conversion, see, e.g., Liu et al., Nature Biotechnology 2019; 37:424-429.

In some embodiments, the procedure that affects a first nucleobase in the DNA differently from a second nucleobase in the DNA of the first partition comprises chemical-assisted conversion with a substituted borane reducing agent, optionally wherein the substituted borane reducing agent is 2-picoline borane, borane pyridine, tert-butylamine borane, or ammonia borane. In chemical-assisted conversion with a substituted borane reducing agent, an oxidizing agent such as potassium perruthenate (KRuO4) (also suitable for use in ox-BS conversion) is used to specifically oxidize hmC to fC. Treatment with pic-borane or another substituted borane reducing agent such as borane pyridine, tert-butylamine borane, or ammonia borane converts fC and caC to DHU but does not affect mC or unmodified C. Thus, when this type of conversion is used, the first nucleobase comprises one or more of hmC, fC, and caC, and the second nucleobase comprises one or more of unmodified cytosine or mC, such as unmodified cytosine and optionally mC. Sequencing of the converted DNA identifies positions that are read as cytosine as being either mC or unmodified C positions. Meanwhile, positions that are read as T are identified as being T, fC, caC, or hmC. Performing this type of conversion on a first partition as described herein thus facilitates distinguishing positions containing unmodified C or mC on the one hand from positions containing hmC using the sequence reads obtained from the first partition. For an exemplary description of this type of conversion, see, e.g., Liu et al., Nature Biotechnology 2019; 37:424-429.

In some embodiments, the procedure that affects a first nucleobase in the DNA differently from a second nucleobase in the DNA of the first partition comprises APOBEC-coupled epigenetic (ACE) conversion. In ACE conversion, an AID/APOBEC family DNA deaminase enzyme such as APOBEC3A (A3A) is used to deaminate unmodified cytosine and mC without deaminating hmC, fC, or caC. Thus, when ACE conversion is used, the first nucleobase comprises unmodified C and/or mC (e.g., unmodified C and optionally mC), and the second nucleobase comprises hmC. Sequencing of ACE-converted DNA identifies positions that are read as cytosine as being hmC, fC, or caC positions. Meanwhile, positions that are read as T are identified as being T, unmodified C, or mC. Performing ACE conversion on a first partition as described herein thus facilitates distinguishing positions containing hmC from positions containing mC or unmodified C using the sequence reads obtained from the first partition. For an exemplary description of ACE conversion, see, e.g., Schutsky et al., Nature Biotechnology 2018; 36: 1083-1090.

In some embodiments, procedure that affects a first nucleobase in the DNA differently from a second nucleobase in the DNA of the first partition comprises enzymatic conversion of the first nucleobase, e.g., as in EM-Seq. See, e.g., Vaisvila R, et al. (2019) EM-seq: Detection of DNA methylation at single base resolution from picograms of DNA. bioRxiv; DOI: 10.1101/2019.12.20.884692, available at www.biorxiv.org/content/10.1101/2019.12.20.884692v1.
For example, TET2 and T4-βGT can be used to convert 5mC and 5hmC into substrates that cannot be deaminated by a deaminase (e.g., APOBEC3A), and then a deaminase (e.g., APOBEC3A) can be used to deaminate unmodified cytosines converting them to uracils.

In some embodiments, the procedure that affects a first nucleobase in the DNA differently from a second nucleobase in the DNA of the first partition comprises separating DNA originally comprising the first nucleobase from DNA not originally comprising the first nucleobase. In some such embodiments, the first nucleobase is hmC. DNA originally comprising the first nucleobase may be separated from other DNA using a labeling procedure comprising biotinylating positions that originally comprised the first nucleobase. In some embodiments, the first nucleobase is first derivatized with an azide-containing moiety, such as a glucosyl-azide containing moiety. The azide-containing moiety then may serve as a reagent for attaching biotin, e.g., through Huisgen cycloaddition chemistry. Then, the DNA originally comprising the first nucleobase, now biotinylated, can be separated from DNA not originally comprising the first nucleobase using a biotin-binding agent, such as avidin, neutravidin (deglycosylated avidin with an isoelectric point of about 6.3), or streptavidin. An example of a procedure for separating DNA originally comprising the first nucleobase from DNA not originally comprising the first nucleobase is hmC-seal, which labels hmC to form β-6-azide-glucosyl-5-hydroxymethylcytosine and then attaches a biotin moiety through Huisgen cycloaddition, followed by separation of the biotinylated DNA from other DNA using a biotin-binding agent. For an exemplary description of hmC-seal, see, e.g., Han et al., Mol. Cell 2016; 63: 711-719. This approach is useful for identifying fragments that include one or more hmC nucleobases.

In some embodiments, following such a separation, the method further comprises differentially tagging each of the DNA originally comprising the first nucleobase, the DNA not originally comprising the first nucleobase, and the DNA of the second partition. The method may further comprise pooling the DNA originally comprising the first nucleobase, the DNA not originally comprising the first nucleobase, and the DNA of the second partition following differential tagging. The DNA originally comprising the first nucleobase, the DNA not originally comprising the first nucleobase, and the DNA of the second partition may then be sequenced in the same sequencing cell while retaining the ability to resolve whether a given read came from a molecule of DNA originally comprising the first nucleobase, DNA not originally comprising the first nucleobase, or DNA of the second partition using the differential tags.

In some embodiments, the first nucleobase is a modified or unmodified adenine, and the second nucleobase is a modified or unmodified adenine. In some embodiments, the modified adenine is N6-methyladenine (mA). In some embodiments, the modified adenine is one or more of N6-methyladenine (mA), N6-hydroxymethyladenine (hmA), or N6-formyladenine (fA).

Techniques comprising methylated DNA immunoprecipitation (MeDIP) can be used to separate DNA containing modified bases such as mA from other DNA. See, e.g., Kumar et al., Frontiers Genet. 2018; 9: 640; Greer et al., Cell 2015; 161: 868-878. An antibody specific for mA is described in Sun et al., Bioessays 2015; 37:1155-62. Antibodies for various modified nucleobases, such as forms of thymine/uracil including halogenated forms such as 5-bromouracil, are commercially available. Various modified bases can also be detected based on alterations in their base-pairing specificity. For example, hypoxanthine is a modified form of adenine that can result from deamination and is read in sequencing as a G. See, e.g., U.S. Pat. No. 8,486,630; Brown, Genomes, 2nd Ed., John Wiley & Sons, Inc., New York, N.Y., 2002, chapter 14, "Mutation, Repair, and Recombination."

b. Subjects

In some embodiments, the nucleic acid molecules, such as DNA (e.g., cfDNA) are obtained from a subject having a cancer. In some embodiments, DNA (e.g., cfDNA) is obtained from a subject suspected of having a cancer. In some embodiments, DNA (e.g., cfDNA) is obtained from a subject having a tumor. In some embodiments, DNA (e.g., cfDNA) is obtained from a subject suspected of having a tumor. In some embodiments, DNA (e.g., cfDNA) is obtained from a subject having neoplasia. In some embodiments, DNA (e.g., cfDNA) is obtained from a subject suspected of having neoplasia. In some embodiments, DNA (e.g., cfDNA) is obtained from a subject in remission from a tumor, cancer, or neoplasia (e.g., following chemotherapy, surgical resection, radiation, or a combination thereof). In any of the foregoing embodiments, the cancer, tumor, or neoplasia or suspected cancer, tumor, or neoplasia may be of the lung, colon, rectum, kidney, breast, prostate, or liver. In some embodiments, the cancer, tumor, or neoplasia or suspected cancer, tumor, or neoplasia is of the lung. In some embodiments, the cancer, tumor, or neoplasia or suspected cancer, tumor, or neoplasia is of the colon or rectum. In some embodiments, the cancer, tumor, or neoplasia or suspected cancer, tumor, or neoplasia is of the breast. In some embodiments, the cancer, tumor, or neoplasia or suspected cancer, tumor, or neoplasia is of the prostate. In any of the foregoing embodiments, the subject may be a human subject.

c. Quantification

In some embodiments, epigenetic target regions captured from one or more of the first partition, the treated first partition, or the treated second partition are quantified. For example, hypomethylation variable target regions may be quantified in the treated second partition, and/or hypermethylation variable target regions may be quantified in the first partition or treated first partition. Quantification may be by any appropriate technique, e.g., quantitative amplification such as quantitative PCR. In some embodiments, quantification is based on sequencing data (e.g., number of sequencing reads or number of unique molecules sequenced).

Quantification of epigenetic target regions as discussed above can be used for determining a presence, absence, or likelihood of cancer in a subject. For example, a determination of the presence or absence of cancer can be based, at least in part, on whether the amount of hypermethylation variable target regions in the first partition or treated first partition and/or the amount of hypomethylation variable target regions in the treated second partition exceeds a predetermined threshold. In some embodiments, such an amount can be used together with other data collected from the sample, e.g., the presence of mutations and/or other epigenetic features described elsewhere herein such as perturbations of transcription start sites and/or CTCF binding sites.

d. Pooling of DNA from First and Second Partitions or Portions Thereof

In some embodiments, the methods comprise preparing a pool comprising at least a portion of the DNA of the second partition (e.g., the hypomethylated partition) and at least a portion of the DNA of the first partition (e.g., the hypermethylated partition). Target regions, e.g., including epigenetic target regions and/or sequence-variable target regions, may be captured from the pool. The steps of capturing a target region set from at least a portion of a partition described elsewhere herein encompass capture steps performed on a pool comprising DNA from the first and second partitions. A step of amplifying DNA in the pool may be performed before capturing target regions from the pool. The capturing step may have any of the features described elsewhere herein.

The epigenetic target regions may show differences in methylation levels and/or fragmentation patterns depending on whether they originated from a tumor or from healthy cells, or what type of tissue they originated from, as discussed elsewhere herein. The sequence-variable target regions may show differences in sequence depending on whether they originated from a tumor or from healthy cells.

Analysis of epigenetic target regions from the hypomethylated partition may be less informative in some applications than analysis of sequence-variable target-regions from the hypermethylated and hypomethylated partitions and epigenetic target regions from the hypermethylated partition. As such, in methods where sequence-variable target-regions and epigenetic target regions are being captured, the latter may be captured to a lesser extent than one or more of the sequence-variable target-regions from the hypermethylated and hypomethylated partitions and epigenetic target regions from the hypermethylated partition. For example, sequence-variable target regions can be captured from the portion of the hypomethylated partition not pooled with the hypermethylated partition, and the pool can be prepared with some (e.g., a majority, substantially all, or all) of the DNA from the hypermethylated partition and none or some (e.g., a minority) of the DNA from the hypomethylated partition. Such approaches can reduce or eliminate sequencing of epigenetic target regions from the hypomethylated partition, thereby reducing the amount of sequencing data that suffices for further analysis.

In some embodiments, including a minority of the DNA of the hypomethylated partition in the pool facilitates quantification of one or more epigenetic features (e.g., methylation or other epigenetic feature(s) discussed in detail elsewhere herein), e.g., on a relative basis.

In some embodiments, the pool comprises a minority of the DNA of the hypomethylated partition, e.g., less than about 50% of the DNA of the hypomethylated partition, such as less than or equal to about 45%, 40%, 35%, 30%, 25%, 20%, 15%, 10%, or 5% of the DNA of the hypomethylated partition. In some embodiments, the pool comprises about 5%-25% of the DNA of the hypomethylated partition. In some embodiments, the pool comprises about 10%-20% of the DNA of the hypomethylated partition. In some embodiments, the pool comprises about 10% of the DNA of the hypomethylated partition. In some embodiments, the pool comprises about 15% of the DNA of the hypomethylated partition. In some embodiments, the pool comprises about 20% of the DNA of the hypomethylated partition.

In some embodiments, the pool comprises a portion of the hypermethylated partition, which may be at least about 50% of the DNA of the hypermethylated partition. For example, the pool may comprise at least about 55%, 60%, 65%, 70%, 75%, 80%, 85%, 90%, or 95% of the DNA of the hypermethylated partition. In some embodiments, the pool comprises 50-55%, 55-60%, 60-65%, 65-70%, 70-75%, 75-80%, 80-85%, 85-90%, 90-95%, or 95-100% of the DNA of the hypermethylated partition. In some embodiments, the second pool comprises all or substantially all of the hypermethylated partition.

In some embodiments, the methods comprise preparing a first pool comprising at least a portion of the DNA of the hypomethylated partition. In some embodiments, the methods comprise preparing a second pool comprising at least a portion of the DNA of the hypermethylated partition. In some embodiments, the first pool further comprises a portion of the DNA of the hypermethylated partition. In some embodiments, the second pool further comprises a portion of the DNA of the hypomethylated partition. In some embodiments, the first pool comprises a majority of the DNA of the hypomethylated partition, and optionally and a minority of the DNA of the hypermethylated partition. In some embodiments, the second pool comprises a majority of the DNA of the hypermethylated partition and a minority of the DNA of the hypomethylated partition. In some embodiments involving an intermediately methylated partition, the second pool comprises at least a portion of the DNA of the intermediately methylated partition, e.g., a majority of the DNA of the intermediately methylated partition. In some embodiments, the first pool comprises a majority of the DNA of the hypomethylated partition, and the second pool comprises a majority of the DNA of the hypermethylated partition and a majority of the DNA of the intermediately methylated partition.

In some embodiments, the methods comprise capturing at least a first set of target regions from the first pool, e.g., wherein the first pool is as set forth in any of the embodiments above. In some embodiments, the first set comprises sequence-variable target regions. In some embodiments, the first set comprises hypomethylation variable target regions and/or fragmentation variable target regions. In some embodiments, the first set comprises sequence-variable target regions and fragmentation variable target regions. In some embodiments, the first set comprises sequence-variable target regions, hypomethylation variable target regions and fragmentation variable target regions. A step of amplifying DNA in the first pool may be performed before this capture step. In some embodiments, capturing the first set of target regions from the first pool comprises contacting the DNA of the first pool with a first set of target-specific probes.

In some embodiments, the first set of target-specific probes comprises target-binding probes specific for the sequence-variable target regions. In some embodiments, the first set of target-specific probes comprises target-binding probes specific for the sequence-variable target regions, hypomethylation variable target regions and/or fragmentation variable target regions.

In some embodiments, the methods comprise capturing a second set of target regions or plurality of sets of target regions from the second pool, e.g., wherein the first pool is as set forth in any of the embodiments above. In some embodiments, the second plurality comprises epigenetic target regions, such as hypermethylation variable target regions and/or fragmentation variable target regions. In some embodiments, the second plurality comprises sequence-variable target regions and epigenetic target regions, such as hypermethylation variable target regions and/or fragmentation variable target regions. A step of amplifying DNA in the second pool may be performed before this capture step. In some embodiments, capturing the second plurality of sets of target regions from the second pool comprises contacting the DNA of the first pool with a second set of target-specific probes, wherein the second set of target-specific probes comprises target-binding probes specific for the sequence-variable target regions and target-binding probes specific for the epigenetic target regions. In some embodiments, the first set of target regions and the second set of target regions are not identical. For example, the first set of target regions may comprise one or more target regions not present in the second set of target regions. Alternatively or in addition, the second set of target regions may comprise one or more target regions not present in the first set of target regions. In some embodiments, at least one hypermethylation variable target region is captured from the second pool but not from the first pool. In some embodiments, a plurality of hypermethylation variable target regions are captured from the second pool but not from the first pool. In some embodiments, the first set of target regions comprises sequence-variable target regions and/or the second set of target regions comprises epigenetic target regions. In some embodiments, the first set of target regions comprises sequence-variable target regions, and fragmentation variable target regions; and the second set of target regions comprises epigenetic target regions, such as hypermethylation variable target regions and fragmentation variable target regions. In some embodiments, the first set of target regions comprises sequence-variable target regions, fragmentation variable target regions, and comprises hypomethylation variable target regions; and the second set of target regions comprises epigenetic target regions, such as hypermethylation variable target regions and fragmentation variable target regions.

In some embodiments, the first pool comprises a majority of the DNA of the hypomethylated partition and a portion of the DNA of the hypermethylated partition (e.g., about half), and the second pool comprises a portion of the DNA of the hypermethylated partition (e.g., about half). In some such embodiments, the first set of target regions comprises sequence-variable target regions and/or the second set of target regions comprises epigenetic target regions. The sequence-variable target regions and/or the epigenetic target regions may be as set forth in any of the embodiments described elsewhere herein.

f. Capture Moieties, Bait Sets

As discussed above, nucleic acids in a sample can be subject to a capture step, in which molecules having target sequences are captured for subsequent analysis. Target capture can involve use of a bait set comprising oligonucleotide baits, such as target specific probes, labeled with a capture moiety, such as biotin or the other examples noted below. The probes can have sequences selected to tile across a panel of regions, such as genes. In some embodiments, a bait set can have higher and lower capture yields for sets of target regions such as those of the sequence-variable target region set and the epigenetic target region set, respectively, as discussed elsewhere herein. Such bait sets are combined with a sample under conditions that allow hybridization of the target molecules with the baits. Then, captured molecules are isolated using the capture moiety. For example, a biotin capture moiety by bead-based streptavidin. Such methods are further described in, for example, U.S. Pat. No. 9,850,523, issuing Dec. 26, 2017, which is incorporated herein by reference.

Capture moieties include, without limitation, biotin, avidin, streptavidin, a nucleic acid comprising a particular nucleotide sequence, a hapten recognized by an antibody, and magnetically attractable particles. The extraction moiety can be a member of a binding pair, such as biotin/streptavidin or hapten/antibody. In some embodiments, a capture moiety that is attached to an analyte is captured by its binding pair which is attached to an isolatable moiety, such as a magnetically attractable particle or a large particle that can be sedimented through centrifugation. The capture moiety can be any type of molecule that allows affinity separation of nucleic acids bearing the capture moiety from nucleic acids lacking the capture moiety. Exemplary capture moieties are biotin which allows affinity separation by binding to streptavidin linked or linkable to a solid phase or an oligonucleotide, which allows affinity separation through binding to a complementary oligonucleotide linked or linkable to a solid phase.

H. Analysis

In some embodiments, a method described herein comprises identifying the presence of DNA produced by a tumor (or neoplastic cells, or cancer cells).

In some embodiments, the methods herein comprise analyzing nucleic acid molecules in which at least some of the nucleic acids include one or more modified cytosine residues, such as 5-methylcytosine and any of the other modifications described previously. In some such methods, after partitioning, the partitions of nucleic acids are contacted with adapters including one or more cytosine residues modified at the 5C position, such as 5-methylcytosine. In some embodiments, all cytosine residues in such adapters are also modified, or all such cytosines in a primer binding region of the adapters are modified. Adapters attach to both ends of nucleic acid molecules in the population. In some embodiments, the adapters include different tags of sufficient numbers that the number of combinations of tags results in a low probability e.g., 95, 99 or 99.9% of two nucleic acids with the same start and stop points receiving the same combination of tags. The primer binding sites in such adapters can be the same or different, but are preferably the same. After attachment of adapters, the nucleic acids are amplified from primers binding to the primer binding sites of the adapters. The amplified nucleic acids are split into first and second aliquots. The first aliquot is assayed for sequence data with or without further processing. The sequence data on molecules in the first aliquot is thus determined irrespective of the initial methylation state of the nucleic acid molecules. The nucleic acid molecules in the second aliquot are subjected to a procedure that affects a first nucleobase in the DNA differently from a second nucleobase in the DNA, wherein the first nucleobase comprises a cytosine modified at the 5 position, and the second nucleobase comprises unmodified cytosine. This procedure may be bisulfite treatment or another procedure that converts unmodified cytosines to uracils. The nucleic acids subjected to the procedure are then amplified with primers to the original primer binding sites of the adapters linked to nucleic acid. Only the nucleic acid molecules originally linked to adapters (as distinct from amplification products thereof) are now amplifiable because these nucleic acids retain cytosines in the primer binding sites of the adapters, whereas amplification products have lost the methylation of these cytosine residues, which have undergone conversion to uracils in the bisulfite treatment. Thus, only original nucleic acid molecules in the populations, at least some of which are methylated, undergo amplification. After amplification, these nucleic acids are subject to sequence analysis. Comparison of sequences determined from the first and second aliquots can indicate among other things, which cytosines in the nucleic acid population were subject to methylation.

Such an analysis can be performed using the following exemplary procedure. After partitioning, methylated DNA is linked to Y-shaped adapters at both ends including primer binding sites and tags. The cytosines in the adapters are modified at the 5 position (e.g., 5-methylated). The modification of the adapters serves to protect the primer binding sites in a subsequent conversion step (e.g., bisulfite treatment, TAP conversion, or any other conversion that does not affect the modified cytosine but affects unmodified cytosine). After attachment of adapters, the DNA molecules are amplified. The amplification product is split into two aliquots for sequencing with and without conversion. The aliquot not subjected to conversion can be subjected to sequence analysis with or without further processing. The other aliquot is subjected to a procedure that affects a first nucleobase in the DNA differently from a second nucleobase in the DNA, wherein the first nucleobase comprises a cytosine modified at the 5 position, and the second nucleobase comprises unmodified cytosine. This procedure may be bisulfite treatment or another procedure that converts unmodified cytosines to uracils. Only primer binding sites protected by modification of cytosines can support amplification when contacted with primers specific for original primer binding sites. Thus, only original molecules and not copies from the first amplification are subjected to further amplification. The further amplified molecules are then subjected to sequence analysis. Sequences can then be compared from the two aliquots. As in the separation scheme discussed above, nucleic acid tags in adapters are not used to distinguish between methylated and unmethylated DNA but to distinguish nucleic acid molecules within the same partition.

Sequencing may generate a plurality of sequence reads or reads. Sequence reads or reads may include sequences of nucleotide data less than about 150 bases in length, or less than about 90 bases in length. In some embodiments, reads are between about 80 bases and about 90 bases, e.g., about 85 bases in length. In some embodiments, methods of the present disclosure are applied to very short reads, e.g., less than about 50 bases or about 30 bases in length. Sequence read data can include the sequence data as well as meta information. Sequence read data can be stored in any suitable file format including, for example, VCF files, FASTA files, or FASTQ files.

FASTA may refer to a computer program for searching sequence databases, and the name FASTA may also refer to a standard file format. FASTA is described by, for example, Pearson & Lipman, 1988, Improved tools for biological sequence comparison, PNAS 85:2444-2448, which is hereby incorporated by reference in its entirety. A sequence in FASTA format begins with a single-line description, followed by lines of sequence data. The description line is distinguished from the sequence data by a greater-than (">") symbol in the first column. The word following the ">" symbol is the identifier of the sequence, and the rest of the line is the description (both are optional). There may be no space between the ">" and the first letter of the identifier. It is recommended that all lines of text be shorter than 80 characters. The sequence ends if another line starting with a ">" appears; this indicates the start of another sequence.

The FASTQ format is a text-based format for storing both a biological sequence (usually nucleotide sequence) and its corresponding quality scores. It is similar to the FASTA format but with quality scores following the sequence data. Both the sequence letter and quality score are encoded with a single ASCII character for brevity. The FASTQ format is a de facto standard for storing the output of high throughput sequencing instruments such as the Illumina Genome Analyzer, as described by, for example, Cock et al. ("The Sanger FASTQ file format for sequences with quality scores, and the Solexa/Illumina FASTQ variants," *Nucleic Acids Res* 38(6):1767-1771, 2009), which is hereby incorporated by reference in its entirety.

For FASTA and FASTQ files, meta information includes the description line and not the lines of sequence data. In some embodiments, for FASTQ files, the meta information includes the quality scores. For FASTA and FASTQ files, the sequence data begins after the description line and is present typically using some subset of IUPAC ambiguity codes optionally with "-". In an embodiment, the sequence data may use the A, T, C, G, and N characters, optionally including "-" or U as-needed (e.g., to represent gaps or uracil).

In some embodiments, the at least one master sequence read file and the output file are stored as plain text files (e.g., using encoding such as ASCII; ISO/IEC 646; EBCDIC; UTF-8; or UTF-16). A computer system provided by the present disclosure may include a text editor program capable of opening the plain text files. A text editor program may refer to a computer program capable of presenting contents of a text file (such as a plain text file) on a computer screen, allowing a human to edit the text (e.g., using a monitor, keyboard, and mouse). Examples of text editors include, without limitation, Microsoft Word, emacs, pico, vi, BBEdit, and TextWrangler. The text editor program may be capable of displaying the plain text files on a computer screen, showing the meta information and the sequence reads in a human-readable format (e.g., not binary encoded but instead using alphanumeric characters as they may be used in print or human writing).

While methods have been discussed with reference to FASTA or FASTQ files, methods and systems of the present disclosure may be used to compress any suitable sequence file format including, for example, files in the Variant Call Format (VCF) format. A typical VCF file may include a header section and a data section. The header contains an arbitrary number of meta-information lines, each starting with characters '##', and a TAB delimited field definition line starting with a single '#' character. The field definition line names eight mandatory columns and the body section contains lines of data populating the columns defined by the field definition line. The VCF format is described by, for example, Danecek et al. ("The variant call format and VCF tools," *Bioinformatics* 27(15):2156-2158, 2011), which is hereby incorporated by reference in its entirety. The header section may be treated as the meta information to write to the compressed files and the data section may be treated as the lines, each of which can be stored in a master file only if unique.

Some embodiments provide for the assembly of sequence reads. In assembly by alignment, for example, the sequence reads are aligned to each other or aligned to a reference sequence. By aligning each read, in turn to a reference genome, all of the reads are positioned in relationship to each other to create the assembly. In addition, aligning or mapping the sequence read to a reference sequence can also be used to identify variant sequences within the sequence read. Identifying variant sequences can be used in combination with the methods and systems described herein to further aid in the diagnosis or prognosis of a disease or condition, or for guiding treatment decisions.

In some embodiments, any or all of the steps are automated. Alternatively, methods of the present disclosure may be embodied wholly or partially in one or more dedicated programs, for example, each optionally written in a compiled language such as C++, then compiled and distributed as a binary. Methods of the present disclosure may be implemented wholly or in part as modules within, or by invoking functionality within, existing sequence analysis platforms. In some embodiments, methods of the present disclosure include a number of steps that are all invoked automatically responsive to a single starting queue (e.g., one or a combination of triggering events sourced from human activity, another computer program, or a machine). Thus, the present disclosure provides methods in which any or the steps or any combination of the steps can occur automatically responsive to a queue. "Automatically" generally means without intervening human input, influence, or interaction (e.g., responsive only to original or pre-queue human activity).

The methods of the present disclosure may also encompass various forms of output, which includes an accurate and sensitive interpretation of a subject's nucleic acid sample. The output of retrieval can be provided in the format of a computer file. In some embodiments, the output is a FASTA file, a FASTQ file, or a VCF file. The output may be processed to produce a text file, or an XML file containing sequence data such as a sequence of the nucleic acid aligned to a sequence of the reference genome. In other embodiments, processing yields output containing coordinates or a string describing one or more mutations in the subject nucleic acid relative to the reference genome. Alignment strings may include Simple UnGapped Alignment Report (SUGAR), Verbose Useful Labeled Gapped Alignment Report (VULGAR), and Compact Idiosyncratic Gapped Alignment Report (CIGAR) (as described by, for example, Ning et al., *Genome Research* 11(10):1725-9, 2001, which is hereby incorporated by reference in its entirety). These strings may be implemented, for example, in the Exonerate sequence alignment software from the European Bioinformatics Institute (Hinxton, UK).

In some embodiments, a sequence alignment is produced—such as, for example, a sequence alignment map (SAM) or binary alignment map (BAM) file—comprising a CIGAR string (the SAM format is described, e.g., by Li et al., "The Sequence Alignment/Map format and SAMtools," *Bioinformatics,* 25(16):2078-9, 2009, which is hereby incorporated by reference in its entirety). In some embodiments, CIGAR displays or includes gapped alignments one-per-line. CIGAR is a compressed pairwise alignment format reported as a CIGAR string. A CIGAR string may be useful for representing long (e.g., genomic) pairwise alignments. A CIGAR string may be used in SAM format to represent alignments of reads to a reference genome sequence.

A CIGAR string may follow an established motif. Each character is preceded by a number, giving the base counts of the event. Characters used can include M, I, D, N, and S (M=match; I=insertion; D=deletion; N=gap; S=substitution). The CIGAR string defines the sequence of matches and/or mismatches and deletions (or gaps). For example, the CIGAR string 2MD3M2D2M may indicate that the alignment contains 2 matches, 1 deletion (number 1 is omitted in order to save some space), 3 matches, 2 deletions, and 2 matches.

In some embodiments, a nucleic acid population is prepared for sequencing by enzymatically forming blunt-ends on double-stranded nucleic acids with single-stranded overhangs at one or both ends. In these embodiments, the population is typically treated with an enzyme having a 5'-3' DNA polymerase activity and a 3'-5' exonuclease activity in the presence of the nucleotides (e.g., A, C, G, and T or U). Examples of enzymes or catalytic fragments thereof that may be optionally used include Klenow large fragment and T4 polymerase. At 5' overhangs, the enzyme typically extends the recessed 3' end on the opposing strand until it is flush with the 5' end to produce a blunt end. At 3' overhangs, the enzyme generally digests from the 3' end up to and sometimes beyond the 5' end of the opposing strand. If this digestion proceeds beyond the 5' end of the opposing strand, the gap can be filled in by an enzyme having the same polymerase activity that is used for 5' overhangs. The formation of blunt ends on double-stranded nucleic acids facilitates, for example, the attachment of adapters and subsequent amplification.

In some embodiments, nucleic acid populations are subjected to additional processing, such as the conversion of single-stranded nucleic acids to double-stranded nucleic acids and/or conversion of RNA to DNA (e.g., complementary DNA or cDNA). These forms of nucleic acid are also optionally linked to adapters and amplified.

With or without prior amplification, nucleic acids subject to the process of forming blunt-ends described above, and optionally other nucleic acids in a sample, can be sequenced to produce sequenced nucleic acids. A sequenced nucleic acid can refer either to the sequence of a nucleic acid (e.g., sequence information) or a nucleic acid whose sequence has been determined. Sequencing can be performed so as to provide sequence data of individual nucleic acid molecules in a sample either directly or indirectly from a consensus sequence of amplification products of an individual nucleic acid molecule in the sample.

In some embodiments, double-stranded nucleic acids with single-stranded overhangs in a sample after blunt-end formation are linked at both ends to adapters including barcodes, and the sequencing determines nucleic acid sequences as well as in-line barcodes introduced by the adapters. The blunt-end DNA molecules are optionally ligated to a blunt end of an at least partially double-stranded adapter (e.g., a Y-shaped or bell-shaped adapter). Alternatively, blunt ends of sample nucleic acids and adapters can be tailed with complementary nucleotides to facilitate ligation (for e.g., sticky-end ligation).

The nucleic acid sample is typically contacted with a sufficient number of adapters that there is a low probability (e.g., less than about 1% or 0.1%) that any two copies of the same nucleic acid receive the same combination of adapter barcodes from the adapters linked at both ends. The use of adapters in this manner may permit identification of families of nucleic acid sequences with the same start and stop points on a reference nucleic acid and linked to the same combination of barcodes. Such a family may represent sequences of amplification products of a nucleic acid in the sample before amplification. The sequences of family members can be compiled to derive consensus nucleotide(s) or a complete consensus sequence for a nucleic acid molecule in the original sample, as modified by blunt-end formation and adapter attachment. In other words, the nucleotide occupying a specified position of a nucleic acid in the sample can be determined to be the consensus of nucleotides occupying that corresponding position in family member sequences. Families can include sequences of one or both strands of a double-stranded nucleic acid. If members of a family include sequences of both strands from a double-stranded nucleic acid, sequences of one strand may be converted to their complements for purposes of compiling sequences to derive consensus nucleotide(s) or sequences. Some families include only a single member sequence. In this case, this sequence can be taken as the sequence of a nucleic acid in the sample before amplification. Alternatively, families with only a single member sequence can be eliminated from subsequent analysis.

Nucleotide variations (e.g., SNVs or indels) in sequenced nucleic acids can be determined by comparing sequenced nucleic acids with a reference sequence. The reference sequence is often a known sequence, e.g., a known whole or partial genome sequence from a subject (e.g., a whole genome sequence of a human subject). The reference sequence can be an external reference sequence, for example, hG19 or hG38. The sequenced nucleic acids can represent sequences determined directly for a nucleic acid in a sample, or a consensus of sequences of amplification products of such a nucleic acid, as described above. A comparison can be performed at one or more designated positions on a reference sequence. A subset of sequenced nucleic acids can be identified including a position corresponding with a designated position of the reference sequence when the respective sequences are maximally aligned. Within such a subset it can be determined which, if any, sequenced nucleic acids include a nucleotide variation at the designated position, and optionally which if any, include a reference nucleotide (e.g., same as in the reference sequence). If the number of sequenced nucleic acids in the subset including a nucleotide variant exceeding a selected threshold, then a variant nucleotide can be called at the designated position. The threshold can be a number, such as at least 1, 2, 3, 4, 5, 6, 7, 8, 9, or 10 sequenced nucleic acids within the subset including the nucleotide variant, or it can be a ratio, such as at least about 0.5, 1, 2, 3, 4, 5, 10, 15, or 20, of sequenced nucleic acids within the subset that include the nucleotide variant, among other possibilities. The comparison can be repeated for any designated position of interest in the reference sequence. Sometimes a comparison can be performed for designated positions occupying at least about 20, 100, 200, or 300 contiguous positions on a reference sequence, e.g., about 20-500, or about 50-300 contiguous positions.

Additional details regarding nucleic acid sequencing, including the formats and applications described herein, are also provided in, for example, Levy et al., Annual Review of Genomics and Human Genetics, 17: 95-115 (2016), Liu et al., J. of Biomedicine and Biotechnology, Volume 2012, Article ID 251364:1-11 (2012), Voelkerding et al., Clinical Chem., 55: 641-658 (2009), MacLean et al., Nature Rev. Microbiol., 7: 287-296 (2009), Astier et al., J Am Chem Soc., 128(5):1705-10 (2006), U.S. Pat. Nos. 6,210,891, 6,258,568, 6,833,246, 7,115,400, 6,969,488, 5,912,148, 6,130,073, 7,169,560, 7,282,337, 7,482,120, 7,501,245, 6,818,395, 6,911,345, 7,501,245, 7,329,492, 7,170,050, 7,302,146, 7,313,308, and 7,476,503, each of which is hereby incorporated by reference in its entirety.

I. Exemplary Workflows

Exemplary workflows are provided herein. In some embodiments, some or all features of the partitioning and library preparation workflows may be used in combination with each other and with other features of the methods described herein.

a. Partitioning

In some embodiments, sample nucleic acid molecules, such as DNA (e.g., between 5 and 200 ng) is mixed with methyl binding domain (MBD) buffer and magnetic beads conjugated with MBD proteins and incubated overnight. Methylated DNA (hypermethylated DNA) binds the MBD protein on the magnetic beads during this incubation. Non-methylated (hypomethylated DNA) or less methylated DNA (intermediately methylated) is washed away from the beads with buffers containing increasing concentrations of salt. For example, one, two, or more fractions containing non-methylated, hypomethylated, and/or intermediately methylated DNA may be obtained from such washes. Finally, a high salt buffer is used to elute the heavily methylated DNA (hypermethylated DNA) from the MBD protein. In some embodiments, these washes result in three partitions (hypomethylated partition, intermediately methylated fraction and hypermethylated partition) of DNA having increasing levels of methylation.

In some embodiments, the three partitions of DNA are desalted and concentrated in preparation for the enzymatic steps of library preparation.

b. Library Preparation

In some embodiments (e.g., after concentrating the DNA in the partitions), the partitioned DNA is made ligatable, e.g., by extending the end overhangs of the DNA molecules are extended, and adding adenosine residues to the 3' ends of fragments and phosphorylating the 5' end of each DNA fragment. DNA ligase and adapters are added to ligate each partitioned DNA molecule with an adapter on each end. These adapters contain partition tags (e.g., non-random, non-unique barcodes) that are distinguishable from the partition tags in the adapters used in the other partitions. Either before or after making the portioned DNA ligatable and performing the ligation, at least one partition (e.g., the hypermethylated partition, or the hypermethylated partition and the intermediately methylated partition if applicable) is digested with an MSRE (e.g., an MSRE that preferentially cleaves unmethylated DNA, such as one or more, or each of HpaII, BstUI and Hin6i). Optionally, the hypomethylated partition may be digested with an MSRE that preferentially cleaves methylated DNA, such as FspEI. Optionally, the hypermethylated partition may be subjected to a procedure that affects a first nucleobase in the DNA differently from a second nucleobase in the DNA, such as any of those described herein. Where the procedure that affects a first nucleobase in the DNA differently from a second nucleobase in the DNA further partitions the hypermethylated partition, the ligation of adapters should be performed after the procedure so that the sub-partitions of the hypermethylated partition can be differentially tagged. Then, the three (or more) partitions are pooled together and are amplified (e.g., by PCR, such as with primers specific for the adapters).

Following PCR, amplified DNA may be cleaned and concentrated prior to enrichment. The amplified DNA is contacted with a collection of probes described herein (which may be, e.g., biotinylated RNA probes) that target specific regions of interest. The mixture is incubated, e.g., overnight, e.g., in a salt buffer. The probes are captured (e.g., using streptavidin magnetic beads) and separated from the amplified DNA that was not captured, such as by a series of salt washes, thereby enriching the sample. After the enrichment, the enriched sample is amplified by PCR. In some embodiments, the PCR primers contain a sample tag, thereby incorporating the sample tag into the DNA molecules. In some embodiments, DNA from different samples is pooled together and then multiplex sequenced, e.g., using an Illumina NovaSeq sequencer.

J. Compositions Comprising Captured Nucleic Acid Molecules

Provided herein is a combination comprising first and second populations of DNA, wherein the second population comprises fragments of DNA with ends, or attached tags or adapters, at a recognition site of at least one MSRE, which may be any one or any combination of the MSREs described herein. In some embodiments, the first and second populations are differentially tagged. The first population may comprise or be derived from DNA with a cytosine modification in a greater proportion than the second population. The first population may comprise a form of a first nucleobase originally present in the DNA with altered base pairing specificity and a second nucleobase without altered base pairing specificity, wherein the form of the first nucleobase originally present in the DNA prior to alteration of base pairing specificity is a modified or unmodified nucleobase, the second nucleobase is a modified or unmodified nucleobase different from the first nucleobase, and the form of the first nucleobase originally present in the DNA prior to alteration of base pairing specificity and the second nucleobase have the same base pairing specificity. In some embodiments, the cytosine modification is cytosine methylation. In some embodiments, the first nucleobase is a modified or unmodified cytosine and the second nucleobase is a modified or unmodified cytosine. The first and second nucleobase may be any of those discussed herein or with respect to subjecting the first partition to a procedure that affects a first nucleobase in the DNA differently from a second nucleobase in the DNA of the first partition. In some embodiments, the first population comprises fragments of DNA with ends, or attached tags or adapters, at a recognition site of at least one MSRE, which may be any one or any combination of the MSREs described herein.

In some embodiments, the first population comprises a sequence tag selected from a first set of one or more sequence tags and the second population comprises a sequence tag selected from a second set of one or more sequence tags, and the second set of sequence tags is different from the first set of sequence tags. The sequence tags may comprise barcodes.

In some embodiments, the first population comprises protected hmC, such as glucosylated hmC.

In some embodiments, the first population was subjected to any of the conversion procedures discussed herein, such as bisulfite conversion, Ox-BS conversion, TAB conversion, ACE conversion, TAP conversion, TAPSβ conversion, or CAP conversion. In some embodiments, the first population was subjected to protection of hmC followed by deamination of mC and/or C.

In some embodiments of the combination, the first population comprises or was derived from DNA with a cytosine modification in a greater proportion than the second population and the first population comprises first and second subpopulations, and the first nucleobase is a modified or unmodified nucleobase, the second nucleobase is a modified or unmodified nucleobase different from the first nucleobase, and the first nucleobase and the second nucleobase have the same base pairing specificity. In some embodiments, the second population does not comprise the first nucleobase. In some embodiments, the first nucleobase is a modified or unmodified cytosine, and the second nucleobase is a modified or unmodified cytosine, optionally wherein the modified cytosine is mC or hmC. In some embodiments, the first nucleobase is a modified or unmodified adenine, and the second nucleobase is a modified or unmodified adenine, optionally wherein the modified adenine is mA.

In some embodiments, the first nucleobase (e.g., a modified cytosine) is biotinylated. In some embodiments, the first nucleobase (e.g., a modified cytosine) is a product of a Huisgen cycloaddition to β-6-azide-glucosyl-5-hydroxymethylcytosine that comprises an affinity label (e.g., biotin).

In any of the combinations described herein, the captured DNA may comprise cfDNA.

The captured DNA may have any of the features described herein concerning captured sets, including, e.g., a greater concentration of the DNA corresponding to the sequence-variable target region set (normalized for footprint size as discussed above) than of the DNA corresponding to the epigenetic target region set. In some embodiments, the DNA of the captured set comprises sequence tags, which may be added to the DNA as described herein. In general, the inclusion of sequence tags results in the DNA molecules differing from their naturally occurring, untagged form. The combination may further comprise a probe set described herein or sequencing primers, each of which may differ from naturally occurring nucleic acid molecules. For example, a probe set described herein may comprise a capture moiety, and sequencing primers may comprise a non-naturally occurring label.

III. Computer Systems

Methods of the present disclosure can be implemented using, or with the aid of, computer systems. For example, such methods, which may comprise: (a) providing a biological sample of nucleic acid molecules, wherein the nucleic acid molecules comprises methylated nucleic acid molecules and unmethylated nucleic acid molecules; (b) partitioning at least a subset of the nucleic acid molecules in the biological sample based on the methylation status of the nucleic acid molecules into a plurality of partitioned sets; (c) digesting at least a subset of the one or more partitioned sets in the plurality of partitioned sets with at least one methylation sensitive restriction enzyme; (d) enriching at least a subset of the nucleic acid molecules in the plurality of partitioned sets for genomic regions of interest, wherein the at least a subset of the nucleic acid molecules comprises digested nucleic acid molecules in the one or more partitioned sets; and (e) determining methylation status at one or more genetic loci of the nucleic acid molecules in at least one of the partitioned sets, which in turn is used to determine the presence or absence of cancer in a subject.

Figure 5:
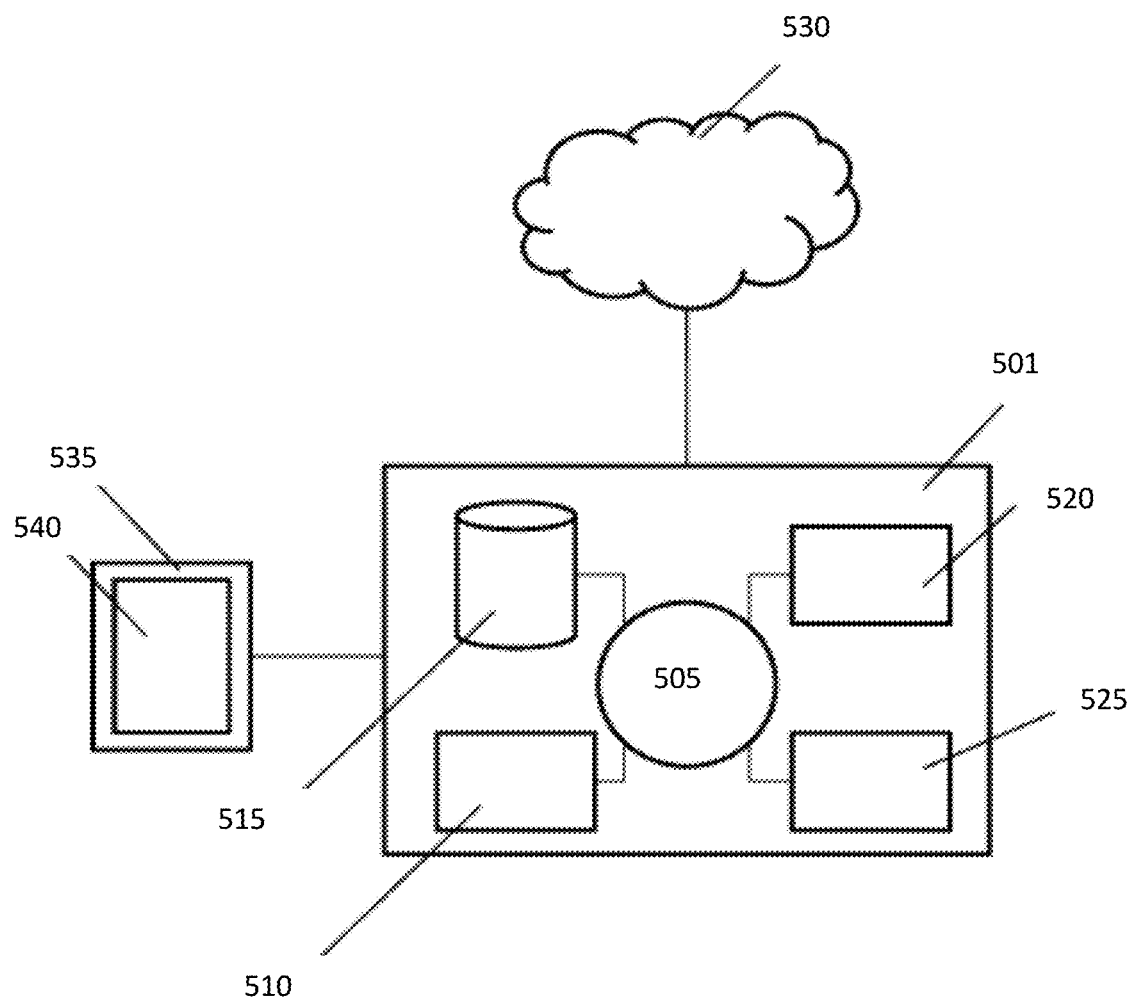
FIG. 5 schematic diagram of an example of a system suitable for use with some embodiments of the disclosure.

FIG. 5 shows a computer system 501 that is programmed or otherwise configured to implement the methods of the present disclosure. The computer system 501 can regulate various aspects sample preparation, sequencing, and/or analysis. In some examples, the computer system 501 is configured to perform sample preparation and sample analysis, including nucleic acid sequencing.

In some embodiments, the method further comprises obtaining a plurality of sequence reads generated by a nucleic acid sequencer from the sequencing; mapping the plurality of sequence reads to one or more reference sequences to generate mapped sequence reads; and processing the mapped sequence reads to determine the likelihood that the subject has cancer.

The computer system 501 includes a central processing unit (CPU, also "processor" and "computer processor" herein) 505, which can be a single core or multi core processor, or a plurality of processors for parallel processing. The computer system 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage, and/or electronic display adapters. The memory 510, storage unit 515, interface 520, and peripheral devices 525 are in communication with the CPU 505 through a communication network or bus (solid lines), such as a motherboard. The storage unit 515 can be a data storage unit (or data repository) for storing data. The computer system 501 can be operatively coupled to a computer network 530 with the aid of the communication interface 520. The computer network 530 can be the Internet, an internet and/or extranet, or an intranet and/or extranet that is in communication with the Internet. The computer network 530 in some cases is a telecommunication and/or data network. The computer network 530 can include one or more computer servers, which can enable distributed computing, such as cloud computing. The computer network 530, in some cases with the aid of the computer system 501, can implement a peer-to-peer network, which may enable devices coupled to the computer system 501 to behave as a client or a server.

The CPU 505 can execute a sequence of machine-readable instructions, which can be embodied in a program or software. The instructions may be stored in a memory location, such as the memory 510. Examples of operations performed by the CPU 405 can include fetch, decode, execute, and writeback.

The storage unit 515 can store files, such as drivers, libraries, and saved programs. The storage unit 515 can store programs generated by users and recorded sessions, as well as output(s) associated with the programs. The storage unit 515 can store user data, e.g., user preferences and user programs. The computer system 501 in some cases can include one or more additional data storage units that are external to the computer system 501, such as located on a remote server that is in communication with the computer system 501 through an intranet or the Internet. Data may be transferred from one location to another using, for example, a communication network or physical data transfer (e.g., using a hard drive, thumb drive, or other data storage mechanism).

The computer system 501 can communicate with one or more remote computer systems through the network 530. For embodiment, the computer system 501 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 501 via the network 530.

Methods as described herein can be implemented by way of machine (e.g., computer processor) executable code stored on an electronic storage location of the computer system 501, such as, for example, on the memory 510 or electronic storage unit 515. The machine executable or machine-readable code can be provided in the form of software. During use, the code can be executed by the processor 505. In some cases, the code can be retrieved from the storage unit 515 and stored on the memory 510 for ready access by the processor 505. In some situations, the electronic storage unit 515 can be precluded, and machine-executable instructions are stored on memory 510.

In an aspect, the present disclosure provides a non-transitory computer-readable medium comprising computer-executable instructions which, when executed by at least one electronic processor, perform at least a portion of a method comprising: (a) providing a biological sample of nucleic acid molecules, wherein the nucleic acid molecules comprises methylated nucleic acid molecules and unmethylated nucleic acid molecules; (b) partitioning at least a subset of the nucleic acid molecules in the biological sample based on the methylation status of the nucleic acid molecules into a plurality of partitioned sets; (c) digesting at least a subset of the one or more partitioned sets in the plurality of partitioned sets with at least one methylation sensitive restriction enzyme; (d) enriching at least a subset of the nucleic acid molecules in the plurality of partitioned sets for genomic regions of interest, wherein the at least a subset of the nucleic acid molecules comprises digested nucleic acid molecules in the one or more partitioned sets; and (e) determining methylation status at one or more genetic loci of the nucleic acid molecules in at least one of the partitioned sets, which in turn is used to detect the presence or absence of cancer in a subject.

The code can be pre-compiled and configured for use with a machine have a processor adapted to execute the code or can be compiled during runtime. The code can be supplied in a programming language that can be selected to enable the code to execute in a pre-compiled or as-compiled fashion.

Aspects of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming.

All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as those used across physical interfaces between local devices, through wired and optical landline networks, and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Hence, a machine-readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards, paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 501 can include or be in communication with an electronic display 535 that comprises a user interface (UI) 540 for providing, for example, one or more results of sample analysis. Examples of UIs include, without limitation, a graphical user interface (GUI) and web-based user interface.

Additional details relating to computer systems and networks, databases, and computer program products are also provided in, for example, Peterson, *Computer Networks: A Systems Approach*, Morgan Kaufmann, 5th Ed. (2011), Kurose, *Computer Networking: A Top-Down Approach*, Pearson, 7$^{th}$ Ed. (2016), Elmasri, *Fundamentals of Database Systems*, Addison Wesley, 6th Ed. (2010), Coronel, *Database Systems: Design, Implementation, & Management*, Cengage Learning, 11$^{th}$ Ed. (2014), Tucker, *Programming Languages*, McGraw-Hill Science/Engineering/Math, 2nd Ed. (2006), and Rhoton, *Cloud Computing Architected. Solution Design Handbook*, Recursive Press (2011), each of which is hereby incorporated by reference in its entirety.

IV. Applications

A. Cancer and Other Diseases

The present methods can be used to diagnose presence or absence of conditions, particularly cancer, in a subject, to characterize conditions (e.g., staging cancer or determining heterogeneity of a cancer), monitor response to treatment of a condition, effect prognosis risk of developing a condition or subsequent course of a condition. The present disclosure can also be useful in determining the efficacy of a particular treatment option. Successful treatment options may increase the amount of copy number variation or rare mutations detected in subject's blood if the treatment is successful as more cancers may die and shed DNA. In other examples, this may not occur. In another example, perhaps certain treatment options may be correlated with genetic profiles of cancers over time. This correlation may be useful in selecting a therapy. In some embodiments, hypermethylation variable epigenetic target regions are analyzed to determine whether they show hypermethylation characteristic of tumor cells or cells that do not ordinarily contribute significantly to cfDNA and/or hypomethylation variable epigenetic target regions are analyzed to determine whether they show hypomethylation characteristic of tumor cells or cells that do not ordinarily contribute significantly to cfDNA.

Additionally, if a cancer is observed to be in remission after treatment, the present methods can be used to monitor residual disease or recurrence of disease.

In some embodiments, the methods and systems disclosed herein may be used to identify customized or targeted therapies to treat a given disease or condition in patients based on the classification of a nucleic acid variant as being of somatic or germline origin. Typically, the disease under consideration is a type of cancer. Non-limiting examples of such cancers include biliary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, Wilms tumor, leukemia, acute lymphocytic leukemia (ALL), acute myeloid leukemia (AML), chronic lymphocytic leukemia (CLL), chronic myeloid leukemia (CIVIL), chronic myelomonocytic leukemia (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T cell lymphomas, non-Hodgkin lymphoma, precursor T-lymphoblastic lymphoma/leukemia, peripheral T cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas. Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma. Type and/or stage of cancer can be detected from genetic variations including mutations, rare mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, and abnormal changes in nucleic acid 5-methylcytosine.

Genetic data can also be used for characterizing a specific form of cancer. Cancers are often heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer and allow either a subject or practitioner to adapt treatment options in accord with the progress of the disease. Some cancers can progress to become more aggressive and genetically unstable. Other cancers may remain benign, inactive or dormant. The system and methods of this disclosure may be useful in determining disease progression.

Further, the methods of the disclosure may be used to characterize the heterogeneity of an abnormal condition in a subject. Such methods can include, e.g., generating a genetic profile of extracellular polynucleotides derived from the subject, wherein the genetic profile comprises a plurality of data resulting from copy number variation and rare mutation analyses. In some embodiments, an abnormal condition is cancer. In some embodiments, the abnormal condition may be one resulting in a heterogeneous genomic population. In the example of cancer, some tumors are known to comprise tumor cells in different stages of the cancer. In other examples, heterogeneity may comprise multiple foci of disease. Again, in the example of cancer, there may be multiple tumor foci, perhaps where one or more foci are the result of metastases that have spread from a primary site.

The present methods can be used to generate or profile, fingerprint or set of data that is a summation of genetic information derived from different cells in a heterogeneous disease. This set of data may comprise copy number variation, epigenetic variation, and mutation analyses alone or in combination.

The present methods can be used to diagnose, prognose, monitor or observe cancers, or other diseases. In some embodiments, the methods herein do not involve the diagnosing, prognosing or monitoring a fetus and as such are not directed to non-invasive prenatal testing. In other embodiments, these methodologies may be employed in a pregnant subject to diagnose, prognose, monitor or observe cancers or other diseases in an unborn subject whose DNA and other polynucleotides may co-circulate with maternal molecules.

Non-limiting examples of other genetic-based diseases, disorders, or conditions that are optionally evaluated using the methods and systems disclosed herein include achondroplasia, alpha-1 antitrypsin deficiency, antiphospholipid syndrome, autism, autosomal dominant polycystic kidney disease, Charcot-Marie-Tooth (CMT), cri du chat, Crohn's disease, cystic fibrosis, Dercum disease, down syndrome, Duane syndrome, Duchenne muscular dystrophy, Factor V Leiden thrombophilia, familial hypercholesterolemia, familial Mediterranean fever, fragile X syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency (SCID), sickle cell disease, spinal muscular atrophy, Tay-Sachs, thalassemia, trimethylaminuria, Turner syndrome, velocardiofacial syndrome, WAGR syndrome, Wilson disease, or the like.

In some embodiments, a method described herein comprises detecting a presence or absence of DNA originating or derived from a tumor cell at a preselected timepoint following a previous cancer treatment of a subject previously diagnosed with cancer using a set of sequence information obtained as described herein. The method may further comprise determining a cancer recurrence score that is indicative of the presence or absence of the DNA originating or derived from the tumor cell for the test subject.

Where a cancer recurrence score is determined, it may further be used to determine a cancer recurrence status. The cancer recurrence status may be at risk for cancer recurrence, e.g., when the cancer recurrence score is above a predetermined threshold. The cancer recurrence status may be at low or lower risk for cancer recurrence, e.g., when the cancer recurrence score is above a predetermined threshold. In particular embodiments, a cancer recurrence score equal to the predetermined threshold may result in a cancer recurrence status of either at risk for cancer recurrence or at low or lower risk for cancer recurrence.

In some embodiments, a cancer recurrence score is compared with a predetermined cancer recurrence threshold, and the test subject is classified as a candidate for a subsequent cancer treatment when the cancer recurrence score is above the cancer recurrence threshold or not a candidate for therapy when the cancer recurrence score is below the cancer recurrence threshold. In particular embodiments, a cancer recurrence score equal to the cancer recurrence threshold may result in classification as either a candidate for a subsequent cancer treatment or not a candidate for therapy.

The methods discussed above may further comprise any compatible feature or features set forth elsewhere herein, including in the section regarding methods of determining a risk of cancer recurrence in a test subject and/or classifying a test subject as being a candidate for a subsequent cancer treatment.

B. Methods of Determining a Risk of Cancer Recurrence in a Test Subject and/or Classifying a Test Subject as being a Candidate for a Subsequent Cancer Treatment In some embodiments, a method provided herein is a method of determining a risk of cancer recurrence in a test subject. In some embodiments, a method provided herein is a method of classifying a test subject as being a candidate for a subsequent cancer treatment.

Any of such methods may comprise collecting DNA (e.g., originating or derived from a tumor cell) from the test subject diagnosed with the cancer at one or more preselected timepoints following one or more previous cancer treatments to the test subject. The subject may be any of the subjects described herein. The DNA may be cfDNA. The DNA may be obtained from a tissue sample.

Any of such methods may comprise capturing a plurality of sets of target regions from DNA from the subject, wherein the plurality of target region sets comprises a sequence-variable target region set and an epigenetic target region set, whereby a captured set of DNA molecules is produced. The capturing step may be performed according to any of the embodiments described elsewhere herein.

In any of such methods, the previous cancer treatment may comprise surgery, administration of a therapeutic composition, and/or chemotherapy.

Any of such methods may comprise sequencing the captured DNA molecules, whereby a set of sequence information is produced. The captured DNA molecules of the sequence-variable target region set may be sequenced to a greater depth of sequencing than the captured DNA molecules of the epigenetic target region set.

Any of such methods may comprise detecting a presence or absence of DNA originating or derived from a tumor cell at a preselected timepoint using the set of sequence information. The detection of the presence or absence of DNA originating or derived from a tumor cell may be performed according to any of the embodiments thereof described elsewhere herein.

Methods of determining a risk of cancer recurrence in a test subject may comprise determining a cancer recurrence score that is indicative of the presence or absence, or amount, of the DNA originating or derived from the tumor cell for the test subject. The cancer recurrence score may further be used to determine a cancer recurrence status. The cancer recurrence status may be at risk for cancer recurrence, e.g., when the cancer recurrence score is above a predetermined threshold. The cancer recurrence status may be at low or lower risk for cancer recurrence, e.g., when the cancer recurrence score is above a predetermined threshold. In particular embodiments, a cancer recurrence score equal to the predetermined threshold may result in a cancer recurrence status of either at risk for cancer recurrence or at low or lower risk for cancer recurrence.

Methods of classifying a test subject as being a candidate for a subsequent cancer treatment may comprise comparing the cancer recurrence score of the test subject with a predetermined cancer recurrence threshold, thereby classifying the test subject as a candidate for the subsequent cancer treatment when the cancer recurrence score is above the cancer recurrence threshold or not a candidate for therapy when the cancer recurrence score is below the cancer recurrence threshold. In particular embodiments, a cancer recurrence score equal to the cancer recurrence threshold may result in classification as either a candidate for a subsequent cancer treatment or not a candidate for therapy. In some embodiments, the subsequent cancer treatment comprises chemotherapy or administration of a therapeutic composition.

Any of such methods may comprise determining a disease-free survival (DFS) period for the test subject based on the cancer recurrence score; for example, the DFS period may be 1 year, 2 years, 3, years, 4 years, 5 years, or 10 years.

In some embodiments, the set of sequence information comprises sequence-variable target region sequences, and determining the cancer recurrence score may comprise determining at least a first subscore indicative of the amount of SNVs, insertions/deletions, CNVs and/or fusions present in sequence-variable target region sequences.

In some embodiments, a number of mutations in the sequence-variable target regions chosen from 1, 2, 3, 4, or 5 is sufficient for the first subscore to result in a cancer recurrence score classified as positive for cancer recurrence. In some embodiments, the number of mutations is chosen from 1, 2, or 3.

In some embodiments, the set of sequence information comprises epigenetic target region sequences, and determining the cancer recurrence score comprises determining a second subscore indicative of the changes in the epigenetic features in the epigenetic target region sequences e.g., methylation of hypermethylation variable target regions and/or perturbed fragmentation of fragmentation variable target regions, where "perturbed" means different from DNA found in a corresponding sample from a healthy subject. In some such embodiments, the determining the cancer recurrence score comprises determining a second subscore indicative of the amount of molecules (obtained from the epigenetic target region sequences) that represent an epigenetic state different from DNA found in a corresponding sample from a healthy subject (e.g., cfDNA found in a blood sample from a healthy subject, or DNA found in a tissue sample from a healthy subject where the tissue sample is of the same type of tissue as was obtained from the test subject). These abnormal molecules (i.e., molecules with an epigenetic state different from DNA found in a corresponding sample from a healthy subject) may be consistent with epigenetic changes associated with cancer, e.g., methylation of hypermethylation variable target regions and/or perturbed fragmentation of fragmentation variable target regions.

In some embodiments, a proportion of molecules corresponding to the hypermethylation variable target region set and/or fragmentation variable target region set that indicate hypermethylation in the hypermethylation variable target region set and/or abnormal fragmentation in the fragmentation variable target region set greater than or equal to a value in the range of 0.001%-10% is sufficient for the second subscore to be classified as positive for cancer recurrence. The range may be 0.001%-1%, 0.005%-1%, 0.01%-5%, 0.01%-2%, or 0.01%-1%.

In some embodiments, any of such methods may comprise determining a fraction of tumor DNA from the fraction of molecules in the set of sequence information that indicate one or more features indicative of origination from a tumor cell. This may be done for molecules corresponding to some or all of the epigenetic target regions, e.g., including one or both of hypermethylation variable target regions and fragmentation variable target regions (hypermethylation of a hypermethylation variable target region and/or abnormal fragmentation of a fragmentation variable target region may be considered indicative of origination from a tumor cell). This may be done for molecules corresponding to sequence variable target regions, e.g., molecules comprising alterations consistent with cancer, such as SNVs, indels, CNVs, and/or fusions. The fraction of tumor DNA may be determined based on a combination of molecules corresponding to epigenetic target regions and molecules corresponding to sequence variable target regions.

Determination of a cancer recurrence score may be based at least in part on the fraction of tumor DNA, wherein a fraction of tumor DNA greater than a threshold in the range of 10-11 to 1 or 10-10 to 1 is sufficient for the cancer recurrence score to be classified as positive for cancer recurrence. In some embodiments, a fraction of tumor DNA greater than or equal to a threshold in the range of 10-10 to 10-9, 10-9 to 10-8, 10-8 to 10-7, 10-7 to 10-6, 10-6 to 10-5, 10-5 to 10-4, 10-4 to 10-3, 10-3 to 10-2, or 10-2 to 10-1 is sufficient for the cancer recurrence score to be classified as positive for cancer recurrence. In some embodiments, the fraction of tumor DNA greater than a threshold of at least 10-7 is sufficient for the cancer recurrence score to be classified as positive for cancer recurrence. A determination that a fraction of tumor DNA is greater than a threshold, such as a threshold corresponding to any of the foregoing embodiments, may be made based on a cumulative probability. For example, the sample was considered positive if the cumulative probability that the tumor fraction was greater than a threshold in any of the foregoing ranges exceeds a probability threshold of at least 0.5, 0.75, 0.9, 0.95, 0.98, 0.99, 0.995, or 0.999. In some embodiments, the probability threshold is at least 0.95, such as 0.99.

In some embodiments, the set of sequence information comprises sequence-variable target region sequences and epigenetic target region sequences, and determining the cancer recurrence score comprises determining a first subscore indicative of the amount of SNVs, insertions/deletions, CNVs and/or fusions present in sequence-variable target region sequences and a second subscore indicative of the amount of abnormal molecules in epigenetic target region sequences, and combining the first and second subscores to provide the cancer recurrence score. Where the first and second subscores are combined, they may be combined by applying a threshold to each subscore independently (e.g., greater than a predetermined number of mutations (e.g., >1) in sequence-variable target regions, and greater than a predetermined fraction of abnormal molecules (i.e., molecules with an epigenetic state different from the DNA found in a corresponding sample from a healthy subject; e.g., tumor) in epigenetic target regions), or training a machine learning classifier to determine status based on a plurality of positive and negative training samples.

In some embodiments, a value for the combined score in the range of −4 to 2 or −3 to 1 is sufficient for the cancer recurrence score to be classified as positive for cancer recurrence.

In any embodiment where a cancer recurrence score is classified as positive for cancer recurrence, the cancer recurrence status of the subject may be at risk for cancer recurrence and/or the subject may be classified as a candidate for a subsequent cancer treatment.

In some embodiments, the cancer is any one of the types of cancer described elsewhere herein, e.g., colorectal cancer.

C. Therapies and Related Administration

In certain embodiments, the methods disclosed herein relate to identifying and administering customized therapies to patients given the status of a nucleic acid variant as being of somatic or germline origin. In some embodiments, essentially any cancer therapy (e.g., surgical therapy, radiation therapy, chemotherapy, and/or the like) may be included as part of these methods. Typically, customized therapies include at least one immunotherapy (or an immunotherapeutic agent). Immunotherapy refers generally to methods of enhancing an immune response against a given cancer type. In certain embodiments, immunotherapy refers to methods of enhancing a T cell response against a tumor or cancer.

In certain embodiments, the status of a nucleic acid variant from a sample from a subject as being of somatic or germline origin may be compared with a database of comparator results from a reference population to identify customized or targeted therapies for that subject. Typically, the reference population includes patients with the same cancer or disease type as the test subject and/or patients who are receiving, or who have received, the same therapy as the test subject. A customized or targeted therapy (or therapies) may be identified when the nucleic variant and the comparator results satisfy certain classification criteria (e.g., are a substantial or an approximate match).

In certain embodiments, the customized therapies described herein are typically administered parenterally (e.g., intravenously or subcutaneously). Pharmaceutical compositions containing an immunotherapeutic agent are typically administered intravenously. Certain therapeutic agents are administered orally. However, customized therapies (e.g., immunotherapeutic agents, etc.) may also be administered by methods such as, for example, buccal, sublingual, rectal, vaginal, intraurethral, topical, intraocular, intranasal, and/or intraauricular, which administration may include tablets, capsules, granules, aqueous suspensions, gels, sprays, suppositories, salves, ointments, or the like.

D. Kits

Also provided are kits comprising the compositions as described herein. The kits can be useful in performing the methods as described herein. The kits comprise at least one MSRE. In some embodiments, a kit also comprises a first reagent for partitioning a sample into a plurality of partitions as described herein, such as any of the partitioning reagents described elsewhere herein. In some embodiments, a kit comprises a second reagent for subjecting the first partition to a procedure that affects a first nucleobase in the DNA differently from a second nucleobase in the DNA of the first partition, wherein the first nucleobase is a modified or unmodified nucleobase, the second nucleobase is a modified or unmodified nucleobase different from the first nucleobase, and the first nucleobase and the second nucleobase have the same base pairing specificity (e.g., any of the reagents described elsewhere herein for converting a nucleobase such as cytosine or methylated cytosine to a different nucleobase). The kit may comprise the first and second reagents and additional elements as discussed below and/or elsewhere herein.

Kits may further comprise a plurality of oligonucleotide probes that selectively hybridize to least 5, 6, 7, 8, 9, 10, 20, 30, 40 or all genes selected from the group consisting of ALK, APC, BRAF, CDKN2A, EGFR, ERBB2, FBXW7, KRAS, MYC, NOTCH1, NRAS, PIK3CA, PTEN, RBI, TP53, MET, AR, ABL1, AKT1, ATM, CDH1, CSF1R, CTNNB1, ERBB4, EZH2, FGFR1, FGFR2, FGFR3, FLT3, GNA11, GNAQ, GNAS, HNF1A, HRAS, IDH1, IDH2, JAK2, JAK3, KDR, KIT, MLH1, MPL, NPM1, PDGFRA, PROC, PTPN11, RET, SMAD4, SMARCB1, SMO, SRC, STK11, VHL, TERT, CCND1, CDK4, CDKN2B, RAF1, BRCA1, CCND2, CDK6, NF1, TP53, ARID 1 A, BRCA2, CCNE1, ESR1, RIT1, GATA3, MAP2K1, RHEB, ROS1, ARAF, MAP2K2, NFE2L2, RHOA, and NTRK1. The number genes to which the oligonucleotide probes can selectively hybridize can vary. For example, the number of genes can comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54. The kit can include a container that includes the plurality of oligonucleotide probes and instructions for performing any of the methods described herein.

The oligonucleotide probes can selectively hybridize to exon regions of the genes, e.g., of the at least 5 genes. In some cases, the oligonucleotide probes can selectively hybridize to at least 30 exons of the genes, e.g., of the at least 5 genes. In some cases, the multiple probes can selectively hybridize to each of the at least 30 exons. The probes that hybridize to each exon can have sequences that overlap with at least 1 other probe. In some embodiments, the oligoprobes can selectively hybridize to non-coding regions of genes disclosed herein, for example, intronic regions of the genes. The oligoprobes can also selectively hybridize to regions of genes comprising both exonic and intronic regions of the genes disclosed herein.

Any number of exons can be targeted by the oligonucleotide probes. For example, at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 400, 500, 600, 700, 800, 900, 1,000, or more, exons can be targeted.

The kit can comprise at least 4, 5, 6, 7, or 8 different library adaptors having distinct molecular barcodes and identical sample barcodes. The library adaptors may not be sequencing adaptors. For example, the library adaptors do not include flow cell sequences or sequences that permit the formation of hairpin loops for sequencing. The different variations and combinations of molecular barcodes and sample barcodes are described throughout, and are applicable to the kit. Further, in some cases, the adaptors are not sequencing adaptors. Additionally, the adaptors provided with the kit can also comprise sequencing adaptors. A sequencing adaptor can comprise a sequence hybridizing to one or more sequencing primers. A sequencing adaptor can further comprise a sequence hybridizing to a solid support, e.g., a flow cell sequence. For example, a sequencing adaptor can be a flow cell adaptor. The sequencing adaptors can be attached to one or both ends of a polynucleotide fragment. In some cases, the kit can comprise at least 8 different library adaptors having distinct molecular barcodes and identical sample barcodes. The library adaptors may not be sequencing adaptors. The kit can further include a sequencing adaptor having a first sequence that selectively hybridizes to the library adaptors and a second sequence that selectively hybridizes to a flow cell sequence. In another example, a sequencing adaptor can be hairpin shaped. For example, the hairpin shaped adaptor can comprise a complementary double stranded portion and a loop portion, where the double stranded portion can be attached {e.g., ligated) to a double-stranded polynucleotide. Hairpin shaped sequencing adaptors can be attached to both ends of a polynucleotide fragment to generate a circular molecule, which can be sequenced multiple times. A sequencing adaptor can be up to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more bases from end to end. The sequencing adaptor can comprise 20-30, 20-40, 30-50, 30-60, 40-60, 40-70, 50-60, 50-70, bases from end to end. In a particular example, the sequencing adaptor can comprise 20-30 bases from end to end. In another example, the sequencing adaptor can comprise 50-60 bases from end to end. A sequencing adaptor can comprise one or more barcodes. For example, a sequencing adaptor can comprise a sample barcode. The sample barcode can comprise a pre-determined sequence. The sample barcodes can be used to identify the source of the polynucleotides. The sample barcode can be at least 1, 2, 3, 4, 5, 6, 7, 8, 9, 10, 11, 12, 13, 14, 15, 16, 17, 18, 19, 20, 21, 22, 23, 24, 25, or more (or any length as described throughout) nucleic acid bases, e.g., at least 8 bases. The barcode can be contiguous or non-contiguous sequences, as described above.

The library adaptors can be blunt ended and Y-shaped and can be less than or equal to 40 nucleic acid bases in length. Other variations of the can be found throughout and are applicable to the kit.

EXAMPLES

The following examples are provided to illustrate certain aspects of the disclosed methods. The examples do not limit the disclosure.

Example 1: Reduction of Technical Noise by Digestion of Nonspecifically Partitioned DNA A pool of cfDNA from two healthy normal samples was combined, from which 18.6 ng was used as input to a MBD-partitioning assay described herein. To a subset of the samples, cfDNA from a colorectal cancer sample (CRC) with 0.5% MAF (somatic allele fraction) was added, resulting in a diluted CRC sample with 0.16% MAF. Three sets of normal samples and diluted CRC samples were used in the assay. The three sets of samples were then partitioned using MBD protein into three partitions (hypermethylated (hyper), intermediate (residual), and hypomethylated (hypo) partitions). Following cleanup, the cfDNA molecules in each partition was ligated with partition-specific adapters comprising molecular barcodes. The molecular barcodes used in hyper and residual partition are selected such that they do not have MSRE recognition sites, so they are not digested in the downstream processing (irrespective of cfDNA methylation state). Post-ligation, ligation cleanups were performed. Following the ligation cleanup, the hyper and residual partitions were subjected to MSRE digestion reactions. A first set of the samples (normal and diluted CRC samples) were treated with BstUI and HpaII and another set of the samples were treated BstUI, HpaII and Hin6I enzymes. The third set of samples were run through a mock digest (no MSREs) in the MBD-partitioning assay as a control. After the MSRE digestion, the enzymes were heat inactivated (65 C, 20 min) and cleaned up using SPRI beads. After the digest cleanups, the hyper, residual and (non-digested) hypo partitions (adapter-ligated cfDNA) were combined and processed through an NGS assay workflow comprising PCR amplification; enrichment of molecules in genomic regions of interest; pooling of samples thereby allowing multiplexed sequencing and sequencing the pooled sample using NovaSeq. In an alternative procedure the hypo partition may additionally be contacted with one or more MSREs having a methylated recognition site to cleave nonspecifically partitioned DNA in the hypo partition.

Figure 6:
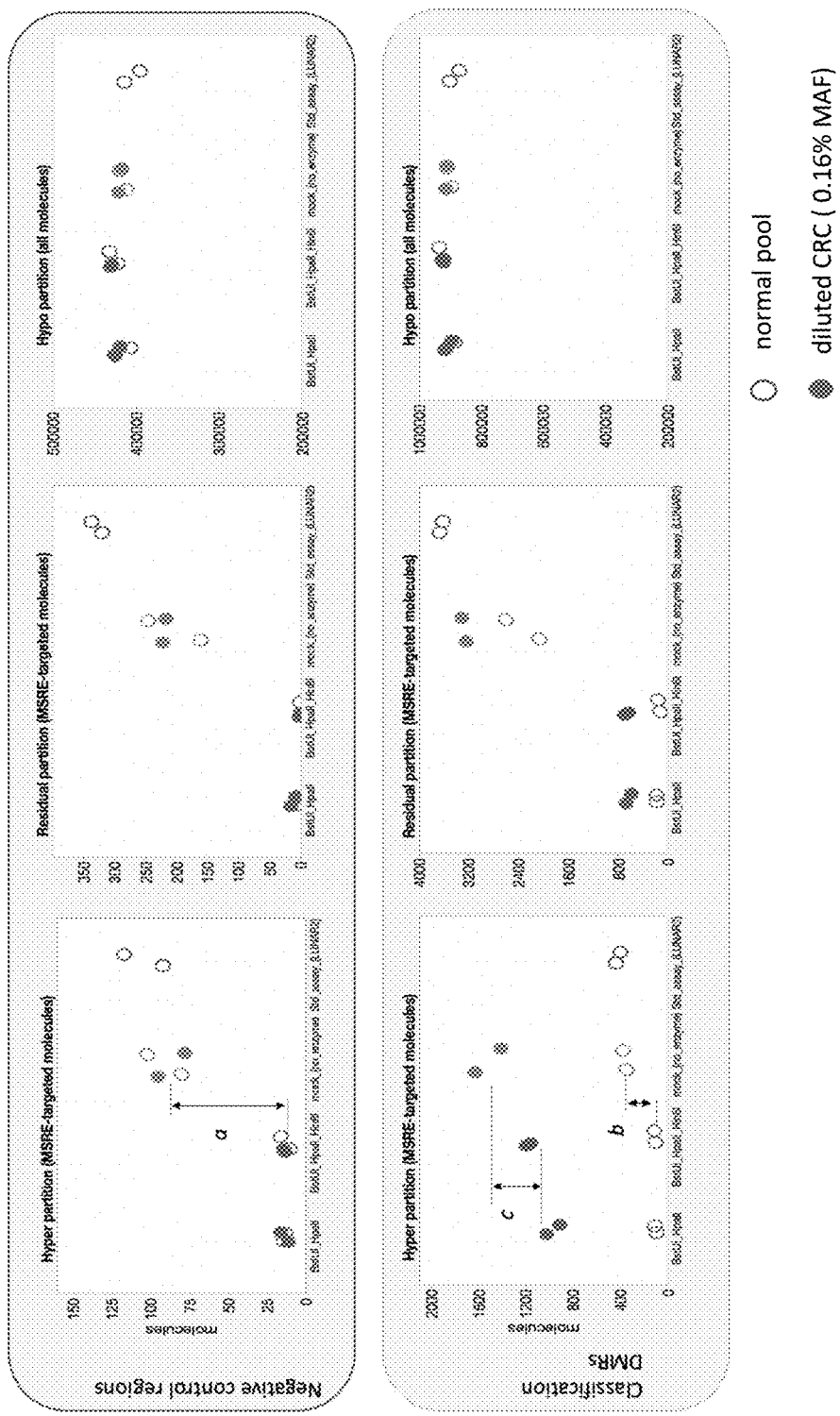
FIG. 6 shows the molecule count in the three partitions with and without MSRE treatments in normal and diluted CRC samples.

FIG. 6 clearly shows the increase in cancer methylation signal at DMRs relative to the technical noise from unmethylated molecules in normal samples when the MSRE digestion was applied. In the negative control regions (where the DNA molecules are non-methylated at almost all times irrespective of the disease state) shown in FIG. 6, "a" clearly indicates that it was clear that the MSRE digestion removes the unmethylated molecules that mis-partitioned into the hyper partition—90 molecules were partitioned into hyper partition in the mock digestion whereas in BstUI, HpaII and Hin6I digestion the molecule count was reduced to 10. In the classification DMRs shown in FIG. 6, cfDNA molecules were removed by much higher proportion in normal samples (b; 350→100) than diluted CRC samples (c; 1500→1100) upon digestion with MSREs.

Example 2: Analysis of cfDNA to Detect the Presence of Absence of a Tumor

A set of patient samples are analyzed by a blood-based NGS assay at Guardant Health (Redwood City, CA, USA) to detect the presence or absence of cancer. cfDNA is extracted from the plasma of these patients. cfDNA of the patient samples is then combined with methyl binding domain (MBD) buffers and magnetic beads conjugated with an MBD protein and incubated overnight. Methylated cfDNA (if present, in the cfDNA sample) is bound to the MBD protein during this incubation. Non-methylated or less methylated DNA is washed away from the beads with buffers containing increasing concentrations of salt. Finally, a high salt buffer is used to wash the heavily methylated DNA away from the MBD protein. These washes result in three partitions (hypomethylated, residual methylation and hypermethylated partitions) of increasingly methylated cfDNA.

Optionally, the cfDNA molecules in the hypermethylated partition are subjected to enzymatic modification (EM) with whereby unmodified cytosines, but not mC and hmC, undergo deamination, thereby marking nonspecifically partitioned hypomethylated molecules in the first partition by conversion of unmodified cytosines to uracils.

After concentrating the cfDNA in the partitions, the end overhangs of the partitioned cfDNA are extended, and adenosine residues are added to the 3' ends of the cfDNA fragment by the polymerase during the extension. The 5' end of each fragment is phosphorylated. These modifications make the partitioned cfDNA ligatable. DNA ligase and adapters are added to ligate each partitioned cfDNA molecule with an adapter on each end. These adapters contain non-unique molecular barcodes and each partition is ligated with adapters having non-unique molecular barcodes that is distinguishable from the barcodes in the adapters used in the other partitions.

The cfDNA in the hypomethylated partition is contacted with one or more MSREs having a methylated recognition site. The enzymes cleave at least a portion of nonspecifically partitioned DNA in the hypomethylated partition. Alternatively or in addition, the cfDNA in the hypermethylated partition is contacted with one or more MSREs having an unmethylated recognition site. The enzymes cleave at least a portion of nonspecifically partitioned DNA in the hypermethylated partition.

After ligation, the four partitions are pooled together and are amplified by PCR. Molecules that were cleaved by the one or more MSREs do not undergo exponential amplification because they do not have an adapter on each end.

Following PCR, amplified DNA is washed and concentrated prior to enrichment. Once concentrated, the amplified DNA is combined with a salt buffer and biotinylated RNA probes that comprise probes for a sequence-variable target region set and probes for an epigenetic target region set and this mixture is incubated overnight. The probes for the sequence-variable region set has a footprint of about 50 kb and the probes for the epigenetic target region set has a footprint of about 500 kb. The probes for the sequence-variable target region set comprise oligonucleotides targeting at least a subset of genes identified in Tables 3-5 and the probes for the epigenetic target region set comprises oligonucleotides targeting a selection of hypermethylation variable target regions, hypomethylation variable target regions, CTCF binding target regions, transcription start site target regions, focal amplification target regions and methylation control regions.

The biotinylated RNA probes (hybridized to DNA) are captured by streptavidin magnetic beads and separated from the amplified DNA that are not captured by a series of salt based washes, thereby enriching the sample. After enrichment, an aliquot of the enriched sample is sequenced using Illumina NovaSeq sequencer. The sequence reads generated by the sequencer are then analyzed using bioinformatic tools/algorithms. The molecular barcodes are used to identify unique molecules as well as for deconvolution of the sample into molecules that were differentially MBD-partitioned. The method described in this example, apart from providing information on the overall level methylation (i.e., methylated cytosine residues) of a molecule based on its partition, including with increased accuracy and/or confidence due to the cleavage of nonspecifically partitioned cfDNA in the hypomethylated partition, can also provide a higher resolution information about the location of methylated cytosines based on the conversion of unmethylated cytosines in the hypermethylated partition. The sequence-variable target region sequences are analyzed by detecting genomic alterations such as SNVs, insertions, deletions and fusions that can be called with enough support that differentiates real tumor variants from technical errors (for e.g., PCR errors, sequencing errors). The epigenetic target region sequences are analyzed independently to detect methylation status of cfDNA molecules in regions that have been shown to be differentially methylated, e.g., in potentially cancerous tissue compared to healthy cfDNA. Finally, the results of both analysis are combined to produce a final tumor present/absent call.

Example 3: Analysis of Methylation at Single Nucleotide Resolution in cfDNA Samples from Healthy Subjects and Subjects with Early-Stage Colorectal Cancer Samples of cfDNA from healthy subjects and subjects with early-stage colorectal cancer were analyzed as follows. cfDNA was partitioned using MBD to provide a hypermethylated partition, an intermediate partition, and a hypomethylated partition. The partitioned DNA of each partition was ligated to adapters and subjected to an EM-seq conversion procedure whereby unmodified cytosines, but not mC and hmC, undergo deamination, although in an alternative procedure the partitioned DNA of the hypermethylated partition could be contacted with a MSRE having an unmethylated recognition site as described herein. Following such deamination, the partitions were prepared for sequencing and subjected to whole-genome sequencing. Each partition was sequenced separately, although in an alternative procedure the partitions could be differentially tagged (e.g., after partitioning and before EM-seq conversion, or after partitioning and EM-seq conversion and before further preparation for sequencing), pooled, and processed sequenced in parallel.

Figure 7:
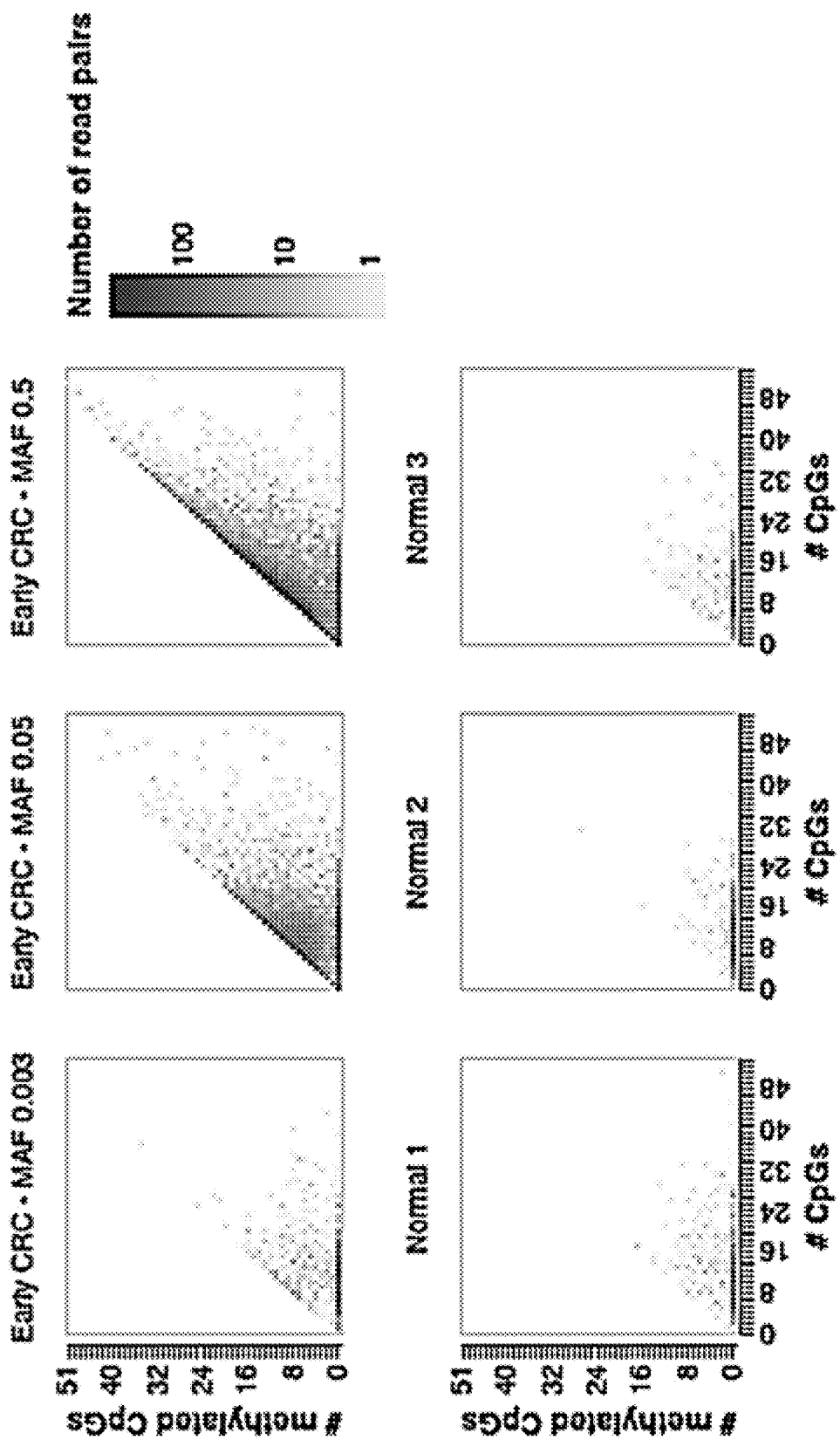
FIG. 7 shows CpG methylation quantification results obtained as described in Example 3 for three samples from subjects with early stage colorectal cancer ("Early CRC") and three healthy subjects ("Normal"). For the Early CRC plots, MAF indicates mutant allele fraction.

Sequence data from hypermethylation variable target regions was isolated bioinformatically, although in an alternative procedure target regions could be enriched in vitro before sequencing. Per-base methylation for the hypermethylation variable target regions was quantified as shown in FIG. 7, which shows the number of methylated CpG per molecule in the hypermethylation variable target regions from the hypermethylated partition. The x-axis indicates the total number of CpGs per molecule, such that points along the diagonal represent molecules with methylation at every CpG. Thus, it was possible to analyze methylation at single-base resolution and quantify per base methylation and partial molecule methylation of the MBD-partitioned material. The samples from subjects with colorectal cancer exhibited much higher overall methylation in these regions than samples from healthy subjects.

Example 4: Analysis of MDRE-Digested cfDNA

Figures 8A, 8B:
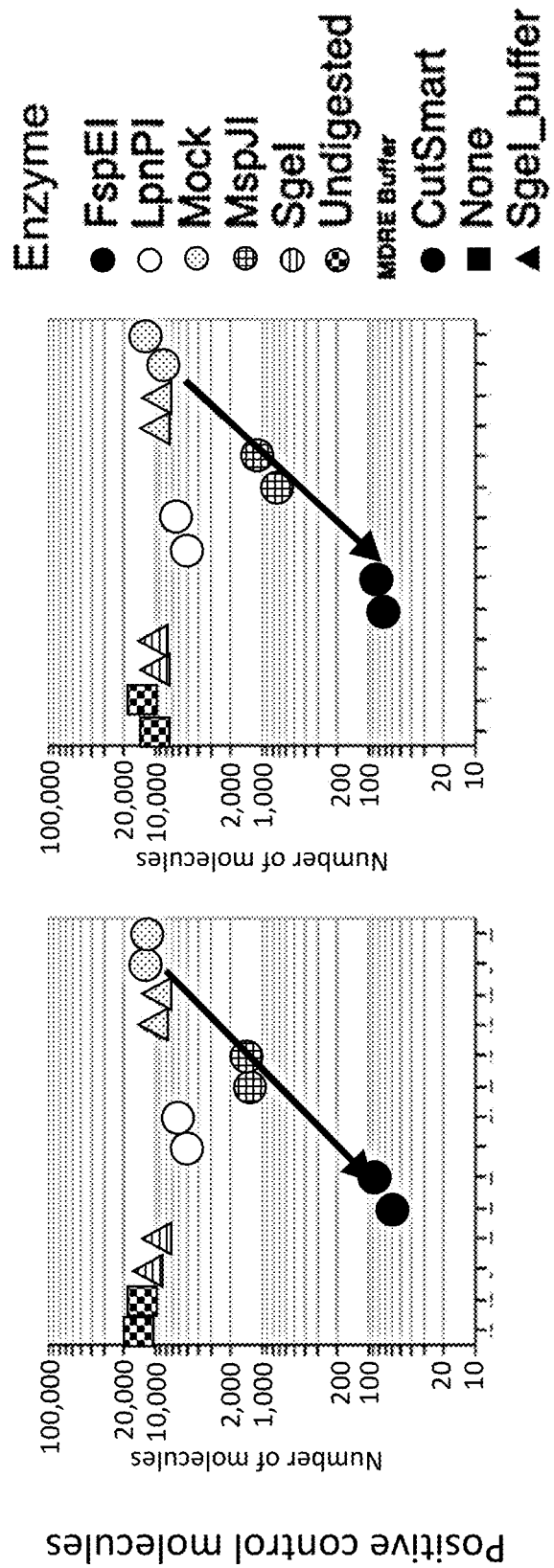
FIGS. 8A-D show counts of positive and negative control molecules having FspEI palindromic sites for the indicated enzyme and buffer conditions, as described in Example 4.
Figures 8C, 8D:
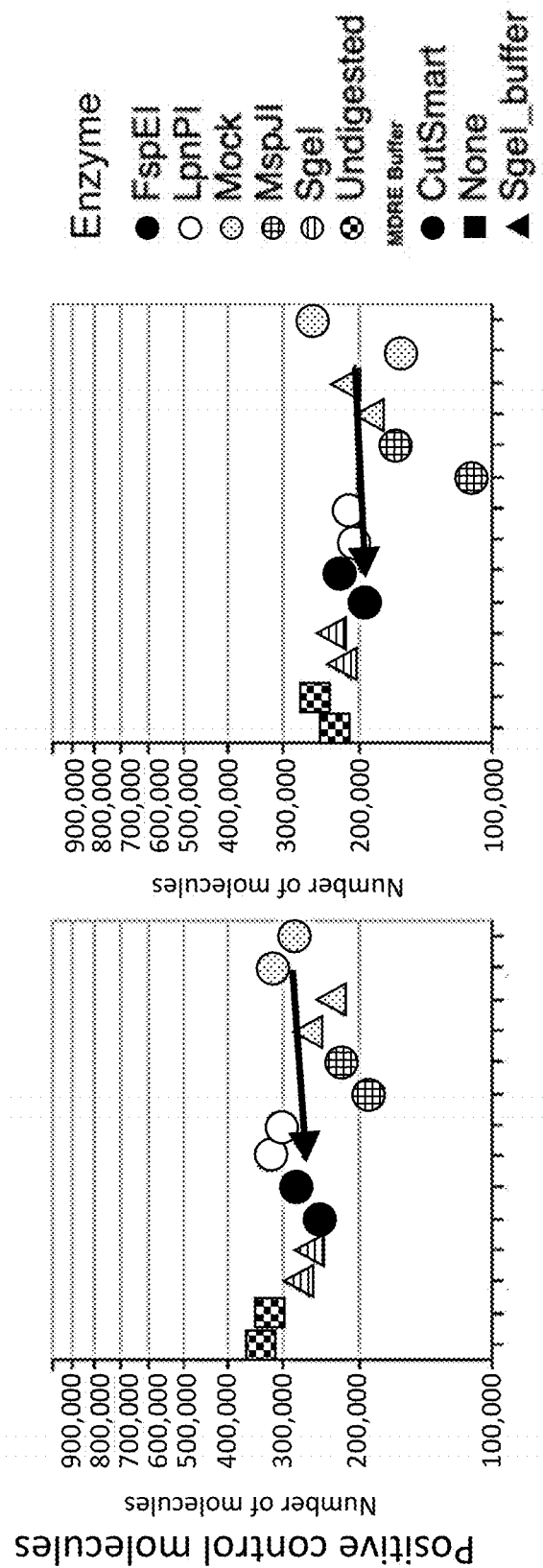
Figures 9A, 9B:
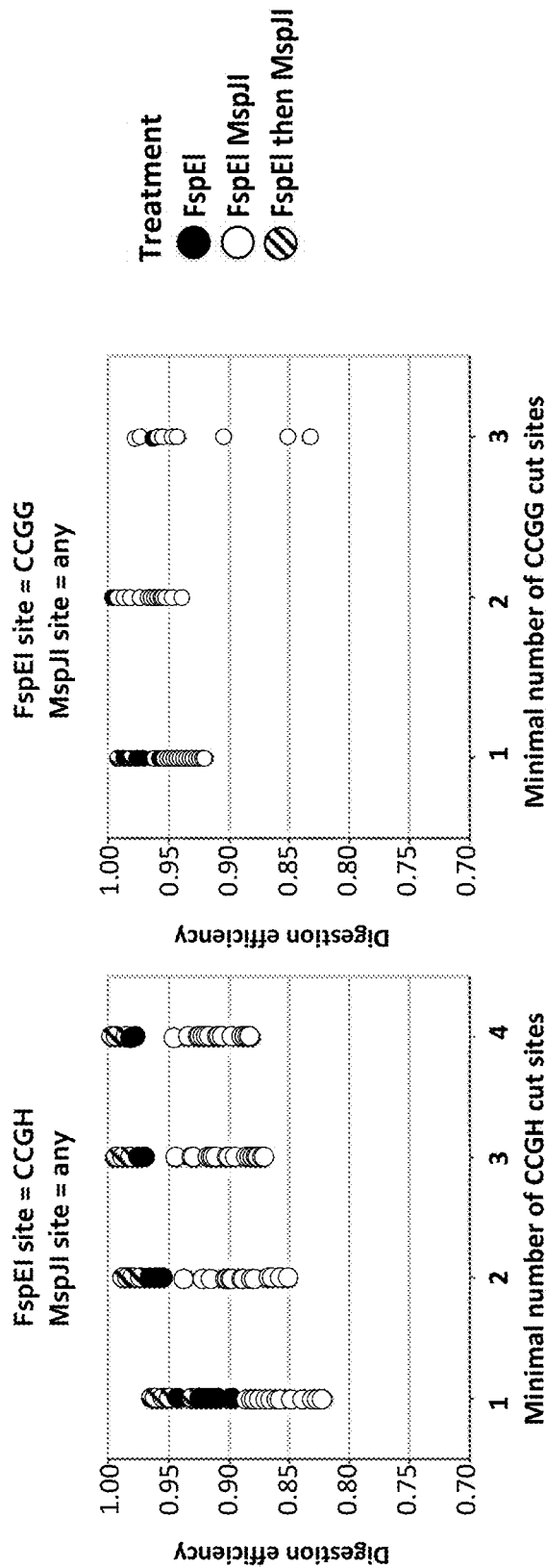
FIGS. 9A-D show digestion efficiency and positive control molecule counts as described in Example 4.
Figures 9C, 9D:
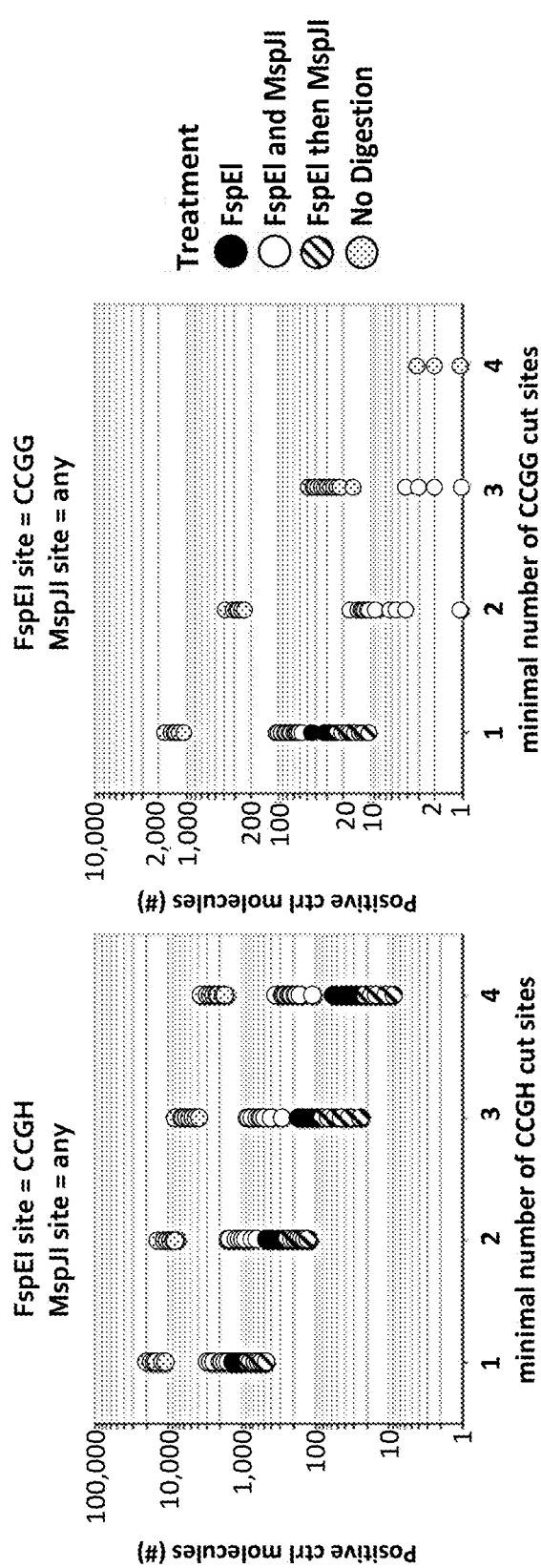

Multiple aliquots of cfDNA from two healthy donors were isolated and subjected to MBD-based partitioning of methylated cfDNA. The hypomethylated cfDNA partition was then subjected to ligation of NGS adapters onto the cfDNA molecules. Ligated cfDNA from each donor was then subjected to digestion with an MSRE that preferentially cleaves methylated DNA, also referred to as a methylation-dependent restriction enzyme (MDRE) digestion. The MDREs used were FspEI, LpnPI, MspJI, or SgeI, or a 'mock' digestion (no enzyme added to digestion) or an undigested condition in which the MDRE reaction was skipped as control reactions. After the MDRE step, the hypomethylated cfDNA partition was amplified in a universal PCR in which DNA that had been cleaved by the MDRE was not exponentially amplified because adapters were not present at each end. The PCR products were then subjected to enrichment of targeted genomic regions using a hybrid capture panel, amplified in a second PCR, and sequenced by NGS. The hybrid capture panel targets include 'positive control (ctrl)' and 'negative control (ctrl)' regions of the genome for enrichment. Positive control regions are CpG-dense regions of genome that are found to be ubiquitously highly methylated (>85% methylation by bisulfite-seq) in all human tissues including blood and cancerous tissue. Conversely, negative control regions are ubiquitously unmethylated (<15% methylation) in all human tissues. From the NGS analysis, the number of positive control molecules (i.e., molecules in the positive control regions) and negative control molecules (i.e., molecules in the negative control regions) sequenced in all the conditions are compared to estimate MDRE sensitivity and specificity, respectively. FIGS. 8A-B show that the FspEI enzyme treatment reduced the number of positive control molecules >100-fold compared to the 'mock' condition, demonstrating ~99% sensitivity with respect to digestion of methylated molecules. FIGS. 8C-D show that the FspEI treatment does not meaningfully reduce the negative control molecules, indicating high specificity with FspEI digestion (does not digest unmethylated molecules). Note that MspJI shows some sensitivity, but poor specificity compared to FspEI, while LpnI and SgeI show little/no sensitivity.

The MDRE digestion efficiency was calculated using molecules with different recognition sites and number of sites per molecule. Digestion efficiency is calculated as 1−[number of positive control molecules in MDRE condition]/[number of positive control molecules in the mock condition]. The general recognition sequence of FspEI that includes a $^{5m}$CpG is C$^{5m}$CGH (H=A, C, or T), with cleavage occurring 12-16 bases downstream. The FspEI palindromic site C$^{5m}$CGG contains two FspEI recognition sites—on the top and bottom strands in opposite directions. The general $^{5m}$CpG-containing consensus is $^{5m}$CpGNR, which can overlap with the FspEI consensus. FIGS. 9A-D show that digestion efficiency increases with the minimum number of C$^{5m}$CGH or C$^{5m}$CGG sites per molecule and is more efficient at the palindromic site (C$^{5m}$CGG). Positive control molecules with at least one C$^{5m}$CGG or at least two C$^{5m}$CGH sites were cleaved with 95% efficiency.

Additionally, digestion with FspEI and MspJI simultaneously or sequentially was tested. Sequential digestion with the two MDREs (FspEI then MspJI) had the highest efficiency. It is possible that in the simultaneous digestion (FspEI and MspJI), MspJI sometimes binds to the DNA but does not cleave (lower individual efficiency), thus sterically blocking the FspEI activity. Although FspEI then MspJI has higher overall efficiency than FspEI alone here, FspEI alone has better cleavage specificity. Thus, in different circumstances, digestion with FspEI alone or with FspEI then MspJI may be preferable. Note that with higher numbers of minimum sites there are fewer positive control molecules observed (FIGS. 9C-D) and thus the digestion efficiency estimate becomes more noisy.

Example 5: Detection of Tumor DNA Following MDRE Treatment cfDNA isolated from four healthy donors was used to create 'normal' and simulated 'cancer' cfDNA samples. The donor samples were used neat as 'normals' and spiked with the cfDNA of a colorectal cancer (CRC) patient to create a 'cancer' sample. The circulating tumor DNA fraction of the CRC cfDNA sample had been previously measured and was used to spike a calculated amount of CRC cfDNA into the normal donor cfDNA such that the resulting 'cancer' sample contained 0.5% circulating tumor DNA ("0.5% CRC" in FIGS. 10A-J). All the samples were subjected to MBD-based partitioning, splitting the cfDNA into hypermethylated and hypomethylated cfDNA partitions. The hypomethylated cfDNA partition was then ligated to NGS adapters. Ligated cfDNA from each donor was then subjected to a MDRE digestion with either FspEI, MspJI or FspEI+MspJI. A 'mock digestion' (no enzyme added to digestion reaction) and 'no digestion' condition (skip MDRE reaction altogether) served as control reactions. After the MDRE step, the non-digested hypomethylated partition cfDNA was amplified in a universal PCR, then subjected to enrichment of targeted genomic regions using a hybrid capture panel, and then amplified in a $2^{nd}$ PCR and sequenced by NGS. The hybrid capture panel targets include hypomethylation variable target regions and 'negative control (ctrl)' regions of the genome for enrichment. Negative control regions are CpG-dense regions of genome that are found to be ubiquitously lowly methylated (<15% methylation by bisulfite-seq) in all human tissues including blood and cancerous tissue. The hypomethylation variable target regions are genomic regions annotated in literature as having reduced methylation percentage in CRC tissue compared to healthy colon tissue and blood. From the NGS analysis, the number of hypomethylation variable target region molecules with 2 CCGG sites or more (which should be digested with high efficiency by the MDRE) is compared between 'normal' and 'cancer' samples across all the digestion conditions (FIGS. 10A-E). The ratios of the hypomethylation variable target region molecule counts were also compared to the negative control molecule counts, which normalizes for varying cfDNA input amounts that can affect the hypomethylation variable target region molecule counts (FIGS. 10F-J). No resolvable detection of the hypomethylation variable target region cancer signals was observed in the no MDRE digestion conditions ('no digestion' and 'mock digestion'). That is, the hypomethylation variable target region molecules and the normalized ratio levels were indistinguishable (not significantly different) between the 'cancer' and 'normal' samples (this is marked by the horizontal arrows in FIGS. 10C, E, H, and J). Conversely, when there was an MDRE treatment, a shift (increase) in the hypomethylation variable target region counts and normalized ratio was detected in the 'cancer' as compared to the 'normal' samples (marked by upward right arrow in FIGS. 10A, B, D, F, G, and I). Thus, the MDRE treatment enables detection of a cancer hypomethylation variable target region signal in the 'cancer' samples at 0.5% CRC ctDNA, that are not detectable by the MBD-partitioning assay alone.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the disclosure described herein may be employed in practicing the invention. It is therefore contemplated that the disclosure shall also cover any such alternatives, modifications, variations or equivalents. It is intended that the following claims define the scope of the invention and that methods and structures within the scope of these claims and their equivalents be covered thereby.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, systems, computer readable media, and/or component features, steps, elements, or other aspects thereof can be used in various combinations.

All patents, patent applications, websites, other publications or documents, accession numbers and the like cited herein are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number, if applicable. Likewise, if different versions of a publication, website or the like are published at different times, the version most recently published at the effective filing date of the application is meant, unless otherwise indicated.

What is claimed is:

1. A method for analyzing nucleic acid molecules in a biological sample, comprising:
   a) physically partitioning at least a subset of the nucleic acid molecules in the biological sample based on methylation status of the nucleic acid molecules into a plurality of partitioned sets, wherein the biological sample comprises methylated nucleic acid molecules and unmethylated nucleic acid molecules; the plurality of partitioned sets comprises a first partitioned set and a second partitioned set and the methylated nucleic acid molecules are overrepresented in the first partitioned set relative to the second partitioned set;
   b) digesting the first partitioned set with at least one methylation sensitive restriction enzyme, thereby removing incorrectly partitioned molecules; and
   c) sequencing at least a subset of the nucleic acid molecules of the first partitioned set.

2. The method of claim 1, further comprising determining methylation status at one or more genetic loci of the nucleic acid molecules in at least one of the partitioned sets.

3. The method of claim 1, further comprising capturing a first target region set from at least a portion of the first partitioned set, and capturing a second target region set from at least a portion of the second partitioned set.

4. The method of claim 3, wherein capturing the first target region set comprises contacting the DNA of the first partitioned set with a first set of target-specific probes, and capturing the second target region set comprises contacting the DNA of the second partitioned set with a second set of target-specific probes.

5. The method of claim 3, wherein
   a) the first target region set and/or the second target region set comprise epigenetic target regions;
   b) the first target region set and/or the second target region set comprise sequence-variable target regions; or
   c) both (a) and (b).

6. The method of claim 3, wherein the methylated nucleic acid molecules are overrepresented in the first partitioned set relative to the second partitioned set, the first target region set comprises epigenetic target regions, and the second target region set comprises sequence-variable target regions.

7. The method of claim 3, wherein the first partitioned set comprises hypermethylated DNA, the second partitioned set comprises hypomethylated DNA, the first target region set comprises epigenetic target regions, and the second target region set comprises sequence-variable target regions.

8. The method of claim 7, wherein the second target region set further comprises epigenetic target regions.

9. The method of claim 8, wherein the first target region set comprises epigenetic target regions comprising hypermethylation-variable target regions.

10. The method of claim 1, further comprising (a) detecting presence or absence of cancer in the biological sample, (b) determining a level of cancer in the biological sample, or (c) both (a) and (b).

11. The method of claim 1, further comprising, prior to the sequencing, amplifying at least a portion of the nucleic acid molecules, optionally wherein primers used in the amplification comprise at least one sample index.

12. The method of claim 1, wherein the methylation sensitive restriction enzyme selectively digests nucleic acid molecules that are unmethylated at the recognition site of the methylation sensitive restriction enzyme.

13. The method of claim 1, comprising digesting at least a subset of the one or more partitioned sets in the plurality of partitioned sets with at least two methylation sensitive restriction enzymes.

14. The method of claim 13, wherein the at least two methylation sensitive restriction enzymes comprise or consist of two or three methylation sensitive restriction enzymes.

15. The method of claim 1, wherein the at least one methylation sensitive restriction enzyme is selected from the group consisting of FspEI, LpnPI, MspJI, SgeI, AatII, AccII, AciI, Aor13HI, Aor15HI, BspT104I, BssHII, BstUI, Cfr10I, ClaI, CpoI, Eco52I, HaeII, HapII, HhaI, Hin6I, HpaII, HpyCH4IV, MluI, MspI, NaeI, NotI, NruI, NsbI, PmaCI, Psp1406I, PvuI, SacII, SalI, SmaI, and SnaBI.

16. The method of claim 1, wherein the at least one methylation sensitive restriction enzyme is selected from the group consisting of BstUI, HpaII, Hin6I, FspEI, LpnPI, MspJI, or SgeI.

17. The method of claim 1, further comprising, prior to the digesting step, attaching one or more adapters to at least one end of at least a portion of the nucleic acid molecules in the plurality of partitioned sets.

18. The method of claim 17, wherein the one or more adapters comprises at least one tag.

19. The method of claim 18, wherein the at least one tag comprises a molecular barcode.

20. The method of claim 1, wherein a first partitioned set of the plurality of partitioned sets is differentially tagged from a second partitioned set of the plurality of partitioned sets.

21. The method of claim 17, wherein the one or more adapters is resistant to digestion by the methylation sensitive restriction enzymes.

22. The method of claim 21, wherein the one or more adapters that is resistant to digestion by the methylation sensitive restriction enzymes comprises
   a) one or more methylated nucleotides, optionally wherein the methylated nucleotides comprise 5-methylcytosine and/or 5-hydroxymethylcytosine;
   b) one or more nucleotide analogs resistant to methylation sensitive restriction enzymes; or c) a nucleotide sequence not recognized by methylation sensitive restriction enzymes.

23. The method of claim 1, wherein the methylated nucleic acid molecules comprise 5-methylcytosine and/or 5-hydroxymethylcytosine.

24. The method of claim 1, wherein the biological sample is a cell-free DNA sample.

25. The method of claim 24, wherein the cell-free DNA is between 1 ng and 500 ng.

26. The method of claim 1, wherein the partitioning comprises partitioning the nucleic acid molecules based on a differential binding affinity of the nucleic acid molecules to a binding agent that preferentially binds to nucleic acid molecules comprising methylated nucleotides.

27. The method of claim 26, wherein the binding agent is a methyl binding domain (MBD) protein or an antibody that is specific to one or more methylated nucleotide bases.

28. The method of claim 5, wherein the epigenetic target regions comprise differentially methylated regions for cancer detection.

29. The method of claim 2, wherein the one or more genetic loci comprise one or more genomic regions.

\* \* \* \* \*